(12) United States Patent
Andresen

(10) Patent No.: US 10,266,828 B2
(45) Date of Patent: Apr. 23, 2019

(54) RAS EXON 2 SKIPPING FOR CANCER TREATMENT

(71) Applicant: Syddansk Universitet, Odense M (DK)

(72) Inventor: Brage Andresen, Abyhoj (DK)

(73) Assignee: Syddansk Universitet, Odense M (DK)

( * ) Notice: Subject to any disclaimer, the term of this patent is extended or adjusted under 35 U.S.C. 154(b) by 0 days.

(21) Appl. No.: 15/104,064

(22) PCT Filed: Dec. 16, 2014

(86) PCT No.: PCT/EP2014/078029
§ 371 (c)(1),
(2) Date: Jun. 13, 2016

(87) PCT Pub. No.: WO2015/091525
PCT Pub. Date: Jun. 25, 2015

(65) Prior Publication Data
US 2017/0240900 A1 Aug. 24, 2017

(30) Foreign Application Priority Data
Dec. 16, 2013 (DK) .................... 2013 70774

(51) Int. Cl.
*C07H 21/04* (2006.01)
*C12N 15/113* (2010.01)

(52) U.S. Cl.
CPC ...... *C12N 15/1135* (2013.01); *C12N 2310/11* (2013.01); *C12N 2310/314* (2013.01); *C12N 2310/315* (2013.01); *C12N 2310/321* (2013.01); *C12N 2310/322* (2013.01); *C12N 2310/3231* (2013.01); *C12N 2310/3233* (2013.01); *C12N 2310/3519* (2013.01); *C12N 2310/3521* (2013.01); *C12N 2310/3525* (2013.01); *C12N 2310/3533* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 5,401,837 | A | 3/1995 | Nelson |
| 5,734,039 | A | 3/1998 | Calabretta et al. |
| 5,962,218 | A | 10/1999 | Leland et al. |
| 6,077,668 | A | 6/2000 | Kool |
| 9,339,818 | B2 | 5/2016 | Cayre |
| 2003/0176385 | A1 | 9/2003 | Ju et al. |

FOREIGN PATENT DOCUMENTS

| | | |
|---|---|---|
| CN | 101955990 A | 1/2011 |
| EP | 0511559 A1 | 11/1992 |
| EP | 2511370 A1 | 10/2012 |
| EP | 2584343 A1 | 4/2013 |
| WO | WO 99/22772 | 5/1999 |
| WO | WO 99/54501 | 10/1999 |
| WO | WO 02/29005 A2 | 4/2002 |
| WO | WO 2004/015106 A1 | 2/2004 |
| WO | WO 2004/069992 A2 | 8/2004 |
| WO | WO 2005/066364 A1 | 7/2005 |
| WO | WO 2005/118824 A2 | 12/2005 |
| WO | WO 2007/031091 A2 | 3/2007 |
| WO | WO 2007/058894 A2 | 5/2007 |
| WO | WO 2008/153933 A2 | 12/2008 |
| WO | WO 2009/106760 A2 | 9/2009 |
| WO | WO 2010/083338 A2 | 7/2010 |
| WO | WO 2010/111682 A2 | 9/2010 |
| WO | WO 2011/130265 A2 | 10/2011 |
| WO | WO 2012/138487 A2 | 10/2012 |
| WO | WO 2013/129457 A1 | 9/2013 |
| WO | WO 2013/130882 | 9/2013 |
| WO | WO 2014/078749 A1 | 5/2014 |

OTHER PUBLICATIONS

Dias, et al; Antisense PNA Tridecamers Targeted to the Coding Region of Ha-ras mRNA Arrest Polypeptide Chain Elongation; Articie No. jmbi.1999.3277; Mol. Biol. (1999) 294, 403-416.

Mansoor et al, Advances in Antisense Oligonucleotide Development for Target Identification, Validation, and as Novel Therapeutics; National University of Singapore, Gene Regulation and Systems Biology 2008.2 275-295.

Aartsma-Rus, et al., Guidelines for Antisense Oligonucleotide Design and Insight Into Splice-modulating Mechanisms; Molecular Therapy, vol. 17 No. 3, 548-553, Mar. 2009.

Bhattacharyya, et al., Gene therapy developments for pancreatic cancer, Best Practice & Research Clinical Gastroenterology, vol. 20, No. 2 pp. 285-298, 2006.

Cogoi, et al., Transcription Inhibition of Oncogenic KRAS by a Mutation-Selective Peptide Nucleic Acid Conjugated to the PKK-KRKV Nuclear Localization Signal Peptide, Biochemistry, 44, 10510-10519, Jul. 14, 2005.

Disterer, et al.; Antisense-Mediated Exon-Skipping to Induce Gene Knockdown; Methods Molecular Biology 2012; 867, 289-305.

Fletcher et al.; Targeted Exon Skipping to Address "Leaky" Mutations in the Dystrophin Gene. Molecular Therapy Nucleic Acids, 1:e48, 2012.

(Continued)

*Primary Examiner* — Kimberly Chong
(74) *Attorney, Agent, or Firm* — Woodard, Emhardt, Henry, Reeves & Wagner, LLP

(57) ABSTRACT

There is provided SSOs targeting the region of HRAS, KRAS, and HRAS exon 2 that harbors the activating mutations and which harbors ESE activity. Moreover, there is provided SSOs targeting the 3'- and 5'-splice sites. The SSOs targeting the 5' splice site sequence of HRAS exon 2, the 3' splice site sequence of KRAS exon 2 and the 3' splice site sequence of NRAS exon 2, as well as SSOs that targets ESEs in a conserved part of exon 2 in the HRAS, KRAS and NRAS exon 2 sequences can induce complete or nearly complete exon 2 skipping in cancer cell lines. This results in growth and proliferation inhibition and concomitantly in death of cancer cells. Therefore this invention is directed towards treatment of cancerous diseases and other conditions where RAS signaling is involved.

11 Claims, 25 Drawing Sheets

Specification includes a Sequence Listing.

(56) References Cited

OTHER PUBLICATIONS

Gautherot et al.; A Multi-Model Approach to Nucleic Acid-Based Drug Development; Biodrugs 2004; 18 (1): 37-50.
Harding, et al.; The influence of Antisense Oligonucleotide Length on Dystrophin Exon Skipping; Molecular Therapy, vol. 15 No. 1, 157-166 (2007).
Helderman-Van Den Enden et al., Becker muscular dystrophy patients with deletions around exon 51: a promising outlook for exon skipping therapy in Duchenne patients. Neuromouscular Disorders, 20:251-254 (2010).
Hua et al., Antisense Masking of an hnRNP A1/A2 Intronic Splicing Silencer Corrects SMN2 Splicing in Transgenic Mice, America Journal of Human Genetics 82, 834-848, Apr. 2008.
Hua, et al., Antisense-mediated exon inclusion. Methods Molecular Biology, Cold Spring Harbor Laboratory, Cold Spring Harbor, New York 867:307-323 (2012).
Hua, et al., Enhancement of SMN2 Exon 7 Inclusion by Antisense Oligonucleotides Targeting the Exon; PloS Biology; Apr. 2007; vol. 5, Issue 4, e73.
Hua, et al., Peripheral SMN restoration is essential for long-term rescue of a severe spinal muscular atrophy mouse model. Nature Oct. 6, 2011, vol. 478, pp. 123-126.
Kang et al., Antisense-induced Myostatin Exon Skipping Leads to Muscle Hypertrophy in Mice Following Octa-guanidine Morpholino Oligomer Treatment; Molecular Therapy, vol. 19 No. 1, 159-164, Jan. 2011.
Kole, et al., RNA therapeutics: Beyond RNA interference and antisense oligonucleotides, HHS Public Access, Nature Rev Drug Discov.; 11(2): 125-140. Published by HHS Public Acess Feb. 5, 2016.
Lorenz et al.; Functional analysis of a duplication (p. E63-D69dup) in the switch II region HRAS:: new aspects of the molecular pathogenesis underlying Costello syndrome; Human Molecular Genetics, 2013, vol. 22, No. 8, 1643-1653.
Machine Translation of CN101955990A by Lexis Nexis Total Patent on Sep. 22, 2016.
Machine Translation of WO2005066364A1 by Lexis Nexis Total Patent on Sep. 22, 2016.
Machine Translation of WO2013/129457A1 by Lexis Nexis Total Patent on Sep. 22, 2016.
Pandith, et al; HRAS t81C polymorphism modulate risk of urinary bladder cancer and predicts advanced tumors in ethnic Kashmiri population; Urologic Oncology: Seminars and Original Investigations 31 (2013) pp. 487-492.
Peacey et al.; Targeting a pre-mRNA structure with bipartite antisense molecules modulates tau alternative splicing, Nucleic Acids Research, 9836-9849, 2012, vol. 40, No. 19.
Popplewell, et al., Comparaptive anlysis of antisense oligonucleotide sequences targeting exon 53 of the human DMD gene: Implications for future clinical trials, Neuromuscular Dislorders 20, 102-110 (2010).
Popplewell, et al., Design of Phosphorodiamidate Morpholino Oligomers (PMOs) for the Induction of Exon Skipping of the Human DMD Gene, Molecural Therapy, vol. 17 No. 3, 554-561, Mar. 2009.
Pramono, et al., A Prosecptive Study in the Rational Design of Efficient Antisense Oligonucleotides for Exon Skipping in the DMD Gene; Human Gene Therapy 23:781-790, Jul. 2012.
Stephenson, et al., Inhibition of Rous sarcoma viral RNA translation by a specific oligodexyribonucleotide; Proc. Natl, Acad. Sci., vol. 75, No. 1. pp. 285-288, Jan. 1978.
Wang, et al., Antisense Knockdown of Kras Inhibits Fibrosis in a Rat Model of Unilateral Ureteric Obstruction, The American Journal of Pathology, vol. 180, No. 1, pp. 82-90, Jan. 2012.
Yang, et al., Silencing of H-ras gene expression by retrovirus-mediated siRNA decreases transformation efficiency and tumorgrowth in a model of human ovarian cancer, Oncogene 22, 5694-5701 2003.
Zamecnik, et al., Inhibition of Rous sarcoma virus replication and cell transformation by a specific oligodeoxynucleotide, Proc. Natl. Acad. Sct, vol. 75 No. 1, pp. 280-284, Jan. 1978.
Wang, Antisense Knockdown of Kras Inhibits Fibrosis in a Rat Model of Unilateral Ureteric Obstruction website: http://www.sciencedirect.com/science/article/pii/S0002944011009291, 2012.
Wang, et al, Antisense Knockdown of Kras Inhibits Fibrosis in a Rat Model of Unilateral Ureteric Obstruction—Supplemental Materials downloaded from http://www.sciencedirect.com/science/article/pii/S0002944011009291, 2012.
Wang, et al., Antisense Knockdown of Kras Inhibits Fibrosis in a Rat Model of Unilateral Ureteric Obstruction and Supplemental Figures S1 S2 and S3, American Journal of Pathology, vol. 180, No. 1, Jan. 2012.

A. Splicing of exon 2 with ESE

B. SSO targeting ESE within exon 2

C. SSO targeting splice sites

SEQUENCE LISTING

```
<160> NUMBER OF SEQ ID NOS: 78

<210> SEQ ID NO 1
<211> LENGTH: 25
<212> TYPE: RNA
<213> ORGANISM: Artificial Sequence
<220> FEATURE:
<223> OTHER INFORMATION: splice shifting oliogonucleotide

<400> SEQUENCE: 1
cugccaagga gggcccugcu cagcc                                             25

<210> SEQ ID NO 2
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 2
cgcacucuug cccacaccgc cggcg                                             25

<210> SEQ ID NO 3
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 3
cucaccucua uagugggguc guauu                                             25

<210> SEQ ID NO 4
<211> LENGTH: 21
<212> TYPE: RNA
<213> ORGANISM: Artificial Sequence
<220> FEATURE:
<223> OTHER INFORMATION: splice shifting oligonucleotide

<400> SEQUENCE: 4
uugcccacac cgccggcgcc c                                                 21

<210> SEQ ID NO 5
<211> LENGTH: 21
<212> TYPE: RNA
<213> ORGANISM: Artificial Sequence
<220> FEATURE:
<223> OTHER INFORMATION: splice shifting oliognucleotide

<400> SEQUENCE: 5
uugcccacac cgacggcgcc c                                                 21
```

-continued

```
<210> SEQ ID NO 6
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 6
uauagugggg ucguauucgu ccaca                                          25

<210> SEQ ID NO 7
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 7
ugguucugga ucagcuggau gguca                                          25

<210> SEQ ID NO 8
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 8
cgggguccuc cuacaggguc uccug                                          25

<210> SEQ ID NO 9
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 9
gucaucgcuc cucaggggcc ugcgg                                          25

<210> SEQ ID NO 10
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 10
cccaccacca ccagcuuaua uuccg                                          25

<210> SEQ ID NO 11
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 11
gggucuccug ccccaccugc caagg                                          25

<210> SEQ ID NO 12
<211> LENGTH: 25
<212> TYPE: RNA
<213> ORGANISM: Artificial Sequence
<220> FEATURE:
<223> OTHER INFORMATION: splice shifting oligonucleotide
```

```
<400> SEQUENCE: 12
uucagucauu uucagcaggc cuuau                                          25

<210> SEQ ID NO 13
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 13
uuuaccucua uuguuggauc auauu                                          25

<210> SEQ ID NO 14
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 14
augaaaaugg ucagagaaac cuuua                                          25

<210> SEQ ID NO 15
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 15
ucuguaucaa agaauggucc ugcac                                          25

<210> SEQ ID NO 16
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 16
caguaauaug cauauuaaaa caaga                                          25

<210> SEQ ID NO 17
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 17
aauaaaaaua augaaaaugu gacua                                          25

<210> SEQ ID NO 18
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 18
uauuagaaca ugucacacau aaggu                                          25
```

```
<210> SEQ ID NO 19
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 19
aguuuauauu cagucauuuu cagca                                              25

<210> SEQ ID NO 20
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 20
uacgccacca gcuccaacua ccaca                                              25

<210> SEQ ID NO 21
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 21
gcuguaucgu caaggcacuc uugcc                                              25

<210> SEQ ID NO 22
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 22
ucguccacaa aaugauucug aauua                                              25

<210> SEQ ID NO 23
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 23
uuucacacca gcaagaaccu guugg                                              25

<210> SEQ ID NO 24
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 24
ccucaccucu auggugggau cauau                                              25

<210> SEQ ID NO 25
<211> LENGTH: 25
<212> TYPE: RNA
<213> ORGANISM: Artificial Sequence
<220> FEATURE:
<223> OTHER INFORMATION: splice shifting oligonucleotide
```

<400> SEQUENCE: 25
accaccaguu uguacucagu cauuu                                    25

<210> SEQ ID NO 26
<211> LENGTH: 25
<212> TYPE: RNA
<213> ORGANISM: Artificial Sequence
<220> FEATURE:
<223> OTHER INFORMATION: splice shifting oligonucleotides

<400> SEQUENCE: 26
caacaccacc ugcuccaacc accac                                    25

<210> SEQ ID NO 27
<211> LENGTH: 25
<212> TYPE: RNA
<213> ORGANISM: Artificial Sequence
<220> FEATURE:
<223> OTHER INFORMATION: splice shifting oligonucleotides

<400> SEQUENCE: 27
gugcgcuuuu cccaacacca ccugc                                    25

<210> SEQ ID NO 28
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 28
ugguucugga uuagcuggau uguca                                    25

<210> SEQ ID NO 29
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 29
ggugggauca uauucaucua caaag                                    25

<210> SEQ ID NO 30
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 30
aaucaggguu aauuggcgag ccaca                                    25

<210> SEQ ID NO 31
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 31
caggaucagg ucagcgggcu accac                                    25

```
<210> SEQ ID NO 32
<211> LENGTH: 20
<212> TYPE: RNA
<213> ORGANISM: Artificial Sequence
<220> FEATURE:
<223> OTHER INFORMATION: tail sequence

<400> SEQUENCE: 32
gacgaaucag gguucagggu                                                   20

<210> SEQ ID NO 33
<211> LENGTH: 19
<212> TYPE: RNA
<213> ORGANISM: Artificial Sequence
<220> FEATURE:
<223> OTHER INFORMATION: tail sequence

<400> SEQUENCE: 33
caggguucag gguuagagg                                                    19

<210> SEQ ID NO 34
<211> LENGTH: 19
<212> TYPE: RNA
<213> ORGANISM: Artificial Sequence
<220> FEATURE:
<223> OTHER INFORMATION: tail sequence

<400> SEQUENCE: 34
gacgaauagg gauuaggga                                                    19

<210> SEQ ID NO 35
<211> LENGTH: 19
<212> TYPE: RNA
<213> ORGANISM: Artificial Sequence
<220> FEATURE:
<223> OTHER INFORMATION: tail sequence

<400> SEQUENCE: 35
uagggauuag ggauagagg                                                    19

<210> SEQ ID NO 36
<211> LENGTH: 21
<212> TYPE: RNA
<213> ORGANISM: Artificial Sequence
<220> FEATURE:
<223> OTHER INFORMATION: tail sequence

<400> SEQUENCE: 36
gacgaaucag gguuucaggg u                                                 21

<210> SEQ ID NO 37
<211> LENGTH: 20
<212> TYPE: RNA
<213> ORGANISM: Artificial Sequence
<220> FEATURE:
<223> OTHER INFORMATION: tail sequence

<400> SEQUENCE: 37
caggguuuca ggguuagagg                                                   20

<210> SEQ ID NO 38
<211> LENGTH: 13
<212> TYPE: RNA
<213> ORGANISM: Artificial Sequence
<220> FEATURE:
<223> OTHER INFORMATION: tail sequence
```

```
<400> SEQUENCE: 38
gcgcccaggg ugu                                                          13

<210> SEQ ID NO 39
<211> LENGTH: 13
<212> TYPE: RNA
<213> ORGANISM: Artificial Sequence
<220> FEATURE:
<223> OTHER INFORMATION: tail sequence

<400> SEQUENCE: 39
cagggugugg gca                                                          13

<210> SEQ ID NO 40
<211> LENGTH: 13
<212> TYPE: RNA
<213> ORGANISM: Artificial Sequence
<220> FEATURE:
<223> OTHER INFORMATION: tail sequence

<400> SEQUENCE: 40
gcgccuaggg agu                                                          13

<210> SEQ ID NO 41
<211> LENGTH: 14
<212> TYPE: RNA
<213> ORGANISM: Artificial Sequence
<220> FEATURE:
<223> OTHER INFORMATION: tail sequence

<400> SEQUENCE: 41
cuagggagug ggca                                                         14

<210> SEQ ID NO 42
<211> LENGTH: 25
<212> TYPE: RNA
<213> ORGANISM: Artificial Sequence
<220> FEATURE:
<223> OTHER INFORMATION: control splice shifting oligonucleotide

<400> SEQUENCE: 42
gcucaauaug cuacugccau gcuug                                             25

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
aggctcagcg gctcccaggt g                                                 21

<210> SEQ ID NO 44
<211> LENGTH: 36
<212> TYPE: DNA
<213> ORGANISM: Artificial Sequence
<220> FEATURE:
<223> OTHER INFORMATION: primer

<400> SEQUENCE: 44
gagtccttaa ctcttttaat ttgttctcta taatgg                                 36
```

```
<210> SEQ ID NO 45
<211> LENGTH: 27
<212> TYPE: DNA
<213> ORGANISM: Artificial Sequence
<220> FEATURE:
<223> OTHER INFORMATION: primer

<400> SEQUENCE: 45
ggccccgcta gcagtcgcgc ctgtgaa                                          27

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
cgtttgatct gctccctgta c                                                21

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
attaatacga ctcactatag gg                                               22

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
cgtttgatct gctccctgta c                                                21

<210> SEQ ID NO 49
<211> LENGTH: 31
<212> TYPE: DNA
<213> ORGANISM: Artificial Sequence
<220> FEATURE:
<223> OTHER INFORMATION: primer

<400> SEQUENCE: 49
ctaaatctgt ccaaagcaga ggcagtggag c                                     31

<210> SEQ ID NO 50
<211> LENGTH: 35
<212> TYPE: DNA
<213> ORGANISM: Artificial Sequence
<220> FEATURE:
<223> OTHER INFORMATION: primer

<400> SEQUENCE: 50
tcttttactc gcttaatctg ctccctgtag aggtt                                 35

<210> SEQ ID NO 51
<211> LENGTH: 22
<212> TYPE: RNA
<213> ORGANISM: Artificial Sequence
<220> FEATURE:
<223> OTHER INFORMATION: affinity sequence
```

```
<400> SEQUENCE: 51
ggugggcgcc ggcggugugg gc                                              22

<210> SEQ ID NO 52
<211> LENGTH: 22
<212> TYPE: RNA
<213> ORGANISM: Artificial Sequence
<220> FEATURE:
<223> OTHER INFORMATION: affinity seqquence

<400> SEQUENCE: 52
ggugggcgcc gucggugugg gc                                              22

<210> SEQ ID NO 53
<211> LENGTH: 22
<212> TYPE: RNA
<213> ORGANISM: Artificial Sequence
<220> FEATURE:
<223> OTHER INFORMATION: affinity seqquence

<400> SEQUENCE: 53
ggugggcgcc gugggugugg gc                                              22

<210> SEQ ID NO 54
<211> LENGTH: 26
<212> TYPE: DNA
<213> ORGANISM: Artificial Sequence
<220> FEATURE:
<223> OTHER INFORMATION: primer

<400> SEQUENCE: 54
gtgaaggact cgagtgacgt gcccat                                          26

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
cgtttgatct gctcctgtac                                                 20

<210> SEQ ID NO 56
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 56
guauucgucc acaaaauggu ucugg                                           25

<210> SEQ ID NO 57
<211> LENGTH: 20
<212> TYPE: RNA
<213> ORGANISM: Artificial Sequence
<220> FEATURE:
<223> OTHER INFORMATION: splice shifting oligonucleotide

<400> SEQUENCE: 57
uucguccaca aaaugguucu                                                 20
```

```
<210> SEQ ID NO 58
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 58
guauucgucc acaaaguggu ucugg                                    25

<210> SEQ ID NO 59
<211> LENGTH: 20
<212> TYPE: RNA
<213> ORGANISM: Artificial Sequence
<220> FEATURE:
<223> OTHER INFORMATION: splice shifting oligonucleotide

<400> SEQUENCE: 59
uucguccaca aagugguucu                                          20

<210> SEQ ID NO 60
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 60
gccuacgcca ccagcuccaa cuacc                                    25

<210> SEQ ID NO 61
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 61
cuugccuacg ccaccagcuc caacu                                    25

<210> SEQ ID NO 62
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 62
acucuugccu acgccaccag cucca                                    25

<210> SEQ ID NO 63
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 63
ggcacucuug ccuacgccac cagcu                                    25

<210> SEQ ID NO 64
<211> LENGTH: 25
<212> TYPE: RNA
<213> ORGANISM: Artificial Sequence
<220> FEATURE:
<223> OTHER INFORMATION: splice shifting oligonucleotide
```

```
<400> SEQUENCE: 64
caaggcacuc uugccuacgc cacca                                    25

<210> SEQ ID NO 65
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 65
cgucaaggca cucuugccua cgcca                                    25

<210> SEQ ID NO 66
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 66
uaucgucaag gcacucuugc cuacg                                    25

<210> SEQ ID NO 67
<211> LENGTH: 25
<212> TYPE: RNA
<213> ORGANISM: Artificial Sequence
<220> FEATURE:
<223> OTHER INFORMATION: splice shifting oligonucleotide

<400> SEQUENCE: 67
gccaccagcu ccaacuacca caagu                                    25

<210> SEQ ID NO 68
<211> LENGTH: 22
<212> TYPE: RNA
<213> ORGANISM: Artificial Sequence
<220> FEATURE:
<223> OTHER INFORMATION: splice shifting oligonucleotide

<400> SEQUENCE: 68
uacgccacca gcuccaacua cc                                       22

<210> SEQ ID NO 69
<211> LENGTH: 22
<212> TYPE: RNA
<213> ORGANISM: Artificial Sequence
<220> FEATURE:
<223> OTHER INFORMATION: splice shifting oligonucleotide

<400> SEQUENCE: 69
gccuacgcca ccagcuccaa cu                                       22

<210> SEQ ID NO 70
<211> LENGTH: 22
<212> TYPE: RNA
<213> ORGANISM: Artificial Sequence
<220> FEATURE:
<223> OTHER INFORMATION: splice shifting oligonucleotide

<400> SEQUENCE: 70
cuugccuacg ccaccagcuc ca                                       22
```

```
<210> SEQ ID NO 71
<211> LENGTH: 22
<212> TYPE: RNA
<213> ORGANISM: Artificial Sequence
<220> FEATURE:
<223> OTHER INFORMATION: splice shifting oligonucleotide

<400> SEQUENCE: 71
acucuugccu acgccaccag cu                                                  22

<210> SEQ ID NO 72
<211> LENGTH: 22
<212> TYPE: RNA
<213> ORGANISM: Artificial Sequence
<220> FEATURE:
<223> OTHER INFORMATION: splice shifting oligonucleotide

<400> SEQUENCE: 72
ggcacucuug ccuacgccac ca                                                  22

<210> SEQ ID NO 73
<211> LENGTH: 22
<212> TYPE: RNA
<213> ORGANISM: Artificial Sequence
<220> FEATURE:
<223> OTHER INFORMATION: splice shifting oligonucleotide

<400> SEQUENCE: 73
caaggcacuc uugccuacgc ca                                                  22

<210> SEQ ID NO 74
<211> LENGTH: 20
<212> TYPE: RNA
<213> ORGANISM: Artificial Sequence
<220> FEATURE:
<223> OTHER INFORMATION: splice shifting oligonucleotide

<400> SEQUENCE: 74
cuugccuacg ccaucagcuc                                                     20

<210> SEQ ID NO 75
<211> LENGTH: 20
<212> TYPE: RNA
<213> ORGANISM: Artificial Sequence
<220> FEATURE:
<223> OTHER INFORMATION: splice shifting oligonucleotide

<400> SEQUENCE: 75
uucguccaca aaaugauucu                                                     20

<210> SEQ ID NO 76
<211> LENGTH: 270
<212> TYPE: DNA
<213> ORGANISM: Homo sapiens
<220> FEATURE:
<223> OTHER INFORMATION: HRAS exon 2 and flanking sequences

<400> SEQUENCE: 76
ccctgtgggg cctggggctg ggcctgggcc tggctgagca gggccctcct tggcaggtgg         60
ggcaggagac cctgtaggag daccccgggc cgcaggcccc tgaggagcga tgacggaata        120
taagctggtg gtggtgggcg ccggcggtgt gggcaagagt gcgctgacca tccagctgat        180
ccagaaccat tttgtggacg aatacgaccc cactatagag gtgagcctgg cgccgccgtc       240
caggtgccag cagctgctgc gggcgagccc                                        270
```

```
<210> SEQ ID NO 77
<211> LENGTH: 260
<212> TYPE: DNA
<213> ORGANISM: Homo sapiens
<220> FEATURE:
<223> OTHER INFORMATION: KRAS exon2 and flanking sequences

<400> SEQUENCE: 77
ggagtatttg atagtgtatt aaccttatgt gtgacatgtt ctaatatagt cacattttca      60
ttatttttat tataaggcct gctgaaaatg actgaatata aacttgtggt agttggagct     120
ggtggcgtag gcaagagtgc cttgacgata cagctaattc agaatcattt tgtggacgaa     180
tatgatccaa caatagaggt aaatcttgtt ttaatatgca tattactggt gcaggaccat     240
tctttgatac agataaaggt                                                 260

<210> SEQ ID NO 78
<211> LENGTH: 260
<212> TYPE: DNA
<213> ORGANISM: Homo sapiens
<220> FEATURE:
<223> OTHER INFORMATION: NRAS exon2 and flanking sequences

<400> SEQUENCE: 78
ctttaaagta ctgtagatgt ggctcgccaa ttaaccctga ttactggttt ccaacaggtt      60
cttgctggtg tgaaatgact gagtacaaac tggtggtggt tggagcaggt ggtgttggga     120
aaagcgcact gacaatccag ctaatccaga accactttgt agatgaatat gatcccacca     180
tagaggtgag gcccagtggt agcccgctga cctgatcctg tctctcactt gtcggatcat     240
ctttacccat attctgtatt                                                 260
```

RAS EXON 2 SKIPPING FOR CANCER TREATMENT

FIELD OF THE INVENTION

The present invention relates to splice shifting oligonucleotides (SSOs) targeting exon 2 in the pre-mRNA transcript of the RAS genes, H-RAS, K-RAS and N-RAS, that harbors cancer activating mutations. Specifically, the SSOs induce exon 2 skipping in cancer cells thereby decreasing RAS signaling, causing decreased proliferation and or cell death. Therefore this invention is directed towards treatment of cancerous diseases and other conditions where RAS signaling is involved.

BACKGROUND OF THE INVENTION

Newly synthesized eukaryotic mRNA molecules, also known as primary transcripts or pre-mRNA, made in the nucleus, are processed before or during transport to the cytoplasm for translation. Processing of the pre-mRNAs includes addition of a 5' methylated cap and an approximately 200-250 nucleotides poly(A) tail to the 3' end of the transcript.

Another step in mRNA processing is splicing of the pre-mRNA, which is part of the maturation of 90-95% of mammalian mRNAs. Introns (or intervening sequences) are regions of a primary transcript that are not included in the coding sequence of the mature mRNA. Exons are regions of a primary transcript that remain in the mature mRNA when it reaches the cytoplasm. The exons are spliced together to form the mature mRNA sequence. Splice junctions are also referred to as splice sites with the junction at the 5' end of the intron often called the "5' splice site," or "splice donor site" and the junction at the 3' end of the intron called the "3' splice site" or "splice acceptor site." In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Alternative splicing, defined as the splicing together of different combinations of exons or exon segments, often results in multiple mature mRNA transcripts expressed from a single gene.

The splicing of precursor mRNA (pre-mRNA) is an essential step in eukaryotic gene expression, where introns are removed through the activities of the spliceosome, and the coding parts of a gene are spliced together, resulting in a functional mRNA. Pre-mRNA splicing is a highly controlled process and it is well established that mutations can impact splicing and generate aberrant transcripts [Andresen and Krainer 2009; Adkin et al. 2012, Olsen et al. 2014]. Correct mRNA splicing depends on regulatory sequences, which are recognized by different factors of the spliceosome, as well as splicing regulatory factors. The splicing regulatory factors either stimulate or repress recognition and splicing of exons by sequence specific binding to splicing regulatory sequences such as splicing enhancers and splicing silencers [Divina et al. 2009]. Pre-mRNA splicing in eukaryotes is often associated with extensive alternative splicing to enrich their proteome [Black 2000]. Alternative selection of splice sites permits eukaryotes to modulate cell type specific gene expression, contributing to their functional diversification. Alternative splicing is a highly regulated process influenced by the splicing regulatory proteins, such as SR proteins or hnRNPs, which recognize splicing regulatory sequences, such as exonic splicing enhancers (ESEs) and exonic splicing silencers (ESSs) in exons [Busch and Hertel 2012].

It is a well-known fact that exonic mutations, which either create or eliminate existing splicing regulatory sequences other than the splice site sequences often lead to misplicing of the RNA that might result in diseases. However, it is difficult to predict which mutations affect splicing as not all exons are critically dependent on splicing regulatory elements other than the splice sites, and consequently only a limited number of exons are vulnerable to mutations in splicing regulatory sequences outside of the splice sites [Andresen and Krainer 2009].

In recent years, a new class of genetic diseases has emerged that includes the clinically overlapping disorders Cardio-facio-cutaneous (CFC), Noonan and Costello syndromes (NS and CS, respectively). Even though genetic studies have revealed both molecular and clinical heterogeneity of these disorders, the common denominator is the association to the RAS-MAP kinase pathway and the class I phosphoinositide 3-kinase (PI3K) pathway [reviewed by Zenker 2011].

Costello syndrome is a rare inherited congenital disorder with a characteristic prenatal phenotype, caused by activating germline mutations in HRAS proto-oncogene [Aoki et al. 2005]. Costello syndrome belongs to a class of genetic syndromes that are caused by disorder of the RAS-MAP kinase pathway and the PI3K/Akt pathway. The HRAS protein is important in correct regulation of cell growth and division, and mutations in the HRAS gene might lead to numerous types of cancers, such as lung, skin, breast and colon. It has been observed in Costello patients as well as sporadic cancers that mutations in exon 2 of the gene, leads to a constitutive active HRAS protein, loss of cell cycle control and development of cancer.

Costello syndrome is usually caused by dominant negative germline mutations in HRAS exon 2, changing the codon for Glycine 12 or Glycine 13 to other amino acids. Such mutations results in a constitutive active Ras protein and activation of the Ras/MAPK and PI3K/Akt pathways, causing multiple developmental defects and a predisposition to cancer. Interestingly, the vast majority of somatic HRAS mutations in cancers change the codon for Glycine 12 to Valine, with a c.35G>T mutation being extremely frequent. Glycine 12 to Valine (G12V) mutations are rare in Costello syndrome patients, and usually cause a very severe clinical phenotype when present.

The three closely related human RAS genes, HRAS, KRAS and NRAS are all widely expressed and are important for regulation of numerous cellular processes through the RAS-MAP-kinase and PI3K/Akt pathways. They each exhibit oncogenic activity and more than 30% of all human tumors have mutations leading to constitutively active RAS proteins [Quinlan et al. 2008]. Different RAS oncogenes are preferentially associated with different types of human cancer [Parikh et al. 2007]. Therefore, the RAS oncogenes are already targets for numerous different anticancer treatments.

Knock down of expression from the dominant negative mutant HRAS allele does have enormous therapeutic potential for treating patients suffering from numerous types of cancers, and potentially also patients suffering from Costello syndrome and other Rasopathies.

Knock down of gene expression can be achieved by skipping of vulnerable exons during pre-mRNA splicing. This can be accomplished by using splice shifting oligonucleotides (SSOs) targeted to splicing regulatory signals, such as the splice sites or exon splicing enhancers (ESEs) which are fundamental for inclusion of weak exons (Kole et al. 2012). Exons which are weakly defined and thus difficult to splice often exhibit minimal levels of exon skipping also from wild type alleles. This type of vulnerable exons are preferred as targets for SSO mediated exon skipping (Fletcher et al. 2012).

SSOs have significant advances over existing therapeutic approaches: 1. SSOs target gene-specific sequences, which ensures that side-effects are minimal. 2. In sharp contrast to other antisense technologies SSOs are chemically modified to ensure superior long term stability and avoid degradation of the target mRNA. They can be further modified for enhanced cellular uptake and specific cancer cell targeting. 3. Contrary to RNAi, SSOs do not depend on the cellular RISC/RNase H or other cellular systems mediating mRNA degradation.

For efficient knock down by SSOs it is crucial that the targeted exon is weakly defined/vulnerable and thus critically dependent on a finely tuned balance between splicing enhancers and splicing silencers. Vulnerability is usually caused by weak splice sites and/or overrepresentation of exonic splicing silencers (ESSs) and/or underrepresentation of exonic splicing enhancers (ESEs) in the vulnerable exon.

SSO can mediate alternative splicing of the targeted pre-mRNA and thereby simultaneously lead to production of new protein isoforms with a dominant negative effect thereby further potentiating the effect of down regulation of the normal protein isoform.

SUMMARY OF THE INVENTION

The present inventors have designed SSOs targeting sequences in HRAS exon 2 that harbors the activating mutations and sequences, which the inventors have shown to harbor ESE activity. Moreover, the inventors have designed SSOs targeting the 3'- and 5'-splice sites. The inventors have shown that the SSO targeting the 5' splice site sequence, the 3' splice site sequence and the SSOs that targets different ESE containing segments of the HRAS exon 2 sequence can induce nearly complete exon 2 skipping in cancer cell lines like HepG2 and T24. The inventors have shown that skipping of exon 2 mediated by SSO treatment concomitantly results in reduced growth and proliferation and death of cancer cells. The inventors have performed such studies also in the homologous genes NRAS and KRAS, and found that SSOs targeting the splice sites and the regions with ESE elements also cause skipping of the vulnerable exon 2 from these genes, leading to reduced growth and proliferation and death of cancer cells. Thus the concepts applicable to HRAS are applicable to NRAS and KRAS as well. Hence, SSOs that target the splice sites and different ESE containing segments of HRAS, KRAS or NRAS exon 2 belong to the present invention. In one embodiment, the SSOs of the present invention target the splice donor site of exon 2 in any one of HRAS, KRAS or NRAS. In one embodiment, the SSOs of the present invention target one or more ESE containing segments in exon 2 of any one of HRAS, KRAS or NRAS. In one embodiment, the SSOs of the present invention target the splice acceptor site of exon 2 in any one of HRAS, KRAS or NRAS. In one embodiment, the SSOs of the present invention target either a splice acceptor site or a splice donor site of exon 2 and additionally also one or more ESEs in exon 2 of any one of HRAS, KRAS or NRAS.

The SSOs are complementary to a target region of the RAS, such as any one of the HRAS, KRAS or NRAS transcripts comprising exon 2. In certain embodiments, the RAS, such as HRAS, transcript harbors a mutation. In certain embodiments, splice shifting oligonucleotides stimulate aberrant splicing of a mutant RAS transcript.

Specifically the present invention provides a compound comprising a modified oligonucleotide consisting of 5 to 25 linked nucleosides and having a nucleobase sequence comprising at least 5 contiguous nucleobases complementary to a target region of equal length of an RAS transcript, said target region being the donor or acceptor site of HRAS exon 2, NRAS exon 2 or KRAS exon 2.

In a preferred embodiment the nucleobase sequence comprises at least 7 contiguous nucleobases complementary to exon 2 of an HRAS, NRAS, or KRAS transcript.

Preferably the modified oligonucleotide comprises at least one modified nucleoside, such as a modified nucleoside comprising a modified sugar moiety, such as a 2'-substituted sugar moiety, such as LNA.

Preferably the oligonucleotide is targeted to one or more (exonic) splicing enhancer element(s).

In one aspect of the present invention the target region is the donor or acceptor site of HRAS exon 2 and the compound is selected from SEQ IDs NO 1, 3 or 11 or sequences having at least 80% homology, or 1 or 2 mismatches therewith.

In another aspect of the present invention the target region is the donor or acceptor site of KRAS exon 2 and the compound is selected from SEQ IDs NO 12-18 or sequences having at least 80% homology, or 1 or 2 mismatches therewith.

In still another aspect of the present invention the target region is the donor or acceptor site of NRAS exon 2 and the compound is selected from SEQ IDs NO 23, 24, 30 or 31 or sequences having at least 80% homology, or 1 or 2 mismatches therewith.

The compounds of the present invention are suitably for use in treating cancer, such as, but not limited to, colorectal, breast, bladder, skin, kidney, liver, pancreatic, prostate cancer and hematological cancers, like multiple myeloma, acute myeloblastic leukemia, chronic myelogenic leukemia, acute lymphoblastic leukemia and chronic lymphocytic leukemia.

The present invention further provides a method of modulating splicing in a transcript in a cell comprising contacting the cell with a compound of the present invention.

The present invention further provides a method of modulating splicing in a transcript in a cell comprising contacting the cell with a composition comprising two, three or four SSO's according to the present invention.

The present invention further provides a method of modulating splicing in a transcript in a cell comprising contacting the cell with a composition comprising two, three or four SSO's according to the present invention, wherein the cell is in a patient suffering from a RAS related cancer, and/or a Rasopathy such as Costello syndrome.

The present invention also provides a method for treating a condition characterized at least in part by constitutively active RAS or mutant RAS, comprising administering a therapeutically effective amount of the compound of the present invention to a subject in need thereof.

This shows that there are several ESEs in HRAS exon 2 that are important for inclusion of exon 2 and that exon 2 is skipped during splicing if the function of ESE-B, ESE-C or ESE-D is disrupted.

Figure 6:
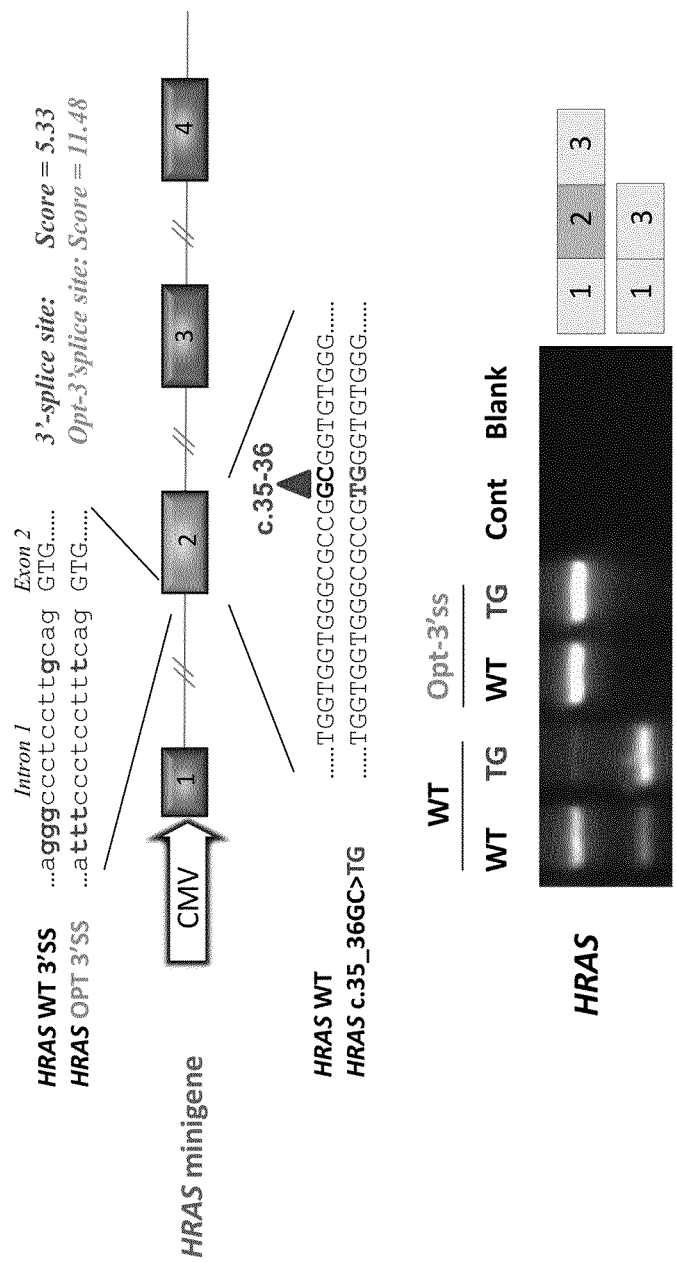

FIG. 6 shows that the 3'-splice site flanking HRAS exon 2, is weak with a low splice site score and therefore exon 2 is likely to be dependent on ESE's in order to be recognized efficiently. This is in particular due to the presence of a GGG triplet in the polypyrimidine tract of the weak 3' splice site which represents a binding site for splicing inhibitory proteins from the hnRNPF/H family, which could compete with U2AF65 binding to the 3'-splice site of HRAS exon 2 and thereby decrease splicing efficiency. Since hnRNPF/H binding to GGG triplets in a pre-mRNA is cooperative and synergistic [Schaub et al. 2007; Masuda et al. 2008; Dobrowolski et al. 2010; Olsen et al. 2014], mutations creating new GGG triplets in exon 2 or binding of splice shifting oligo nucleotides (SSOs) with tails harboring such motifs (SEQ ID NO 32 to SEQ ID NO 41 are likely to inhibit splicing by acting in synergy with pre-existing GGG triplets, such as the GGG triplet in the weak HRAS exon 2 3'-splice site. It is in this figure demonstrated that optimization of the weak HRAS exon 2 3' splice site, by replacement of the GGG triplet with consensus T nucleotides in the HRAS WT minigene, corrects splicing. This confirms that HRAS exon 2 is only vulnerable due to the weak splice sites and that inactivation of ESEs lead to exon 2 skipping only because the weak splice sites require functional ESEs in order to be recognized and mediate exon 2 inclusion into the HRAS mRNA. The listed mutations were introduced by site directed mutagenesis into the minigene, which was transfected into HepG2 cells. 48 hours post transfection RNA was extracted, cDNA prepared and an HRAS exon 2 skipping was analyzed by PCR. PCR products were analyzed by electrophoresis in an agarose gel. The transfections were performed in triplicate and the experiments repeated twice using Lipofectamine® RNAiMax. 3'ss: 3' splice site, 5'ss: 5' splice site, Blank: Represents a control PCR without added cDNA. Control: represent a sample transfected with a control plasmid with no HRAS sequence inserted.

Figure 7:
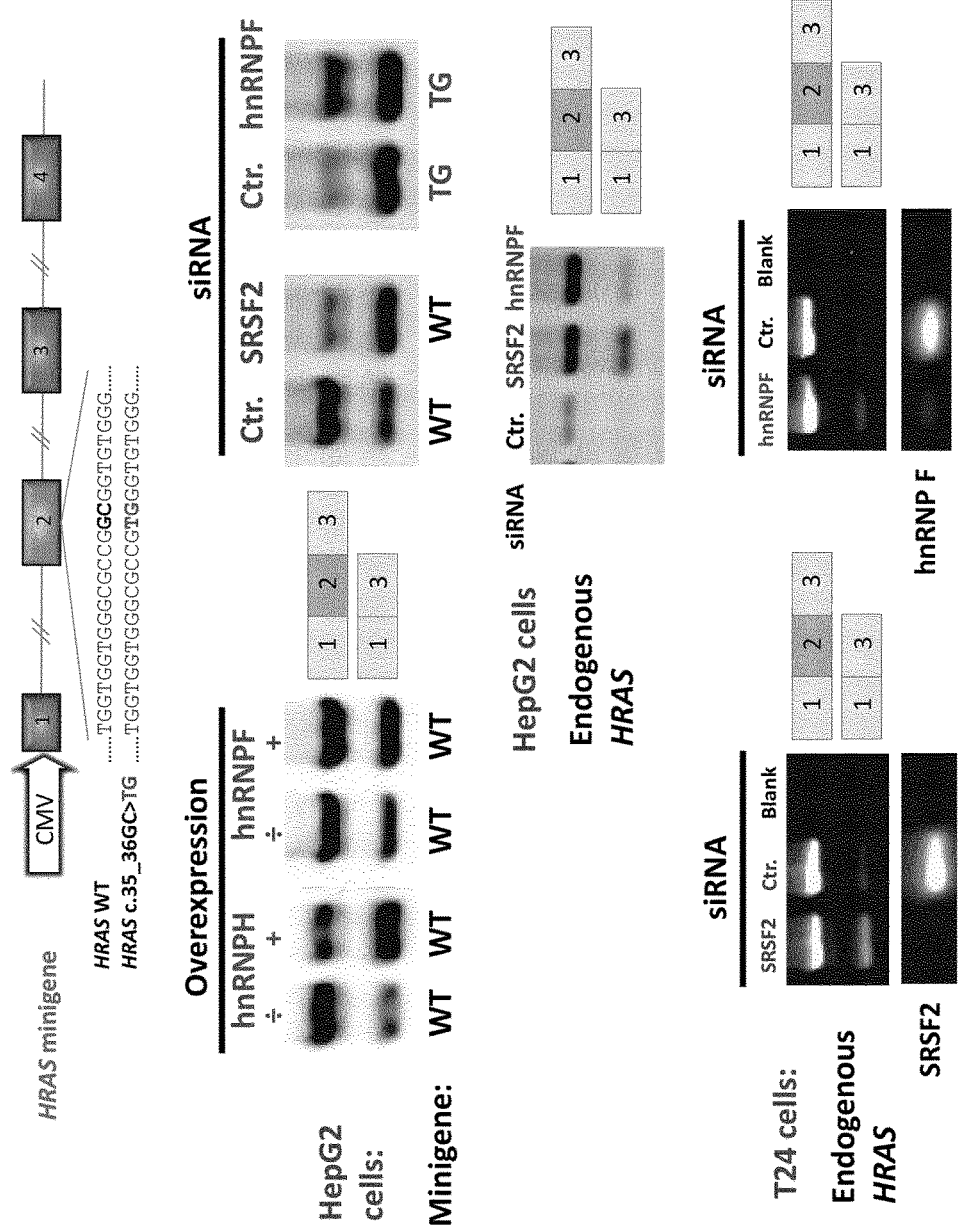

FIG. 7 shows that overexpression of hnRNPF or hnRNPH splicing inhibitors leads to exon 2 skipping from the wild type HRAS minigene in HepG2 cells. It is also demonstrated that down-regulation of SRSF2 by siRNA treatment leads to exon 2 skipping both from the HRAS minigene and from the endogenous HRAS gene in HepG2 and T24 cells. SRSF2 has been demonstrated to bind to HRAS exon 2 and is known to stimulate splicing by binding to ESEs. The results therefore show that exon 2 inclusion is dependent on binding of splicing stimulatory factors, like SRSF2 to ESEs as shown here for HepG2 and T24 cancer cells. Down-regulation of hnRNPF by siRNA treatment increases exon 2 inclusion from the TG minigene, which shows that binding of this inhibitory factor to GGG motifs in HRAS exon 2 inhibits exon inclusion. Knock down of hnRNPF and SRSF2 was performed with SmartPool siRNAs directed toward hnRNPF or SRSF2 using a siRNA-scr scrambled sequence as control (Dharmacon) according to standard protocols. 48 hours post transfection RNA was extracted, cDNA prepared and an HRAS exon 2 skipping was analyzed by PCR using either minigene specific primers or primers detecting endogenous HRAS. PCR products were analyzed by electrophoresis in an agarose gel. The transfections were performed in triplicate and the experiments repeated twice using Lipofectamine® RNAiMax. Blank: Represents a control PCR without added cDNA. Ctr.: Represent a sample transfected with a scrambled non-targeting siRNA control.

Figure 8:
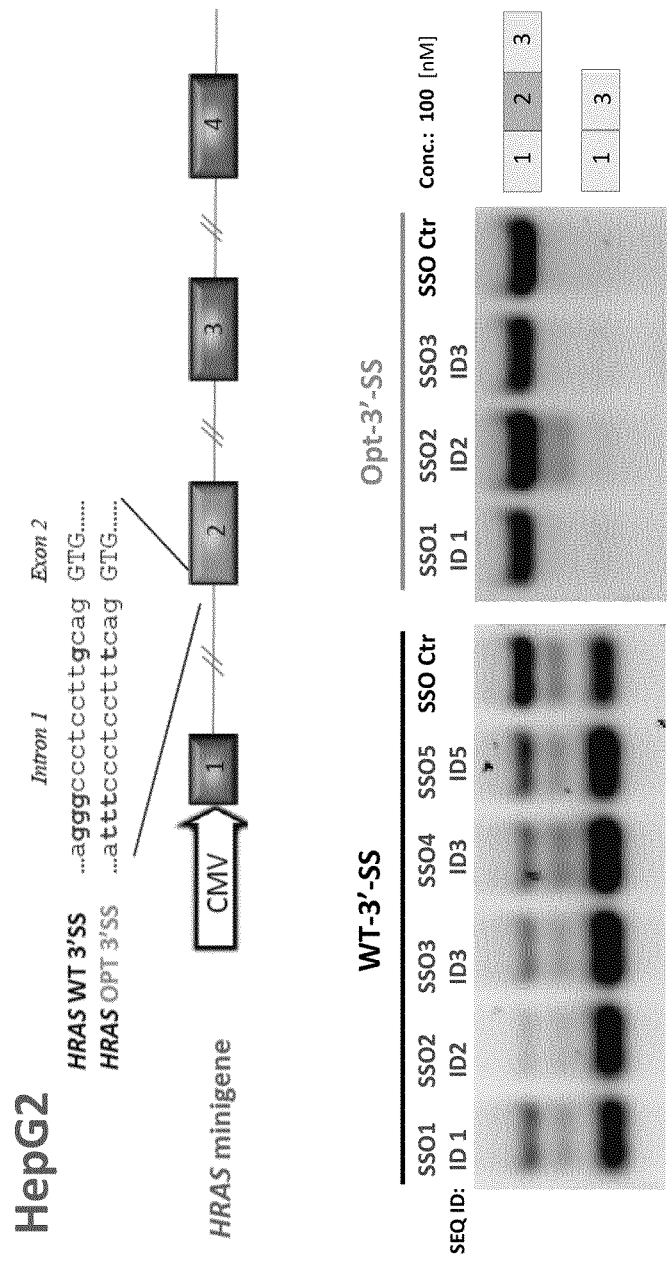

FIG. 8 shows testing of SSOs targeting HRAS using the HRAS minigene. This demonstrates that vulnerability of exon 2, due to the weakly defined splice sites, is necessary if SSO's should mediate exon 2 skipping. When the wild type HRAS minigene was transfected into HEPG2 cells we observed nearly complete skipping of exon 2 when treating with 100 nmol/l of SEQ ID NO 1, SEQ ID NO 2, SEQ ID NO 3, SEQ ID NO 4 or SEQ ID NO 5 for 48 hours. SEQ ID NO 2, SEQ ID NO 4 and SEQ ID 5, blocks access to ESE-A at position c.32-37. On the other hand, treating cells transfected with a HRAS WT minigene, where one of the splice sites is optimized according to the splice site consensus sequence, showed no HRAS exon 2 skipping. This demonstrates that vulnerability of exon 2, due to the weakly defined splice sites, is necessary if SSO's should mediate exon skipping. The level of skipping produced by each SSO at 100 nmol/l 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). 3'ss: 3' splice site, 5'ss: 5' splice.

Figures 9, 9A:
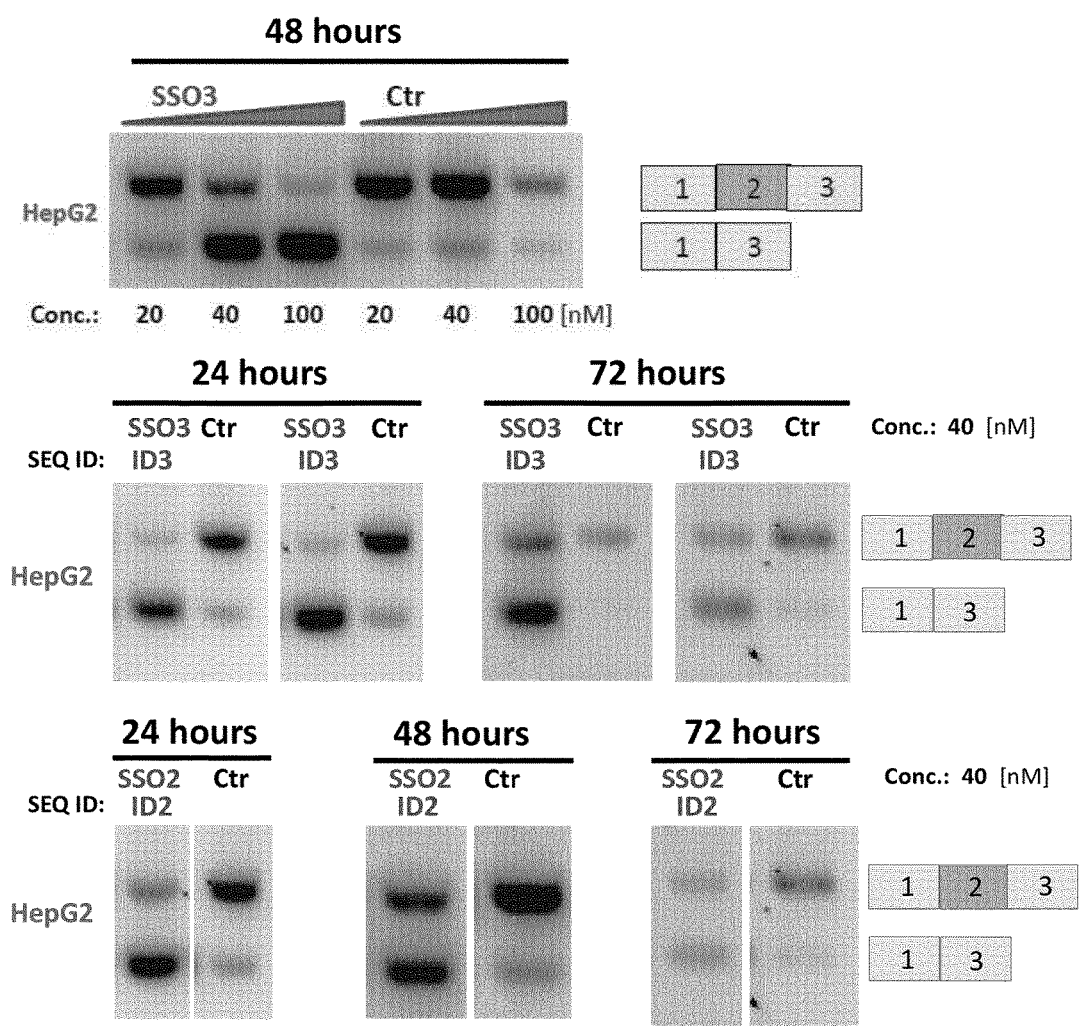

FIG. 9A shows that SSO treatment of HepG2 cancer cells induce endogenous HRAS exon 2 skipping in a SSO dose dependent manner. A dosis of 40 nmol/l is efficient and exon 2 skipping was demonstrated to persist at least 72 hours after treatment. The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42).

Figure 9B:
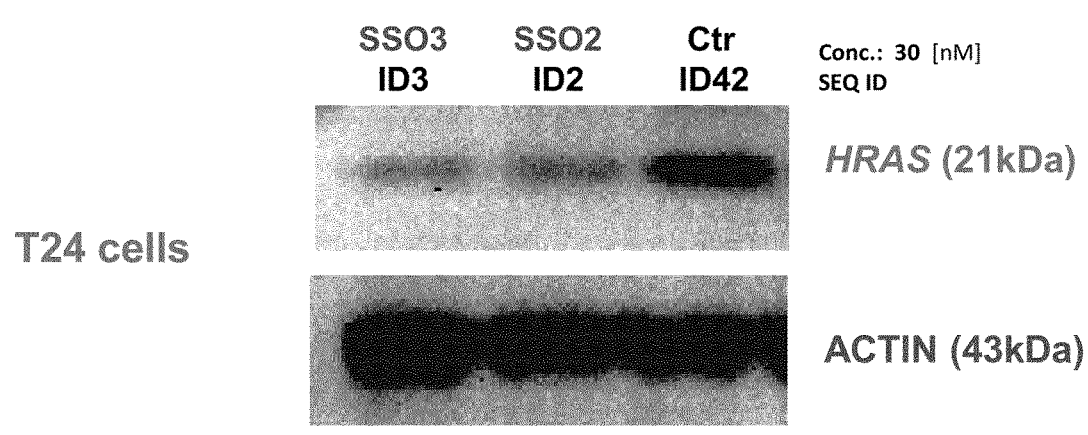

FIG. 9B shows that treatment of T24 cancer cells with SSO2 or SSO3 at a low dose of 30 nmol/l for 72 hours results in severely decreased levels of HRAS protein relative to a control protein (Actin). This shows that skipping of exon 2 caused by SSO treatment as expected abolishes production of normal HRAS protein in the cells. HRAS protein was detected using a monoclonal antibody towards HRAS (Cell Biolabs Inc.) and actin was detected by a monoclonal antibody (Abcam).

Figure 5A:
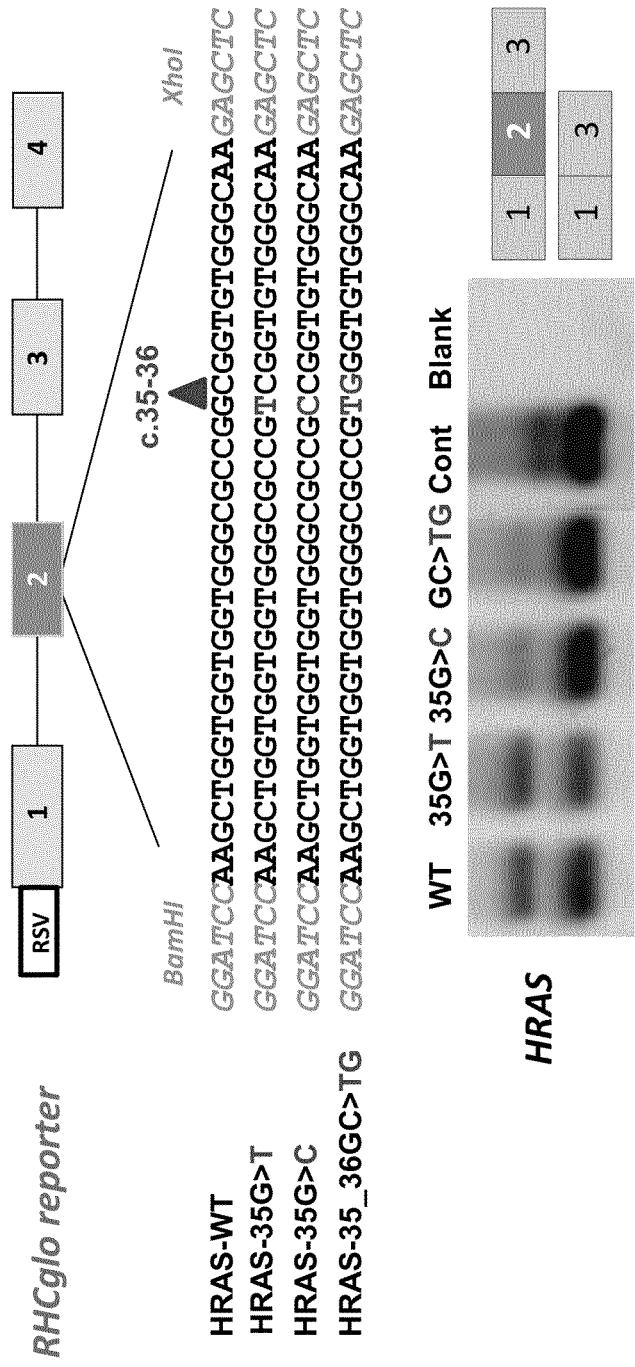
FIG. 5A shows testing of nucleotides c.13-c.47 from HRAS in a RHC-Glo splicing reporter minigene [Singh and Cooper 2006]. This confirmed the presence of at least one ESE in the tested part of HRAS exon 2, since splicing of the reporter test-exon is dependent on the presence of ESE sequences in the inserted sequence. The ESE function of the inserted sequence is disrupted by the c.35_36GC>TG mutation and by the c.35G>C (p.Gly12Ala), but strengthened by the c.35G>T (p.Gly12Val) mutation. This is consistent with the effect of these mutations when tested in the HRAS minigene and overall the results confirms that pos. c.32-37 harbors an ESE (ESE-A). The listed mutations were introduced by site directed mutagenesis into the RHC-Glo reporter minigene, which was transfected into HEK293 cells. 48 hours post transfection RNA was extracted, cDNA prepared and exon 2 skipping was analyzed by PCR. PCR products were analyzed by electrophoresis in an agarose gel. The transfections were performed in triplicate and the experiments repeated twice using Lipofectamine® RNAiMax. Blank: Represents a control PCR without added cDNA.
Figure 5B:
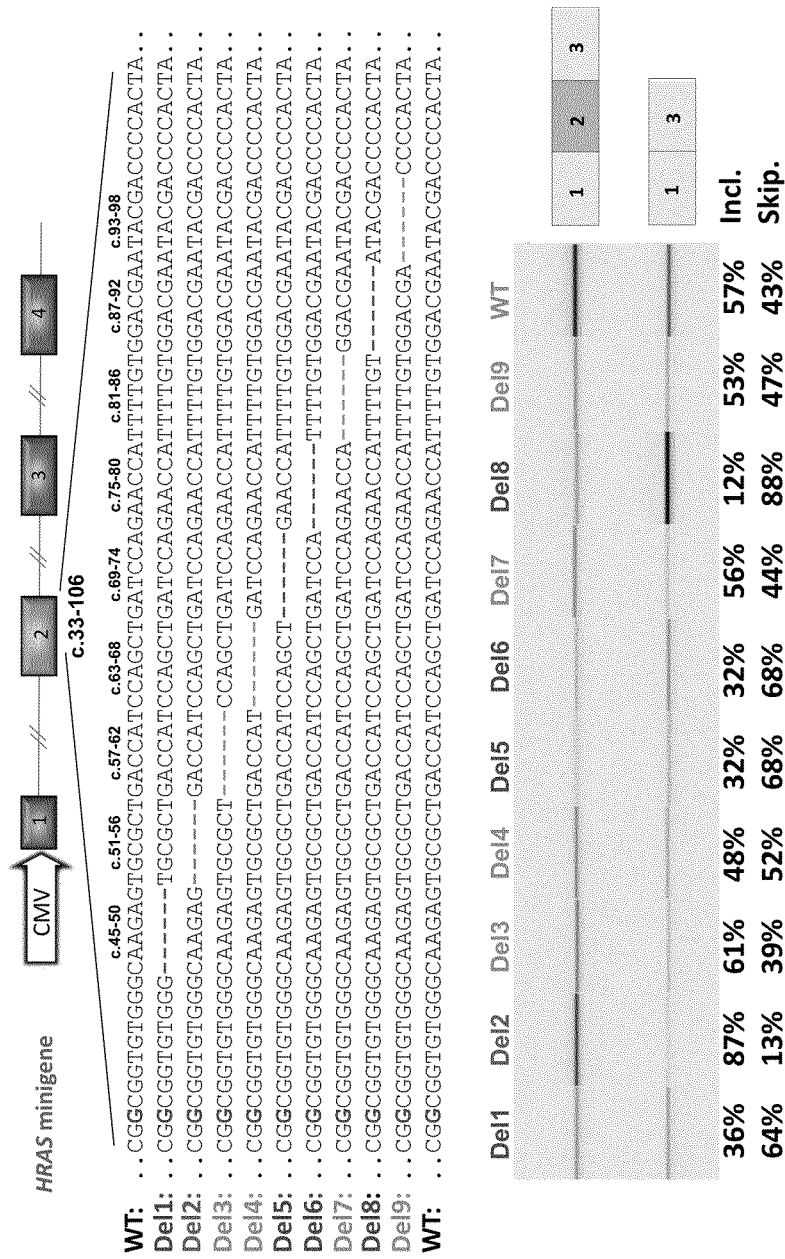
FIG. 5B shows transfection of HepG2 cancer cells using the HRAS minigene, which consist of exons 1, 2, 3 and 4 and the flanking introns. The region from c.45 to c.92 in HRAS exon 2 was investigated for splicing regulatory sequences (ESEs and ESSs) by introduction of consecutive 6 bp deletions. The listed HRAS deletions were introduced by standard site directed mutagenesis. The minigene was transfected into HepG2 cells. 48 hours post transfection RNA was extracted, cDNA prepared and HRAS exon 2 skipping was analyzed by PCR as described in materials methods. PCR products were analyzed by electrophoresis in a Fragment Analyzer™ system (Advanced Analytical). Band intensities from two experiments were used to calculate the molar ratio between bands resulting from exon 2 inclusion and exon 2 skipping. The transfections were performed using Lipofectamine® RNAiMax. Deletion analysis shows that ESE elements important for exon 2 inclusion are present in three regions defined as c.45-c.50 (ESE-B), c.69-c.80 (ESE-C) and a particularly strong ESE is present at position c.87-c.92, named ESE-D. This analysis also shows that the region from c.51-c.56 harbors a negative splicing regulatory element, ESS-A, since deletion of this sequence improves exon 2 inclusion.
Figure 10:
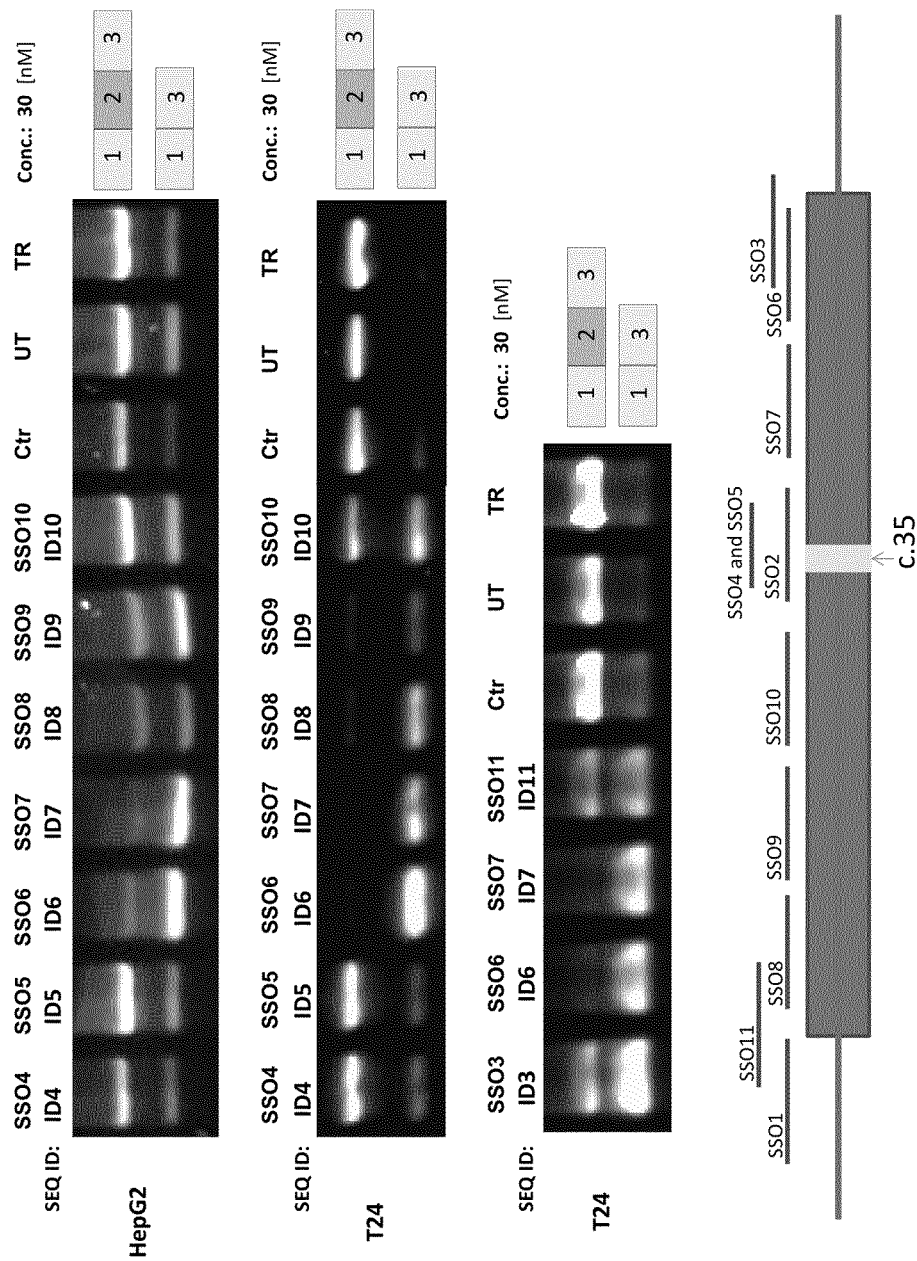

FIG. 10 shows that several of the SSOs targeting ESEs located to different sequence domains mediate endogenous HRAS exon 2 skipping at a low SSO dose of 30 nmol/l in T24 and HepG2 cancer cells. Masking of ESEs by treatment with SEQ ID NO 6 or SEQ ID NO 7 is particularly efficient in inducing exon 2 skipping. This is consistent with the fact that SEQ ID NO 6 blocks binding of splicing stimulatory proteins to the very strong ESE-D (FIG. 5B) and that SEQ ID NO 7 blocks binding of splicing stimulatory proteins to ESE-C (FIG. 5B). The lower potency of SEQ ID NO 2, 4 and 5 for inducing exon 2 skipping may be due to the fact that in addition to blocking access to the ESE-A, present at position c.32-c.37 they simultaneously block access to the negative ESS-A present at position c.51-56. Blocking access to the splice sites by SEQ ID NO 3 or SEQ ID NO 11 also induces significant exon 2 skipping. A schematic drawing indicates the relative target position of the SSOs in HRAS exon 2 and the position of c.35 in codon 12 is also indicated. The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

Figure 11:
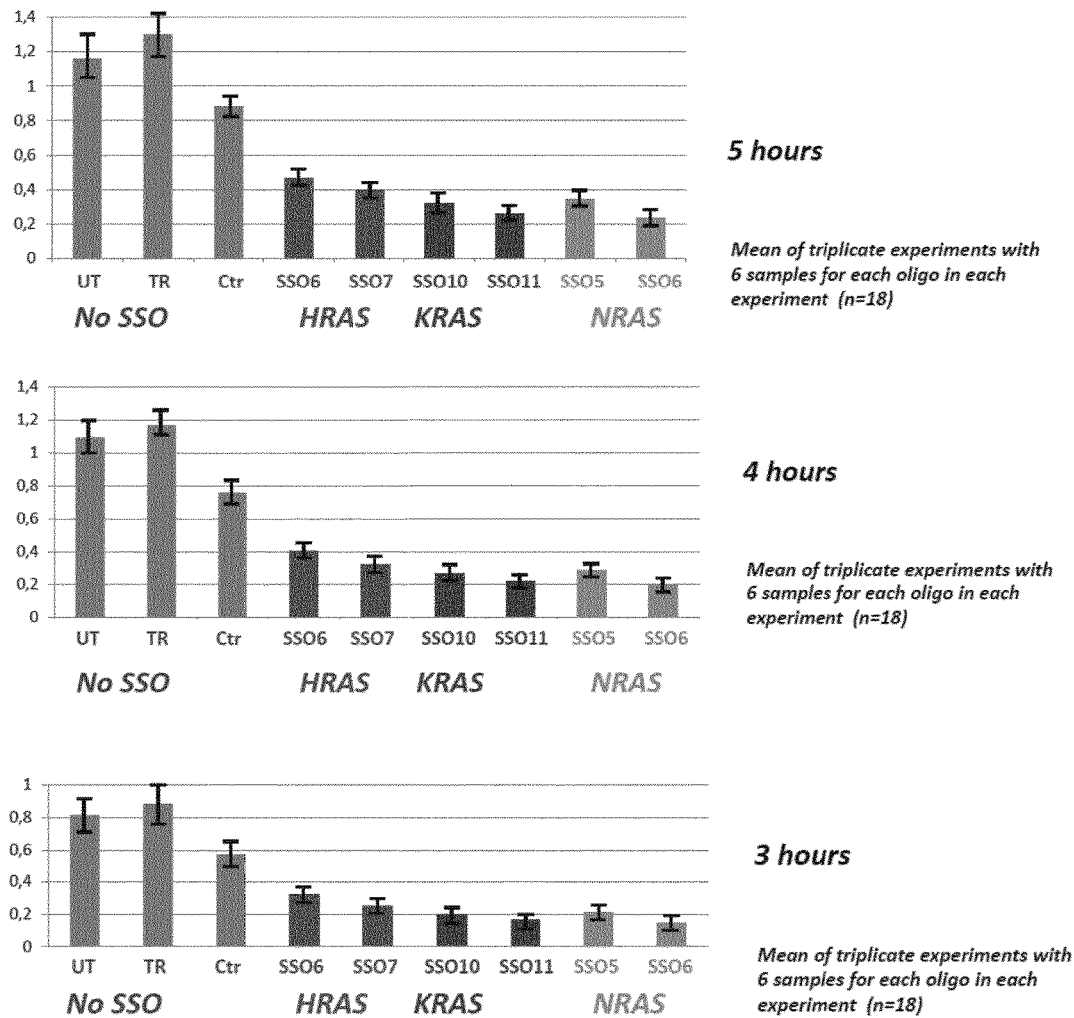

FIG. 11 shows that treatment of T24 cancer cells with a low SSO dose of 30 nmol/l of the most efficient SSOs targeting either HRAS exon 2 (SSO 6 or SSO7), or KRAS exon 2 (SSO 10 or SSO11), or NRAS exon 2 (SSO 5 or SSO6) leads to dramatically reduced growth and proliferations as assessed by WST-1 assay at three different time points. The results are shown as mean of triplicate experiments with six samples tested for each SSO. Error bars indicate standard deviations of the mean. The transfections were performed using Lipofectamine® RNAiMax.

Ctr.: Represent a sample transfected with a scrambled non-targeting SSO (SEQ ID NO 42). UT is untreated cells. TR are cells treated with the transfection reagent alone.

Figure 12:
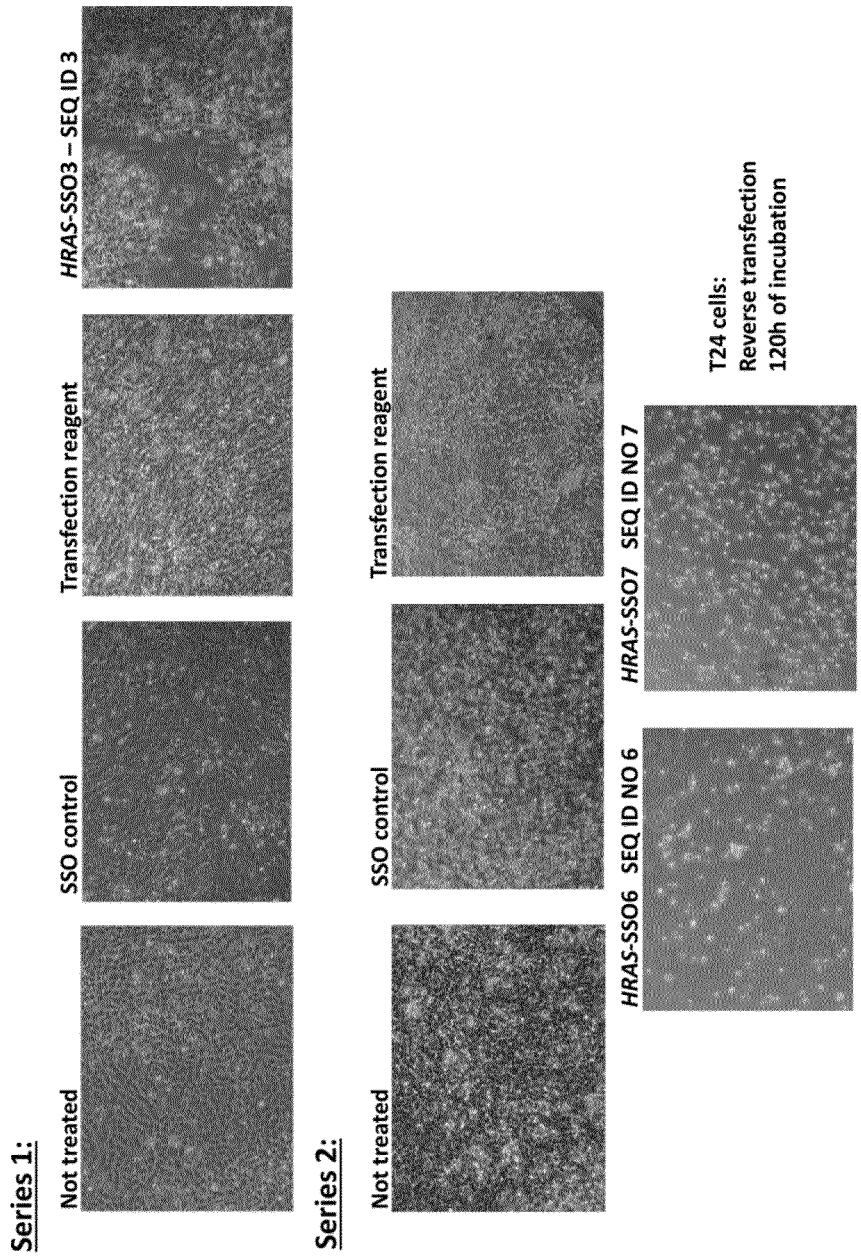

FIG. 12 shows that treatment of T24 cancer cells with a low SSO dose of 30 nmol/l of the most efficient SSOs targeting the conserved region of HRAS exon 2 (SSO 6 or SSO7) leads to pronounced cell death at 120 hours post transfection as observed by representative pictures from phase contrast microscopy. Treatment with SSO-3 that target the 3'-splice site of HRAS exon 2 also leads to cell death at 120 hours post transfection as observed by phase contrast microscopy. Pictures of a sample transfected with a scrambled non-targeting SSO (SEQ ID NO 42) untreated cells or cells treated with the transfection reagent alone are also shown.

Figure 13:
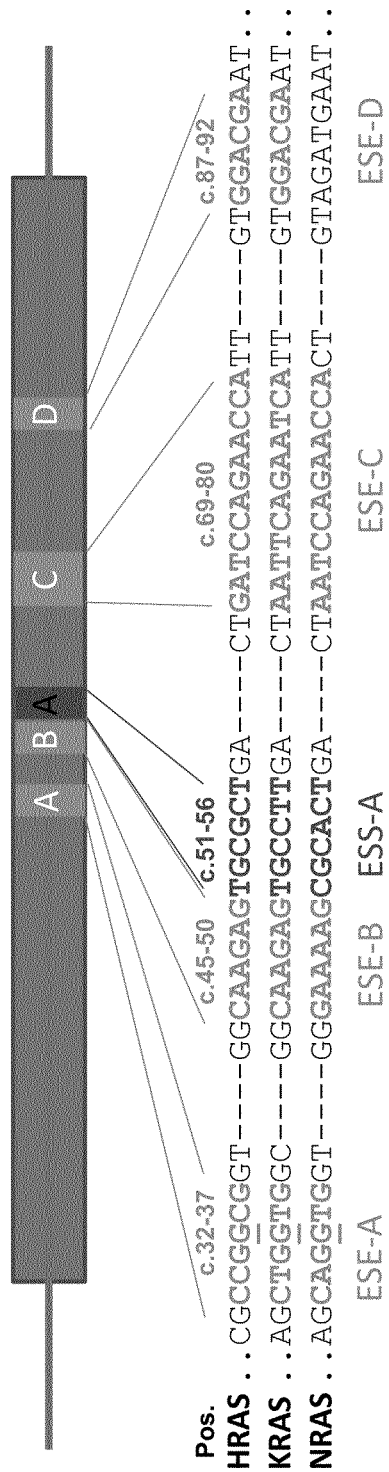

FIG. 13: Pairwise alignments of the sequences from HRAS exon 2, KRAS exon 2 and NRAS exon 2 using BLAST algorithm (http://blast.ncbi.nlm.nih.gov/Blast.cgi) shows that a 113 nucleotides long proportion of exon 2 starting at the translation initiation codon (Position c.1-c.111 in NM_001130442.1, NM_005343.2, NM_176795.3, NM_004985.3, NM_033360.2 and NM_002524.4) exhibits more than 80% identical nucleotides. Therefore many crucial splicing regulatory elements, like ESEs, located in this region are conserved between the three RAS genes. It is therefore likely that blocking access to conserved ESEs in this region is also responsive to SSO-mediated skipping in KRAS exon 2 and NRAS exon 2.

The sequences of the functional ESEs ESE-A to ESE-C and ESS-A from the three RAS genes are displayed with numbering according to the reference cDNA sequences.

ESE-A (pos c.32-c.37) is not conserved in KRAS and NRAS.

ESE-B (pos c.45-c.50) and 2 flanking upstream nucleotides and three flanking downstream nucleotides is completely conserved in KRAS, whereas the first nucleotide (c.45C) in ESE-B is replaced with a c.45G in NRAS.

ESE-C: Position c.73-c.80 of this ESE is conserved between the three genes, with position c.78 being a T in KRAS. Position c.73-c.80 of ESE-C is therefore defined as the core of this ESE.

ESE-D (c.87-c.92) and two flanking nucleotides upstream and downstream are completely conserved between HRAS and KRAS, but not in NRAS.

Figure 14:
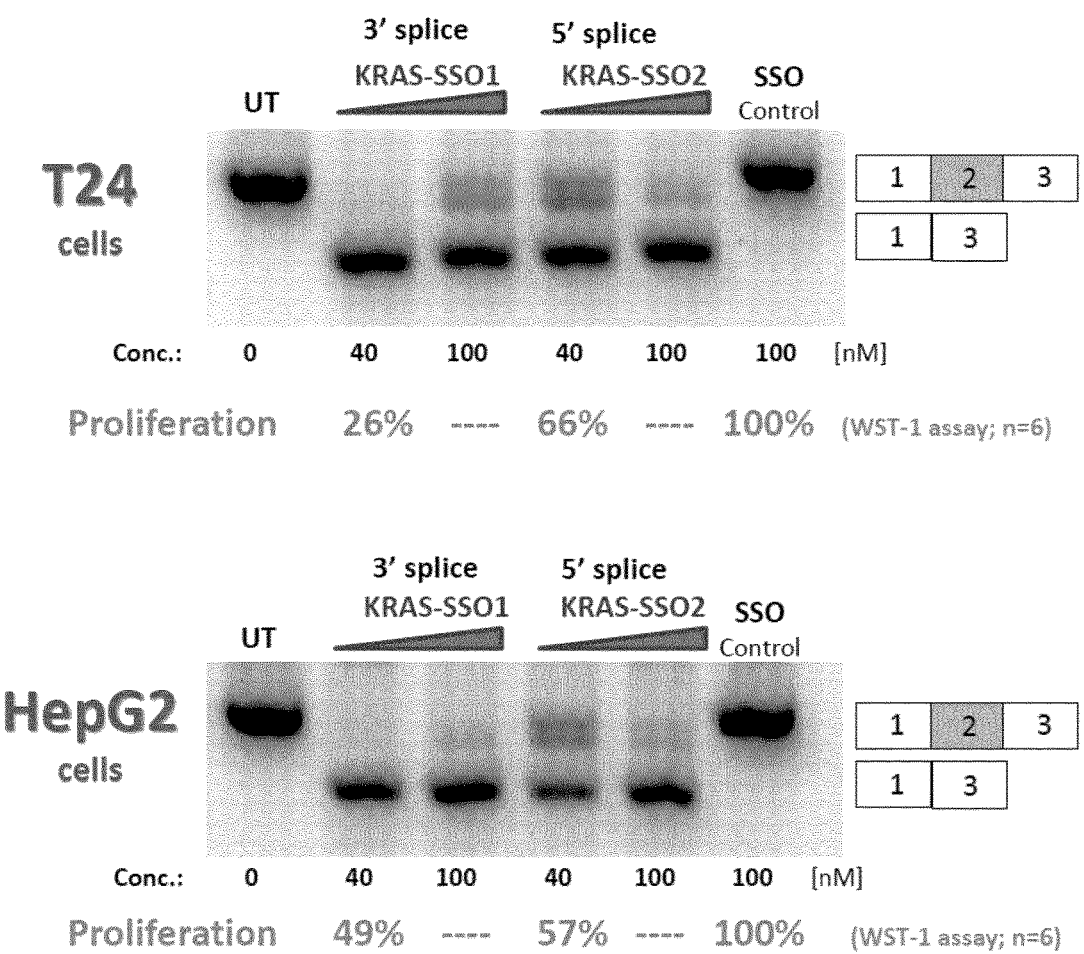

FIG. 14 shows that SSO treatment of T24 and HepG2 cancer cells induce endogenous KRAS exon 2 skipping in a SSO dose dependent manner. A dose of 40 nmol/l is efficient. The level of skipping produced by each SSO 48 hours after treatment was determined by PCR. PCR products were analyzed by electrophoresis in an agarose gel. It is also shown that both KRAS SSO-1 (SEQ ID NO 12) and KRAS SSO2 (SEQ ID 13) leads to reduced growth and proliferation of both T24 cancer cells and HepG2 cancer cells, as assessed by WST-1 assay. The results are shown as percent of cells treated with the scrambled control oligo (SEQ ID NO 42) and are means of six samples. Treatment with KRAS SSO-1 induces more exon 2 skipping than KRAS SSO2 and this is reflected by a more reduced proliferation and growth of cells treated with KRAS SSO 1. The transfections were performed using Lipofectamine® RNAiMax. Ctr.: Represent a sample transfected with a scrambled non-targeting SSO (SEQ ID NO 42).

Figure 15:
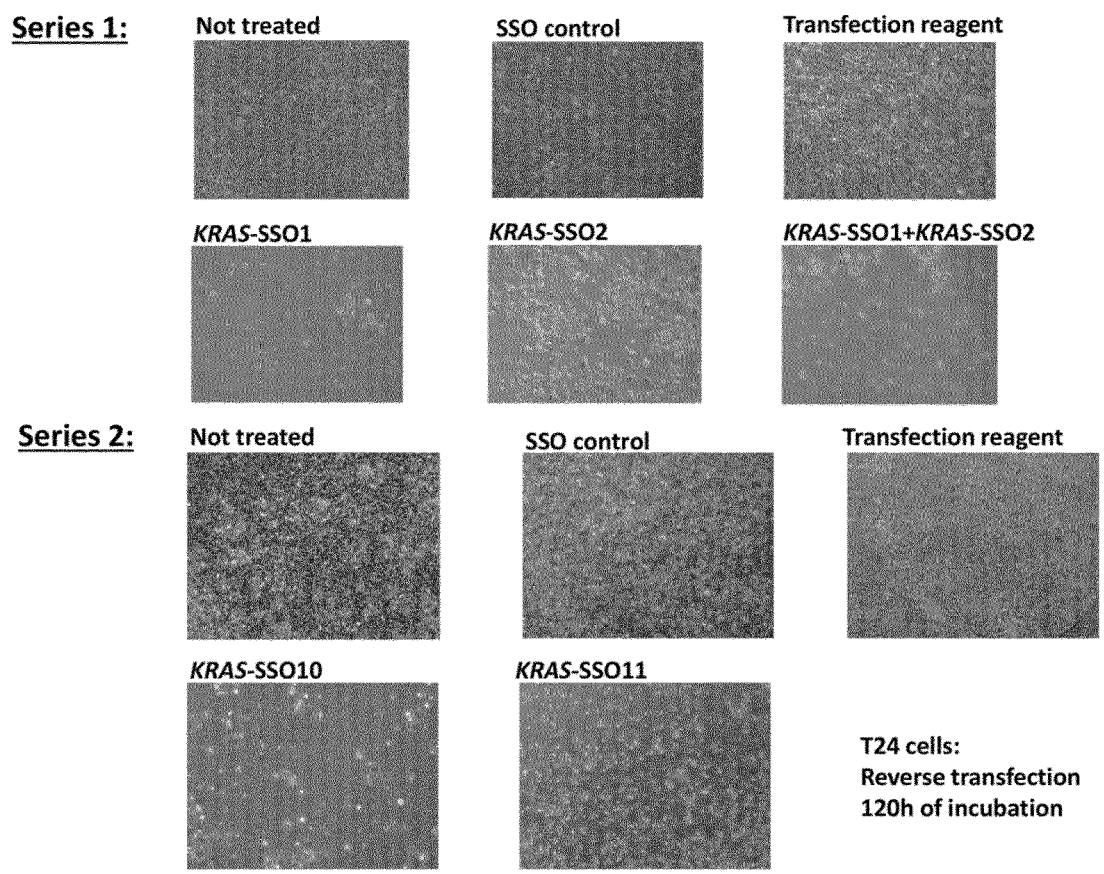

FIG. 15 shows that treatment of T24 cancer cells with a low SSO dose of 30 nmol/l of the most efficient SSOs targeting the conserved region of KRAS exon 2, SEQ ID NO 21 (SSO-10) and SEQ ID NO 22 (SSO-11) leads to pronounced cell death at 120 hours post transfection as observed by representative pictures from phase contrast microscopy. Treatment with SEQ ID NO 12 (SSO-1) or SEQ ID NO 13 (SSO-2) that target the splice sites of KRAS exon 2 also leads to cell death at 120 hours. Pictures of a sample transfected with a scrambled non-targeting SSO (SEQ ID NO 42) untreated cells or cells treated with the transfection reagent alone are also shown.

Figure 16:
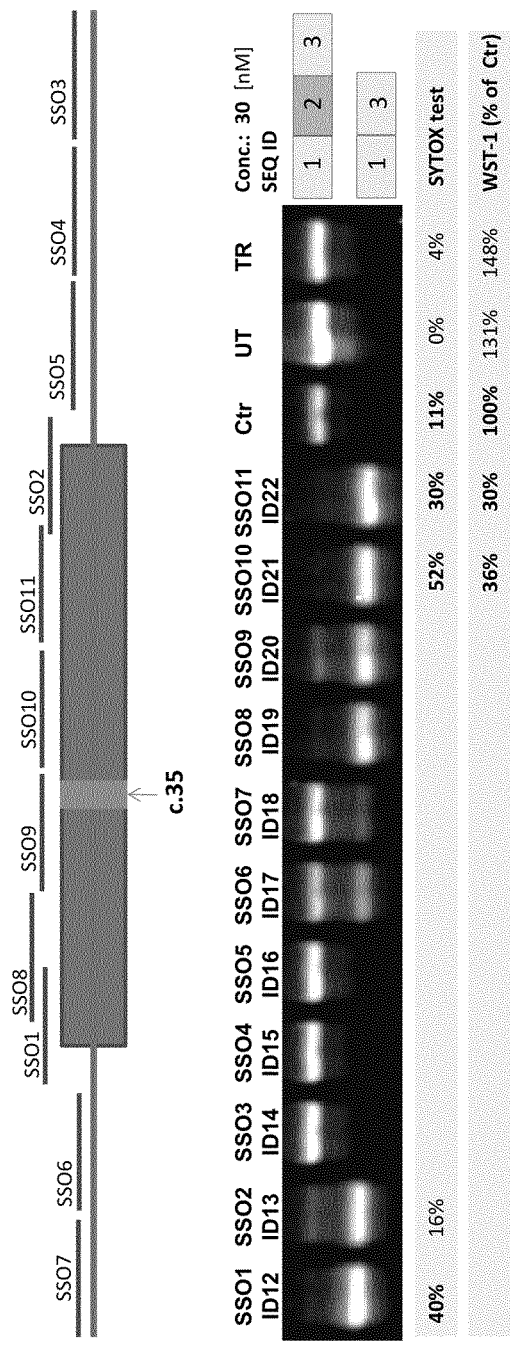

FIG. 16 shows that several of the SSOs targeting ESEs located to different sequence domains mediate endogenous KRAS exon 2 skipping at a low SSO dose of 30 nmol/l in T24 cancer cells. Blocking access to ESEs in the conserved region by treatment with SEQ ID NO 21 or SEQ ID NO 22, is particularly efficient in inducing exon 2 skipping.

SEQ ID NO 21 covers the sequence homologous to ESE-B in HRAS and is therefore particularly efficient in inducing exon 2 skipping. Blocking of both ESE-C and ESE-D by treatment with SEQ ID NO 22, is particularly efficient in inducing exon 2 skipping.

Treatment with a low dose of KRAS SSO-1 (SEQ ID NO 12) and KRAS SSO2 (SEQ ID 13), which target the splice sites also results in exon skipping with KRAS SSO-1 (SEQ ID NO 12) being the most efficient of these two.

Parallel results from a SYTOX test are shown and demonstrate that SEQ ID NO 12, SEQ ID NO 13, SEQ ID NO 21 and SEQ ID NO 22 leads to cell death as indicated by uptake of SYTOX green. The values represent increase in uptake in percent of uptake by untreated cells (UT). The SYTOX test shows that SEQ ID NO 12, SEQ ID NO 21 and SEQ ID NO 22 are most effective in inducing death, consistent with the observed cell death by phase contrast microscopy (FIG. 15) and the levels of exon 2 skipping measured by PCR. Results from the WST-1 assay given as percent of untreated cells is also shown for some of the samples. A schematic drawing indicates the relative target position of the SSOs in KRAS exon 2 and the position of c35 in codon 12 is also indicated. The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

Figure 17:
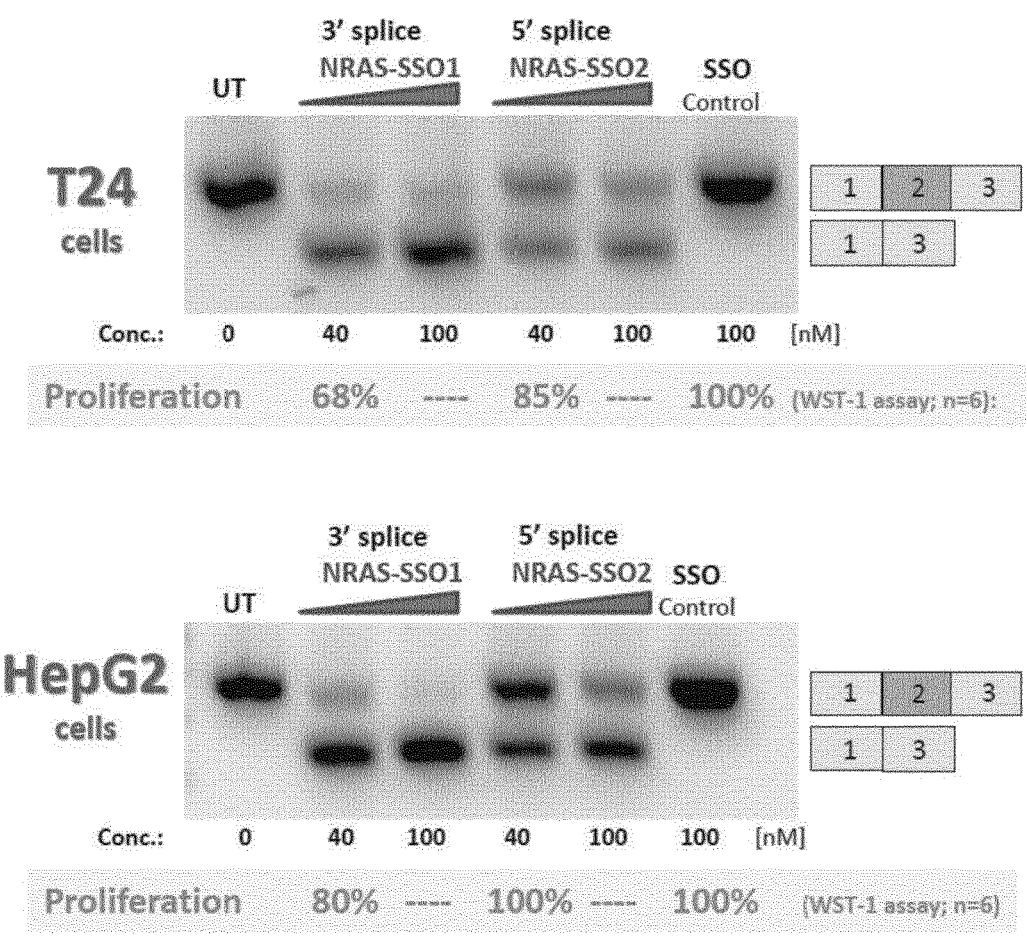

FIG. 17 shows that SSO treatment of T24 and HepG2 cancer cells induce endogenous NRAS exon 2 skipping in a SSO dose dependent manner. A dose of 40 nmol/l is efficient for NRAS SSO-1 (SEQ ID NO 23), but NRAS SSO2 (SEQ ID 24) requires 100 nmol/l to induce complete exon 2 skipping. The level of skipping produced by each SSO 48 hours after treatment was determined by PCR. PCR products were analyzed by electrophoresis in an agarose gel. It is also shown that both NRAS SSO-1 (SEQ ID NO 23) and NRAS SSO2 (SEQ ID 24) leads to reduced growth and proliferation of T24 cancer cells although the effect of NRAS SSO2 (SEQ ID 24) is limited in HepG2 cancer cells, as assessed by WST-1 assay. The results from the WTS-1 assay are shown as percent of cells treated with the scrambled control oligo (SEQ ID NO 42) and are means of six samples. Treatment with NRAS SSO-1 induces more exon 2 skipping than NRAS SSO2 and this is reflected by a more reduced proliferation and growth of cells treated with NRAS SSO 1. The transfections were performed using Lipofectamine® RNAiMax. Ctr.: Represent a sample transfected with a scrambled non-targeting SSO (SEQ ID NO 42).

Figure 18:
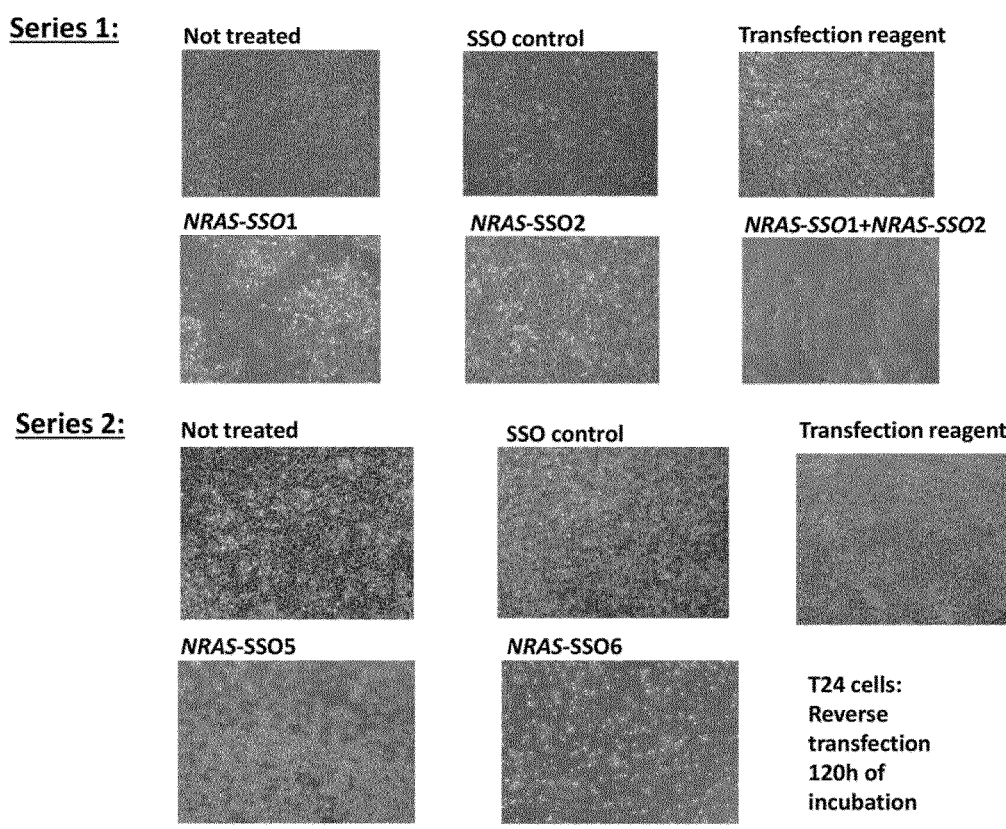

FIG. 18 shows that treatment of T24 cancer cells with a low SSO dose of 30 nmol/l of the most efficient SSOs targeting the conserved region of NRAS exon 2, SEQ ID NO 27 (SSO-5) and SEQ ID NO 28 (SSO-6) leads to pronounced cell death at 120 hours post transfection as observed by representative pictures from phase contrast microscopy. Treatment with SEQ ID NO 23 (SSO-1) that target the 3'-splice sites of NRAS exon 2 also leads to cell death at 120 hours. Pictures of a sample transfected with a scrambled non-targeting SSO (SEQ ID NO 42) untreated cells or cells treated with the transfection reagent alone are also shown.

Figure 19:
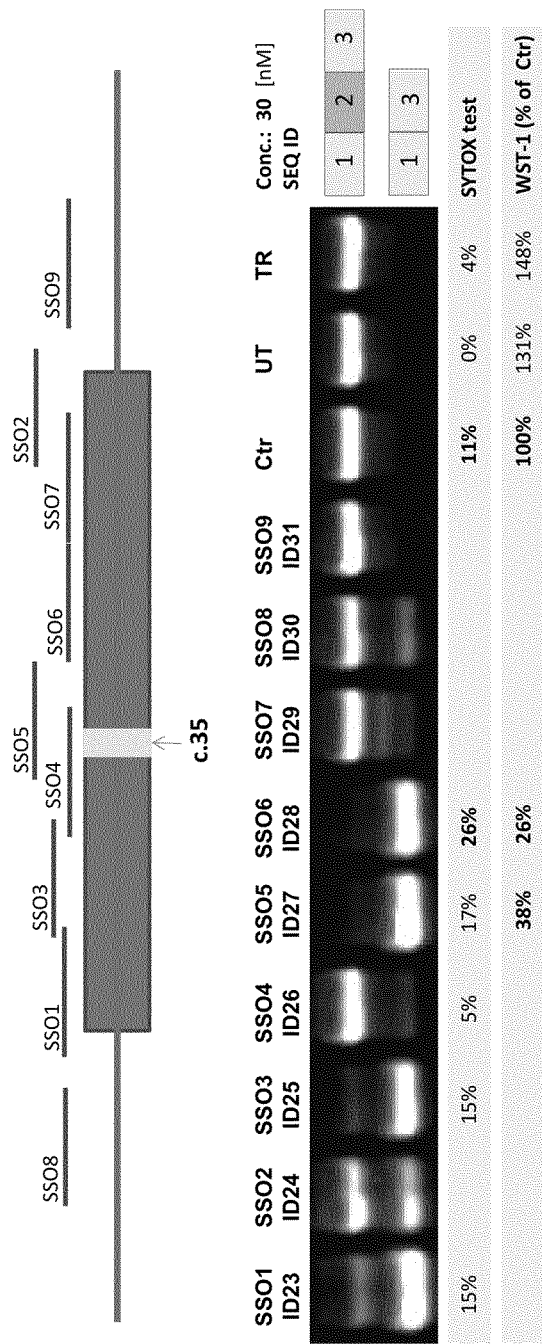

FIG. 19 shows that several of the SSOs targeting ESEs located to different sequence domains mediate endogenous NRAS exon 2 skipping at a low SSO dose of 30 nmol/l in T24 cancer cells. SEQ ID NO 27, which covers the sequence homologous to ESE-B in HRAS and KRAS is also efficient in inducing exon 2 skipping. Blocking of ESE-C by treatment with SEQ ID NO 28, is efficient in inducing exon 2 skipping. Blocking of ESE-D by treatment with SEQ ID NO 29, does cause exon 2 skipping, since the element is not conserved in NRAS. Treatment with a low dose of NRAS SSO-1 (SEQ ID NO 23) and NRAS SSO2 (SEQ ID 24), which target the splice sites also results in exon skipping with NRAS SSO-1 (SEQ ID NO 23) being the most efficient of these two. Parallel results from a SYTOX test are shown and demonstrate that SEQ ID NO 27 and SEQ ID NO 28 leads to cell death as indicated by uptake of SYTOX green. The values represent increase in uptake in percent of uptake by untreated cells (UT). The SYTOX test is consistent with the observed cell death by phase contrast microscopy (FIG. 18) and the levels of exon 2 skipping measured by PCR. Results from the WST-1 assay given as percent of untreated cells are also shown for some of the samples. A schematic drawing indicates the relative target position of the SSOs in NRAS exon 2 and the position of c.35 in codon 12 is also indicated. The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

Figure 20:
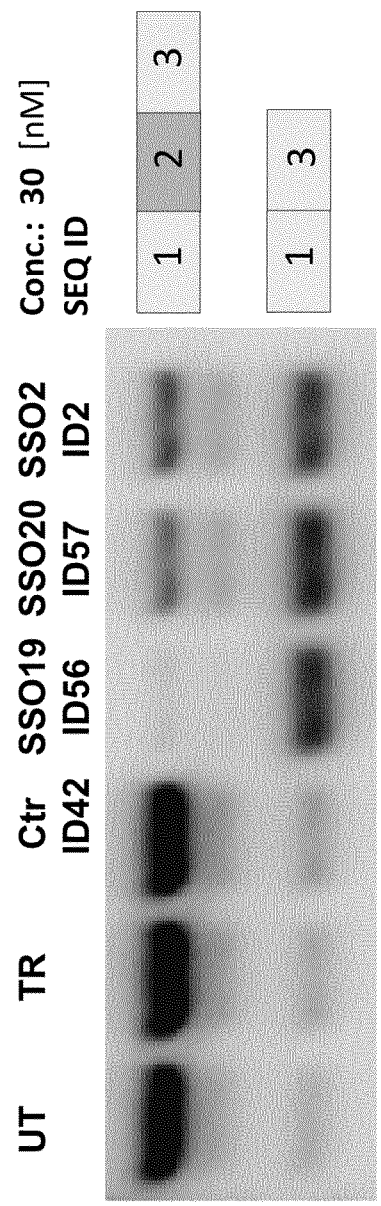

FIG. 20 shows that SSO19 (SEQ ID NO 56), which simultaneously blocks access to both ESE-C and ESE-D is particularly efficient in inducing HRAS exon 2 skipping at a low SSO dose of 30 nmol/l in T24 cancer cells. SSO20 (SEQ ID NO 57), which is 5 nt. shorter than SSO-19, but still blocks access to ESE-D and part of ESE-C is also efficient in mediating exon 2 skipping. The level of skipping produced by each SSO 72 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

Figure 21:
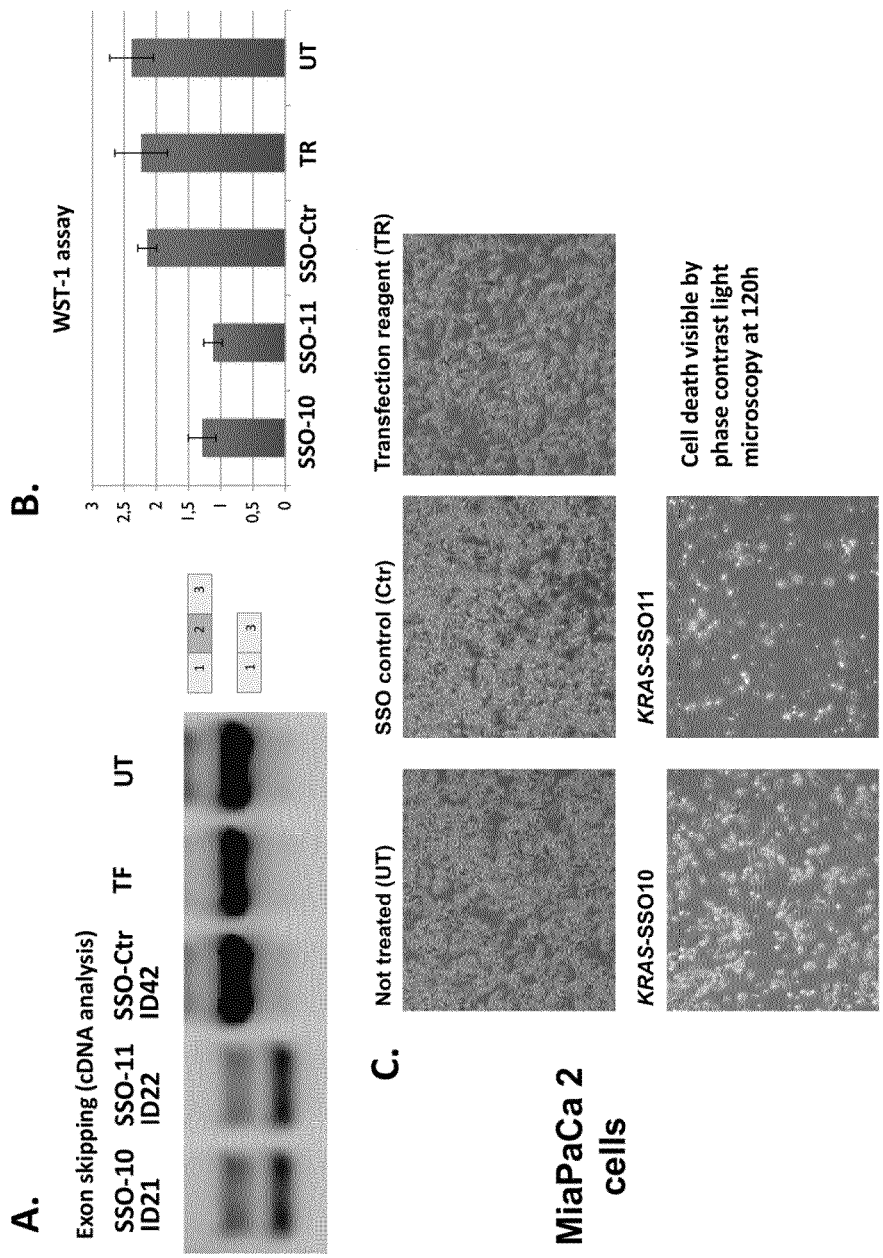

FIG. 21. Part A shows that treatment of pancreatic cancer cells (MiaPaCa-2) with SEQ ID NO 21 or SEQ ID NO 22 at a low SSO dose of 30 nmol/l mediate endogenous KRAS exon 2 skipping. Part B shows that treatment of pancreatic cancer cells (MiaPaCa-2) with SEQ ID NO 21 or SEQ ID NO 22 at a low SSO dose of 30 nmol/l results in significant reduced growth and proliferation when assayed by a WST-1 assay. Part C shows that treatment of pancreatic cancer cells (MiaPaCa-2) with SEQ ID NO 21 or SEQ ID NO 22 at a low SSO dose of 30 nmol/l results in significant cell death observed by phase contrast microscopy. Results from the WST-1 assay is given as percent of untreated cells The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

Figure 22:
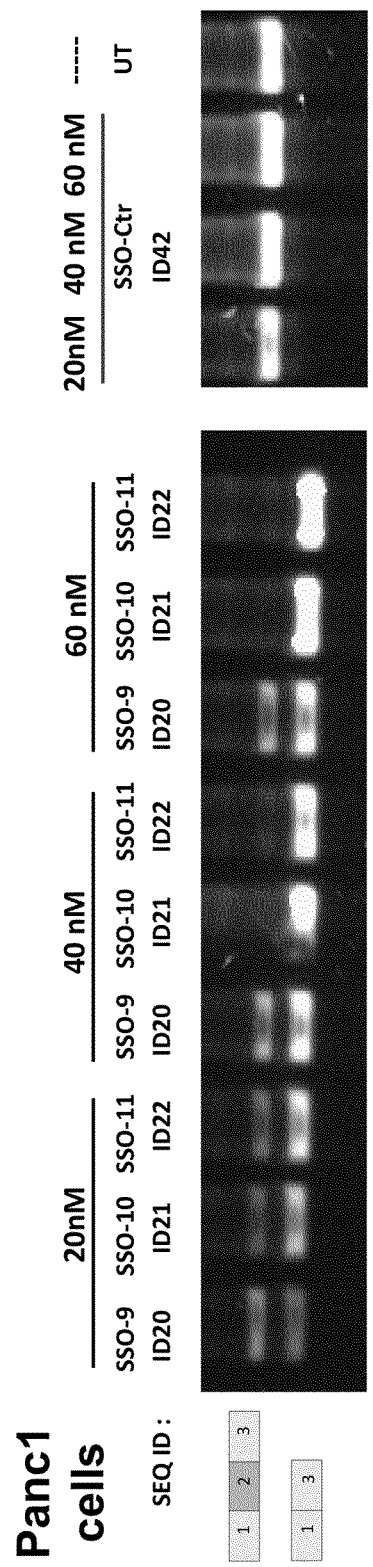

FIG. 22 shows that treatment of pancreatic cancer cells (Panc-1) with SEQ ID NO 20, SEQ ID NO 21 or SEQ ID NO 22 mediate endogenous KRAS exon 2 skipping and that this is dose dependent. Treatment with SEQ ID NO 21 or SEQ ID NO 22 is more efficient in inducing exon skipping than treatment with SEQ ID NO 20. The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

Figure 23:
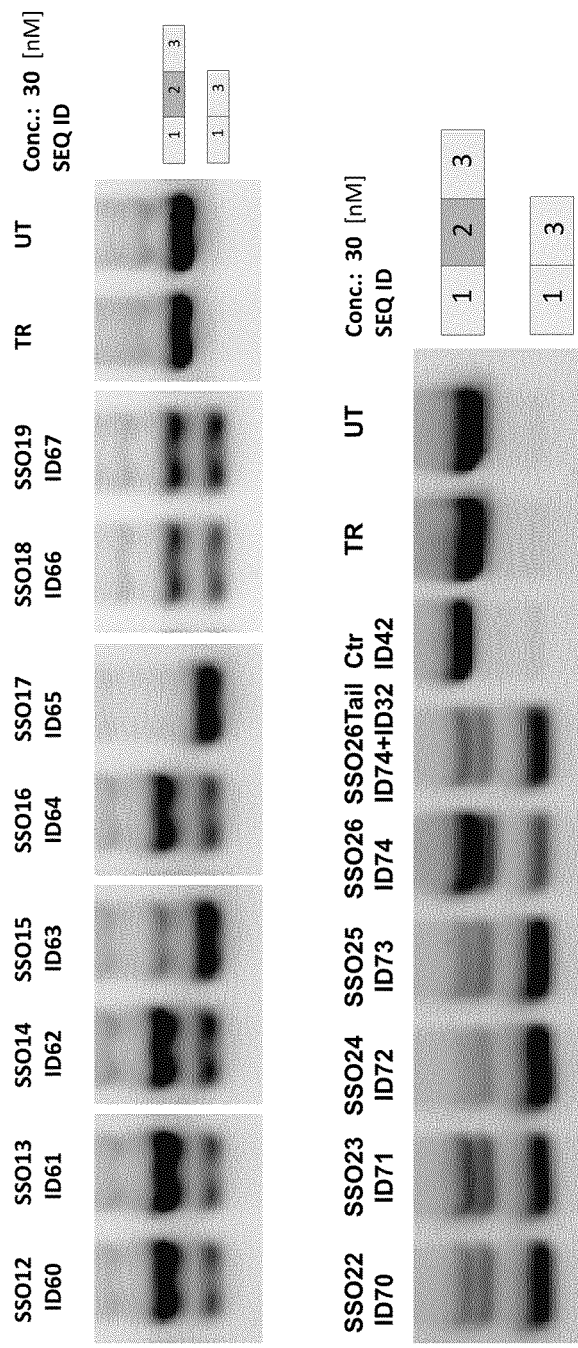

FIG. 23 shows that the efficiency of inducing KRAS exon 2 skipping differs between several SSOs, which all block access to ESE-B when using a low SSO dose of 30 nmol/l in MiaPaCa-2 pancreatic cancer cells. Blocking access to ESE-B by treatment with SEQ ID NO 63, SEQ ID NO 65 or SEQ ID NO 72, is particularly efficient in inducing KRAS exon 2 skipping.

This figure also shows that addition of tail sequence (SEQ ID NO 32) to an SSO (SEQ ID NO 74) that is relatively inefficient in causing KRAS exon 2 skipping dramatically increases its potency. Because the tail sequence (SEQ ID NO 32) harbors binding sites for hnRNPF/H family of splicing repressors this also shows that binding of these negative splicing regulatory proteins to a tail sequence of an SSO bound to KRAS exon 2 in the pre-mRNA increases exon 2 skipping.

The level of skipping produced by each SSO 48 hours after treatment was determined by PCR. PCR products were analyzed by electrophoresis in an agarose gel. The transfections were performed in triplicate and the experiments repeated twice using Lipofectamine® RNAiMax. Ctr.: Represent a sample transfected with a scrambled non-targeting SSO (SEQ ID NO 42). UT is untreated cells. TR are cells treated with the transfection reagent alone.

DETAILED DESCRIPTION OF THE INVENTION

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21st edition, 2005; "Antisense Drug Technology, Principles, Strategies, and Applications" Edited by Stanley T. Crooke, CRC Press, Boca Raton, Fla.; and Green and Sambrook, "Molecular Cloning, A laboratory Manual," 4th Edition, Cold Spring Harbor Laboratory Press, 2012, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "HRAS Transcript" means a transcript transcribed from a HRAS Gene. As used herein, "HRAS Gene" means GENBANK Accession No. NC_000011.9.

As used herein, "KRAS Transcript" means a transcript transcribed from a KRAS Gene. As used herein, "KRAS Gene" means GENBANK Accession No. NC_000012.11

As used herein, "NRAS Transcript" means a transcript transcribed from a NRAS Gene. As used herein, "NRAS Gene" means GENBANK Accession No. NC_000001.10.

As used herein, the terms "Exonic Splicing Enhancer" or "Exon Splicing Enhancer" or "ESE" means a nucleotide sequence, which when present in the exon and accessible for binding of nuclear splicing regulatory proteins and/or by forming a secondary structure or a part thereof of the pre-mRNA stimulates inclusion of this exon into the final spliced mRNA during pre-mRNA splicing.

As used herein, the terms "Exonic Splicing Silencer" or "Exon Splicing Silencer" or "ESS" means a nucleotide sequence, which when present in the exon and accessible for binding of nuclear splicing regulatory proteins and/or by forming a secondary structure or a part thereof of the pre-mRNA inhibits inclusion of this exon into the final spliced mRNA during pre-mRNA splicing.

In one embodiment, an ESE or an ESS is 6-12 nucleotides in length.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e., no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "constrained ethyl nucleoside" or "cEt" means a nucleoside comprising a bicyclic sugar moiety comprising a 4'-CH(CH3)-0-2' bridge.

As used herein, "locked nucleic acid nucleoside" or "LNA" means a nucleoside comprising a bicyclic sugar moiety comprising a 4'-CH2-0-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein, "terminal group" means one or more atoms attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "splice shifting oligonucleotide" or "SSO" means a compound comprising or consisting of an oligonucleotide at least a portion of which is complementary to a target nucleic acid to which it is capable of hybridizing, resulting in at least one change in the splicing pattern of the targeted pre-mRNA.

As used herein, "a change in the splicing pattern of the targeted pre-mRNA" means a change in the pre-mRNA splicing process resulting in deletion of a proportion, for instance corresponding to an exon or a proportion thereof, from the produced mRNA when compared to the reference nucleotide sequence of the targeted pre-mRNA.

As used herein, "a change in the splicing pattern of the targeted pre-mRNA" means a change in the pre-mRNA splicing process resulting in insertion of a proportion, for instance corresponding to an intron or a proportion thereof, into the produced mRNA when compared to the reference nucleotide sequence of the targeted pre-mRNA.

As used herein, "target nucleic acid" means a nucleic acid molecule to which an SSO hybridizes.

As used herein, "mRNA" means an RNA molecule that encodes a protein.

As used herein, "pre-mRNA" means an RNA transcript that has not been fully processed into mRNA. Pre-RNA includes one or more introns.

As used herein, "transcript" means an RNA molecule transcribed from DNA. Transcripts include, but are not limited to mRNA, pre-mRNA, and partially processed RNA.

As used herein, "targeting" or "targeted to" means the association of an SSO to a particular target nucleic acid molecule or a particular region of a target nucleic acid molecule. An SSO targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an SSO that is capable of base pairing with a nucleobase of its target nucleic acid. For example, if a nucleobase at a certain position of an SSO is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an SSO and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

Embodiments

1. A splice shifting oligonucleotide (SSO) consisting of linked nucleosides comprising (i) consisting of 10 to 25 linked nucleosides having a nucleobase sequence comprising from 1 to 12 contiguous nucleobases complementary to a target region of equal length of a nucleic acid sequence harbouring a splicing regulatory sequence of 6-12 nucleotides comprised in the sequences selected from the list consisting of SEQ ID NO: 76 (HRAS Exon 2+flanking sequences), a nucleic acid sequence having at least 80% sequence identity to SEQ ID NO: 76, a nucleic acid sequence having 1 or 2 substitutions when compared to SEQ ID NO 76, SEQ ID NO: 77 (KRAS Exon 2+flanking sequences), and a nucleic acid sequence having at least 80% sequence identity to SEQ ID NO: 77, a nucleic acid sequence having 1 or 2 substitutions when compared to SEQ ID NO 77, SEQ ID NO: 78 (NRAS Exon 2+flanking sequences), a nucleic acid sequence having at least 80% sequence identity to SEQ ID NO: 78, a nucleic acid sequence having 1 or 2 substitutions when compared to SEQ ID NO 78, and wherein the oligonucleotide does not comprise a stretch of more than 3, such as no more than 4 or 5 consecutive unmodified RNA nucleosides.

(ii) optionally, a fragment consisting of 10 to 30 linked nucleosides having a nucleobase sequence which is not complementary to a region of equal length of a nucleic acid sequence selected from the list consisting of SEQ ID NO: 76 (HRAS Exon 2+flanking sequences), SEQ ID NO: 78 (NRAS Exon 2+flanking sequences), and SEQ ID NO: 77 (KRAS Exon 2+flanking sequences).

(iii) optionally a delivery vehicle, such as an aptamer.

2. A SSO according to embodiment 1, wherein the SSO is complementary to at least one splicing regulatory site 3. A SSO according to any one of embodiments 1 or 2, wherein the SSO is complementary to at least one exonic splicing enhancer element (ESE) or a part thereof.

4. A SSO according to any one of the preceding embodiments, wherein the SSO is complementary to a sequence which comprises at least two ESE elements or a part thereof.

5. A SSO according to any one of embodiments 1 to 4, wherein the SSO is complementary to a sequence which comprises a splice donor or a splice acceptor site.

6. The SSO according to any one of the preceding embodiments, wherein (i) is 10 nucleobases, such as 11, such as 12, 13, 14, 15, 16, 17, 18, 19, 20, 21, 22, 23, 24, or 25 nucleobases.

7. The SSO of any one of the preceding embodiments, wherein (ii) is capable of binding a splicing inhibitory protein.

8. The SSO of any one of the preceding embodiments, wherein (ii) is capable of binding a splicing inhibitory protein from the hnRNPF/H family of splicing inhibitory proteins.

9. The SSO of any one of the preceding embodiments, wherein (ii) contains at least one CAGGG(T/U) or (U/T) AGGGA motif.

10. The SSO of any one of the preceding embodiments, wherein (ii) is positioned 3' to (i) in said oligonucleotide.

11. The SSO of embodiment 10, wherein (ii) is selected from the group of sequences consisting of SEQ ID NO: 33, SEQ ID NO: 35, SEQ ID NO: 37, SEQ ID NO: 39, and SEQ ID NO: 41

12. The SSO of any one of embodiments 1 to 9, wherein (ii) is positioned 5' to (i) in said SSO.

13. The SSO of embodiment 12, wherein (ii) is selected from the group of sequences consisting of SEQ ID NO: 32, SEQ ID NO: 34, SEQ ID NO: 36, SEQ ID NO: 38, and SEQ ID NO: 40.

14. The SSO according to any one of the preceding embodiments, wherein (i) comprises any one of SEQ ID NO: 2, 4, 5, 6, 7, 8, 9, or 10, or any one of SEQ ID NO: 56, 57, 58 or 59, or has no more than 1 or 2 mismatches or is at least 80% homologous to any one of SEQ ID NO: 1, 2, 3, 4, 5, 6, 7, 8, 9, or 10, or any one of SEQ ID NO: 56, 57, 58 or 59.

15. The SSO according to any one of the preceding embodiments, wherein (i) comprises any one of SEQ ID NO: 1, 3 or 11, or has no more than 1 or 2 mismatches or is at least 80% homologous to any one of SEQ ID NO: 1, 3 or 11.

16. The SSO according to any one of the preceding embodiments, wherein (i) comprises any one of SEQ ID NO: 21, 22, 19, 20, 63, 65, 72, 73, 75, 71, 66, 74, 68, 60, 61, 62, 64, 69, 67, 70, or has no more than 1 or 2 mismatches or is at least 80% homologous to any one of SEQ ID NO: 21, 22, 19, 20, 63, 65, 72, 73, 75, 71, 66, 74, 68, 60, 61, 62, 64, 69, 67, 70.

17. The SSO according to any one of the preceding embodiments, wherein (i) comprises any one of SEQ ID NO: 12, 13, 17 or 18, or has no more than 1 or 2 mismatches or is at least 80% homologous to any one of SEQ ID NO: 12, 13, 17 or 18.

18. The SSO according to any one of the preceding embodiments, wherein (i) comprises any one of SEQ ID NO: 25, 27 or 28, or has no more than 1 or 2 mismatches or is at least 80% homologous to any one of SEQ ID NO: 25, 27 or 28.

19. The SSO according to any one of the preceding embodiments, wherein (i) comprises any one of SEQ ID NO: 23, 24 or 30, or has no more than 1 or 2 mismatches or is at least 80% homologous to any one of SEQ ID NO: 23, 24 or 30.

20. A SSO according to any one of the preceding embodiments, wherein the SSO comprises at least one sugar modified nucleotide.

21. A SSO according to any one of the preceding embodiments, wherein the SSO comprises a pattern of sugar modified nucleotide analogues so that the SSO does not have a stretch of more than 3, such as 4, or 5, or 6 contiguous non modified residues.

22. The SSO of any one of the preceding embodiments, wherein the oligonucleotide is does not mediate RNAse H mediated degradation of the mRNA.

23. The SSO according to embodiment 20 or 21, wherein at least one modified sugar moiety is a 2'-substituted sugar moiety.

24. The SSO according to embodiment 23, wherein said 2'-substituted sugar moiety has a 2'-substitution selected from the group consisting of 2'-O-Methyl (2'-OMe), 2'-fluoro (2'-F), and 2'-O-methoxyethyl (2'-MOE).

25. The SSO according to embodiment 23 or 24, wherein said 2'-substitution of said at least one 2'-substituted sugar moiety is a 2'-O-methoxyethyl (2'-MOE).

26. The SSO according to any one of embodiments 20 or 21, wherein at least one modified sugar moiety is a bicyclic sugar moiety.

27. The SSO according to embodiment 26, wherein at least one bicyclic sugar moiety is a locked nucleic acid (LNA) or constrained ethyl (cEt) nucleoside.

28. The SSO according to any one of embodiments 20 or 21, wherein at least one sugar moiety is a sugar surrogate.

29. The SSO according to embodiment 28, wherein at least one sugar surrogate is a morpholino.

30. The SSO according to embodiment 29, wherein at least one morpholino is a modified morpholino.

31. The SSO according any one of the preceding embodiments, wherein the SSO comprises at least one internucleoside N3' to P5' phosphoramidate diester linkage.

32. The SSO according any one of the preceding embodiments, wherein the modified oligonucleotide comprises at least one internucleoside phosphorothioate linkages.

33. The SSO according to any one of embodiments 1 to 30 or 32, wherein all internucleoside linkages are phosphorothioate.

34. The SSO according to any one of the preceding embodiments with the proviso that said modified oligonucleotide is not a gapmer having a gap or more than 4, such as more than 5 or 6.

35. The SSO according to any one of the preceding embodiments, wherein at least 50%, such as at least 60%, such as at least 70%, such as at least 80%, such as at least 90%, such as all nucleotides are modified on the sugar moiety.

36. A pharmaceutical composition comprising the SSO according to any one of the preceding embodiments.

37. A pharmaceutical composition comprising the SSO according to any one of the preceding embodiments, wherein the composition comprises two or three SSO's.

38. The pharmaceutical composition according to embodiment 37, wherein the composition comprises two non-overlapping KRAS SSOs, or two non-overlapping HRAS SSOs or two non-overlapping NRAS SSOs.

39. The pharmaceutical composition according to embodiment 37, wherein the composition comprises one KRAS SSO, one HRAS SSO and one NRAS SSO, or one KRAS SSO and one NRAS SSO, or one KRAS SSO and one HRAS SSO, or one HRAS SSO and one NRAS SSO.

40. The SSO according to any one of the preceding embodiments for use as a medicament.

41. The SSO according to any one of the preceding embodiments for use in treating a cancer and/or a Rasopathy.
42. The SSO according to embodiment 41, wherein the use is for treating a Rasopathy which is Costellos syndrome.
43. The SSO for use according to embodiment 41, wherein said cancer is a haematological cancer.
44. The SSO for use according to embodiment 41, wherein said cancer is a cancer selected from the group consisting of multiple myeloma cancer, lung cancer, colorectal cancer, skin cancer, pancreas cancer, bladder cancer, liver cancer, breast cancer and prostate cancer.
45. A method of modulating splicing in a transcript in a cell, comprising contacting the cell with the SSO according to any one of the preceding embodiments.
46. A method for treating a condition characterized at least in part by constitutively active RAS or mutant RAS, comprising administering a therapeutically effective amount of the SSO according to any one of the preceding embodiments to a subject in need thereof.
47. In one embodiment, the SSO of the present invention target ESE-A in HRAS
48. In one embodiment, the SSO of the present invention target ESE-B in HRAS and/or KRAS and/or NRAS.
49. In one embodiment, the SSO of the present invention target ESE-C in any one of HRAS, KRAS or NRAS.
50. In one embodiment, the SSO of the present invention target ESE-D in HRAS and/or KRAS.
51. In one embodiment, the SSO of the previous claims, comprises bicyclic nucleotides
52. In one embodiment, the SSO of claim 51, does not comprise a stretch of more than 5 consecutive bicyclic nucleotides, such as more than 6, or 7, 8, 9 or 10 consecutive bicyclic nucleotides.
53. In one embodiment according to any one of claim 51 or 52, the SSO comprises at least 50% bicyclic nucleotides, such as any one of 60%, 70%, 80%, 90% or at least 95% bicyclic nucleotides.
54. In one embodiment according to any one of claims 51 to 53, the SSO comprises no more than 95% bicyclic nucleotides, such as no more than 90% or no more than 80% or no more than 60% or no more than 50% bicyclic nucleotides.
55. In one embodiment, the SSO according to any one of the preceding claims mediate alternative splicing of the targeted pre-mRNA and thereby lead to production of a new RAS isoform with a dominant negative effect on either cancer cell survival or on symptoms of a rasopathy such as in example Costello syndrome.
56. In one embodiment the SSOs of the present invention, and according to any one of the previous embodiments are for use in a method of treatment of a RAS related disease, such as a HRAS or a KRAS or a NRAS related disease.
57. In one embodiment according to embodiment 56, the RAS related disease is a cancer or a rasopathy.
58. In one embodiment according to embodiment 57, the RAS related disease is any one of Costello syndrome, haematological cancer such as multiple myeloma, acute myeloblastic leukemia, chronic myelogenic leukemia, acute lymphoblastic leukemia and chronic lymphocytic leukemia or a cancer selected from the list of lung cancer, colorectal cancer, skin cancer, pancreas cancer, bladder cancer, liver cancer, breast cancer and prostate cancer

EXAMPLES

In the following experimental examples of the present invention the following nomenclature applies to the sequences, which are included in the sequence listing. Numbering of nucleotide positions are typically referring to the position in the c.DNA sequences for the listed reference c.DNA sequences using "A" at the normal ATG translation start codon in exon 2 as position c.1: NM_001130442.1, NM_005343.2, NM_176795.3, NM_004985.3, NM_033360.2 and NM_002524.4.

| Sequence identity no in Sequence Listing | Name or function |
|---|---|
| SEQ ID NO 1 | HRAS-SSO1 |
| SEQ ID NO 2 | HRAS-SSO2 |
| SEQ ID NO 3 | HRAS-SSO3 |
| SEQ ID NO 4 | HRAS-SSO4 |
| SEQ ID NO 5 | HRAS-SSO5 |
| SEQ ID NO 6 | HRAS-SSO6 |
| SEQ ID NO 7 | HRAS-SSO7 |
| SEQ ID NO 8 | HRAS-SSO8 |
| SEQ ID NO 9 | HRAS-SSO9 |
| SEQ ID NO 10 | HRAS-SSO10 |
| SEQ ID NO 11 | HRAS-SSO11 |
| SEQ ID NO 12 | KRAS-SSO1 |
| SEQ ID NO 13 | KRAS-SSO2 |
| SEQ ID NO 14 | KRAS-SSO3 |
| SEQ ID NO 15 | KRAS-SSO4 |
| SEQ ID NO 16 | KRAS-SSO5 |
| SEQ ID NO 17 | KRAS-SSO6 |
| SEQ ID NO 18 | KRAS-SSO7 |
| SEQ ID NO 19 | KRAS-SSO8 |
| SEQ ID NO 20 | KRAS-SSO9 |
| SEQ ID NO 21 | KRAS-SSO10 |
| SEQ ID NO 22 | KRAS-SSO11 |
| SEQ ID NO 23 | NRAS-SSO1 |
| SEQ ID NO 24 | NRAS-SSO2 |
| SEQ ID NO 25 | NRAS-SSO3 |
| SEQ ID NO 26 | NRAS-SSO4 |
| SEQ ID NO 27 | NRAS-SSO5 |
| SEQ ID NO 28 | NRAS-SSO6 |
| SEQ ID NO 29 | NRAS-SSO7 |
| SEQ ID NO 30 | NRAS-SSO8 |
| SEQ ID NO 31 | NRAS-SSO9 |
| SEQ ID NO 32 | Tail sequence |
| SEQ ID NO 33 | Tail sequence |
| SEQ ID NO 34 | Tail sequence |
| SEQ ID NO 35 | Tail sequence |
| SEQ ID NO 36 | Tail sequence |
| SEQ ID NO 37 | Tail sequence |
| SEQ ID NO 38 | Tail sequence |
| SEQ ID NO 39 | Tail sequence |
| SEQ ID NO 40 | Tail sequence |
| SEQ ID NO 41 | Tail sequence |
| SEQ ID NO 42 | SSO-Control |
| SEQ ID NO 43 | KRAS exon 1 primer |
| SEQ ID NO 44 | KRAS exon 2 primer |
| SEQ ID NO 45 | HRAS exon 1 primer (HRAS1sNhel) |
| SEQ ID NO 46 | HRAS exon 2 primer |
| SEQ ID NO 47 | HRAS minigene specific primer |
| SEQ ID NO 48 | HRAS primer |
| SEQ ID NO 49 | NRAS exon 1 primer |
| SEQ ID NO 50 | NRAS exon 2 primer |
| SEQ ID NO 51 | HRASWt |
| SEQ ID NO 52 | HRAS35T |
| SEQ ID NO 53 | HRAS35-36TG |
| SEQ ID NO 54 | HRAS1asXhol |
| SEQ ID NO 55 | RasEx4Ex3 |
| SEQ ID NO 56 | HRAS-SSO19 |
| SEQ ID NO 57 | HRAS-SSO20 |
| SEQ ID NO 58 | HRAS-SSO27 |
| SEQ ID NO 59 | HRAS-SSO30 |
| SEQ ID NO 60 | KRAS-SSO12 |
| SEQ ID NO 61 | KRAS-SSO13 |
| SEQ ID NO 62 | KRAS-SSO14 |
| SEQ ID NO 63 | KRAS-SSO15 |
| SEQ ID NO 64 | KRAS-SSO16 |
| SEQ ID NO 65 | KRAS-SSO17 |
| SEQ ID NO 66 | KRAS-SSO18 |
| SEQ ID NO 67 | KRAS-SSO19 |

| Sequence identity no in Sequence Listing | Name or function |
| --- | --- |
| SEQ ID NO 68 | KRAS-SSO20 |
| SEQ ID NO 69 | KRAS-SSO21 |
| SEQ ID NO 70 | KRAS-SSO22 |
| SEQ ID NO 71 | KRAS-SSO23 |
| SEQ ID NO 72 | KRAS-SSO24 |
| SEQ ID NO 73 | KRAS-SSO25 |
| SEQ ID NO 74 | KRAS-SSO26 |
| SEQ ID NO 75 | KRAS-SSO28 |
| SEQ ID NO 76 | HRAS genomic sequence NT_187586.1 nucleotides 1131-1400 |
| SEQ ID NO 77 | KRAS genomic sequence NG_007524.1 nucleotides 5461-5720 |
| SEQ ID NO 78 | NRAS genomic sequence NG_007572.1 nucleotides 661-920 |

Members of the RAS Family

The important signaling molecule RAS belongs to the superfamily of monomeric GTPases [Carmena 2012]. Members of the RAS family are GTP-binding switch proteins, which are ubiquitously expressed, although at varying levels [To et al. 2012]. The products of the different RAS genes are collectively called p21 [Cohen et al. 1989]. The mammalian genome encodes tree RAS genes that are translated into closely related proteins of 21 kDa that are highly conserved at the N-terminus (amino acid 1-165), but vary in the C-terminal region (amino acid 165-188/189), due to their distinct roles in cellular processes [Oliva et al. 2004; Bar-Sagi 2001]. The tree RAS homologues termed Harvey-RAS (HRAS), Neuroblastoma-RAS (NRAS) and Kirsten-RAS (KRAS)—K-RAS4A or K-RAS4B, generated from two alternative fourth exons, encode the four highly related GTPases of 188 (KRAS4B) or 189 (HRAS, KRAS4A and NRAS) amino acid in length.

HRAS is located on chromosome 11p15.5 and consist of 6 exons of which exon 6 has three variants; a, b and c, where a and b comprises the two halves of c [Entrez Gene, NCBI Reference Sequence: NG_007666.1]. The KRAS gene maps to position p12.1 of chromosome 12. This proto-oncogene encodes a protein consisting of 6 exons [Entrez Gene, NCBI Reference Sequence: NG_007524.1], whereas NRAS consist of seven exons and is located on chromosome 1p13.2 [Entrez Gene, NCBI Reference Sequence: NG_007572.1].

The cellular concentration of RAS-GTP is increased due to the actions of a variety of growth factors, enabling this GTPase to interact with its target proteins. The high degree of sequence homology between the three RAS proteins and the ability of mutated variants to cause transformation of NIH 3T3 fibroblasts and other cell types, have up until now indicated that all RAS proteins have the same role in vivo [Oliva et al. 2004]. However, due to differences in their posttranslational modifications, they localize differently, supporting the suggestion of different roles of the three RAS homologues. It is now strongly proposed that the different RAS variants generate distinct signal output despite interacting with a set of common activators and effectors [Oliva et al. 2004; Parikh et al. 2007]. The biological differences are most likely accounted for by the 25 amino acids in the hypervariable domain (HVR) in the carboxy-terminal. The HVR encodes the protein sequences necessary for RAS to associate with the inner plasma membrane. RAS proteins are synthesized as cytosolic precursors, which undergo post-translational processing enabling the proteins to associate with the cell membranes. Initially, a farnesyl group is attached to the cysteine residue of the CAAX motif—a part of the HVR—targeting RAS to the cytosolic surface of the Endoplasmic reticulum (ER), where the AAX tripeptide is removed. The α-carboxyl group on the carboxyl-terminal farnesyl-cysteine is for unknown reasons more efficiently methylated in KRAS than HRAS and NRAS. HRAS and NRAS undergo a continuous cycle of de- and re-palmitoylation on cysteine residues in the HVRs, regulating the rapid exchange between the plasma membrane and the Golgi apparatus. KRAS bypasses the Golgi as its reaches the plasma membrane, due to a polylysine sequence instead of cysteine residues [reviewed by Hancock 2003].

Mutations of the RAS-MAP Kinase Pathway

Alterations in the cellular genome, which affect expression or function of genes controlling cell growth and differentiation, are considered to be the main cause of cancer [Bos 2007]. Although cancer comprises numerous different diseases, all cancer cells result from disruption of normal cell cycle regulation, causing the cycle to proceed without control. Cells that display uncontrolled growth and division can divide independently and accumulate genetic defects leading to cancerous tumors. These changes may be a result of germ line mutations, which are inherited genetic alterations; however, hereditary cancer syndromes are rare [Roukos 2009]. Gene mutations, which are acquired during life and only present in certain cells, are called somatic mutations and are not inherited. Alterations in the same gene are often associated with different forms of diseases [reviewed by Futreal et al. 2004].

Since activating mutations in RTKs or proteins of the RAS-MAP kinase cascade are found in almost all types of human tumors, the RAS-MAP kinase pathway has been suggested to be responsible for the malignant phenotype [Lodish et al. 2008]. As many cancers appear to involve mutations in RTK receptors, they have shown to be an effective target for treatment of human cancers [Gschwind et al. 2004]. Since RAS proteins have been associated with many types of human cancer, mutated RAS proteins have attracted great interest as therapeutic targets. Much about the RAS GTPase cycle and the biochemical consequences of somatic mutations occurring in cancer has been learned over the past three decades [reviewed by Malumbres and Barbacid 2003; Downward 2006]. In the RAS-MAP kinase pathway RAS and RAF have been identified as proto-oncogenes [Zenker 2011], and since expression of mutated RAS has been shown to be implicated in tumor development, this indicates the potency of RAS oncogenes as drivers in the pathogenesis of human tumors [To et al. 2012].

Mutations affecting the three different oncogenes (HRAS, NRAS and KRAS) display a high degree of tumor specificity with respect to which family member of the Ras genes that is mutated [Parikh et al. 2007]. Whereas mutations in HRAS are commonly seen in bladder, head, neck and skin cancers, mutations in KRAS are common in lung, pancreatic, and colon cancers, while those in NRAS predominate in melanoma [To et al. 2012]. NRAS and KRAS mutations are also very frequent in many hematological cancers, like multiple myeloma [Fernandez-Medarde et al. 2011]. An explanation for HRAS, KRAS and NRAS mutations to occur at varying frequencies across different tumors in humans is that expression of the RAS gene family members is controlled in a tissue-specific manner [Berns 2008]. KRAS mutations are found in nearly 90% of pancreatic cancers [Parikh et al. 2007], and somatic mutations in KRAS and BRAF belong to the most common genetic alterations observed in a variety of malignancies [reviewed by Zenker 2011]. However, in myeloid malignancies NRAS mutations are more frequent than KRAS, whereas HRAS mutations are rare [Parikh et al. 2007]. Understanding the tumor-type specificity of RAS oncogenes could prove important for the design of targeted therapies.

Transforming Potential of HRAS Mutations

Oncogenic RAS can transform cells to a tumorigenic state and different mutations in HRAS are currently known to result in different transforming potentials [Kerr et al. 2006]. The p.Gly12Ser activating mutation in HRAS, which is the most frequent mutation causing Costello syndrome, exhibit intermediate transforming properties, while the p.Gly12Val—the most commonly identified HRAS mutation in human cancers, but very rare in Costello syndrome patients—has the highest transforming activity (p.Gly12Val>p.Gly12Ala, p.Gly12Ser, p.Gly12Cys, p.Gly12Asp>p.Gly13Asp) [Fasano et al. 1984; Lo et al. 2008]. Not only can any of several mutations of the 12th codon activate the transforming potential of the HRAS gene, but also mutations of codon 13 and 63 are capable [Fasano et al. 1984].

Computer prediction by Fasano and colleagues suggested that any amino acid substitution of glycine at position 12 significantly alters RAS conformation by extending the protein from its normally compact form which influences the protein mobility. These observations are consistent with the idea that the amino acid substitutions that activate RAS do so by disrupting protein structure, thereby disrupting critical protein functions [Fasano et al. 1984].

In 1984 Seeburg et al. constructed an extensive series of human HRAS mutant cDNAs altered at codon 12 and assessed the ability of each encoded mutant protein to transform Rat1 cells. Seeburg et al. found that any amino acids at residue 12—except the wild-type glycine and proline—possessed the ability to promote independent cellular growth [Seeburg et al. 1986]. Despite that glycine 12 point mutations are activating, the morphological phenotype depends on the particular amino acid substitution at this position. p.Gly12Val (c.35G>T) and p.Gly12Arg (c.34G>C) mutant cDNAs have robust transformation phenotypes, compared to p.Gly12Ser (c.34G>A), p.Gly12Ala (c.35G>C), p.Gly12Asp (c.35G>A), which are less striking morphologically, although transforming. Thus, it has been suggested that the viability of the phenotype of CS is due to differences in the activating potential of the different HRAS mutations [Lo et al. 2008].

Moreover, the relative transformation potential of the mutations could also be reflected in their occurrence in cancer. According to the Cosmic database (http://cancer.sanger.ac.uk/cancergenome/projects/cosmic/) the transformation potential of various mutations is only partly reflected in their relative frequency of occurrence in somatic cancers: The p.Gly12Val (c.35G>T) is by far the most frequently observed (47% of all single nucleotide substitutions in codon 12 and 13), whereas the most potent transforming mutation, p.Gly12Arg (c.34G>C) is very infrequent (2%), and less potent mutations, which have similar transformation potentials are observed with varying frequencies in tumors; p.Gly12Ser (c.34G>A) (11%), p.Gly12Ala (c.35G>C) (2%) and p.Gly12Asp (c.35G>A) (10%).

The present inventors established a minigene (Described in materials and methods section) and performed site directed mutagenesis in order to investigate the effect of a number of the single nucleotide substitutions in codons 12 and 13 of HRAS, which are known to be associated with cancer (COSMIC database: http://cancer.sanger.ac.uk/cosmic/gene/overview?ln=HRAS) and/or Costello syndrome.

Figure 1:
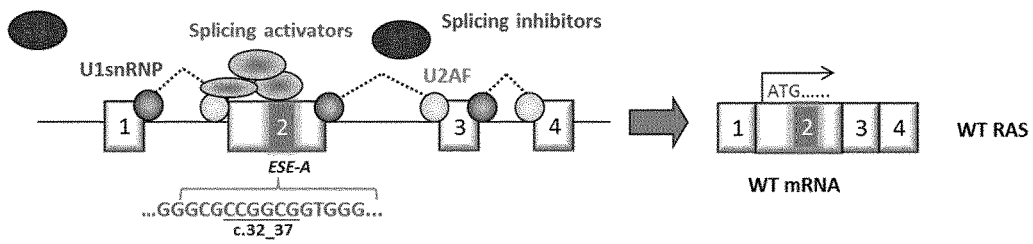
FIG. 1 shows SSO blocking of HRAS exon 2 splicing. A, in absence of SSO normal gene expression is maintained. Splicing of HRAS exon 2 depends on splicing enhancer sequences (ESEs) to be recognized by the splicing activating factors in order to recruit the spliceosome to the suboptimal 3'ss. Binding of splicing activators within exon 2 promotes its inclusion in the mRNA. B, SSOs (red) targeting a region harboring ESEs within exon 2, exclude this exon from the mRNA. C, SSOs targeting either the 3'ss or 5'ss causes skipping of exon 2, as it blocks assembling of the spliceosome on the splice sites. Shown is an SSO targeting the 3'ss. WT: wild-type, ESE: exonic splicing enhancer, SSO: Splice shifting oligonucleotides.
Figure 1:
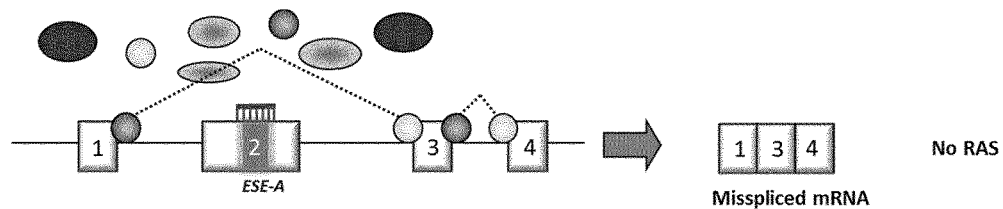
Figure 1:
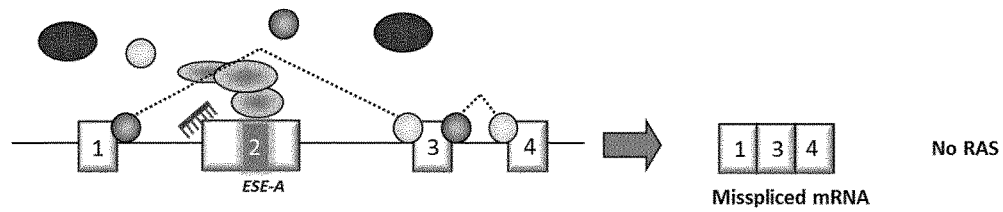
Figure 2:
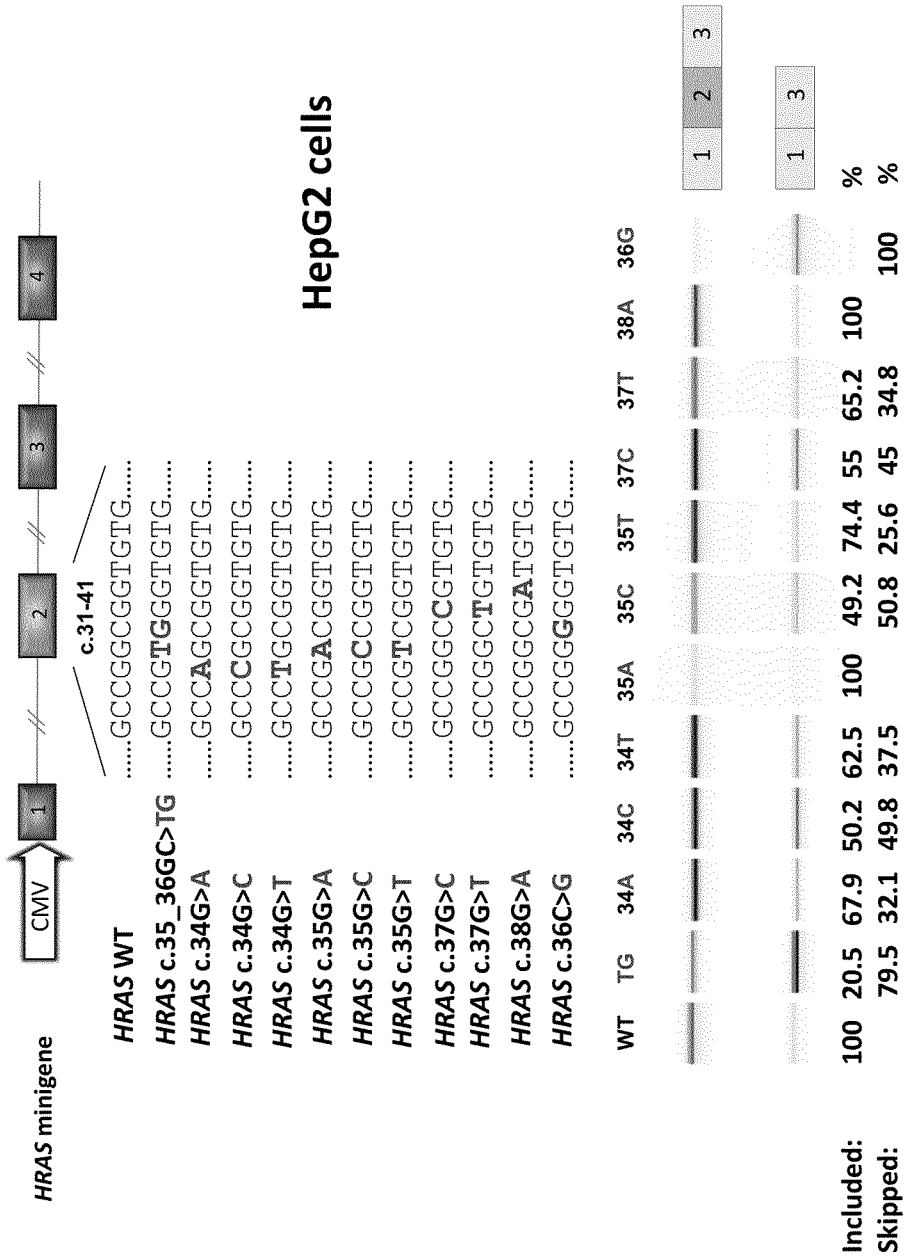
FIG. 2 shows transfection of HepG2 cancer cells. This figure shows the structure of the HRAS minigene, which consist of exons 1, 2, 3 and 4 and the flanking introns. The minigene is under transcriptional control of a CMV promoter. The listed HRAS mutations affecting codons 12 and 13 and shown to be associated with cancers and/or Costello syndrome were introduced by standard site directed mutagenesis. The minigene was transfected into HepG2 cells. 48 hours post transfection RNA was extracted, cDNA prepared and HRAS exon 2 skipping was analyzed by PCR as described in materials methods. PCR products were analyzed by electrophoresis in a bioanalyzer 2100. Band intensities from three experiments were used to calculate the molar ratio between bands resulting from exon 2 inclusion and exon 2 skipping. The transfections were performed in triplicate and the experiments repeated twice using Lipofectamine® RNAiMax. This showed that mutations in codons 12 and 13 may cause variable degrees of exon 2 missplicing by skipping of exon 2. Because exon 2 skipping leads to no functional HRAS, this indicates that the efficiency of exon 2 inclusion of the different HRAS mutations may be an important determinant for their tumorigenic potential. Some mutations that encode mutant HRAS proteins with potent transformation potential are despite this infrequent in tumors as reported to the Cosmic database (http://cancer.sanger.ac.uk/cosmic/gene/overview?ln=H RAS). In particular, p.Gly12Ala (c.35G>C) and p.Gly12Arg (c.34G>C) which show extensive skipping of exon 2 are infrequent in tumors despite encoding potent tumorigenic proteins. Moreover, the most frequently observed mutation in cancer, p.Gly12Val (c.35G>T), which also has the most robust transformation potential, showed enhanced exon 2 inclusion, and also the frequent cancer mutation, p.Gly12Asp (c.35G>A) showed increased exon inclusion compared to wild-type HRAS. This suggests that the mutations that increase exon 2 skipping have a lower tumorigenic potential.
Figure 3:
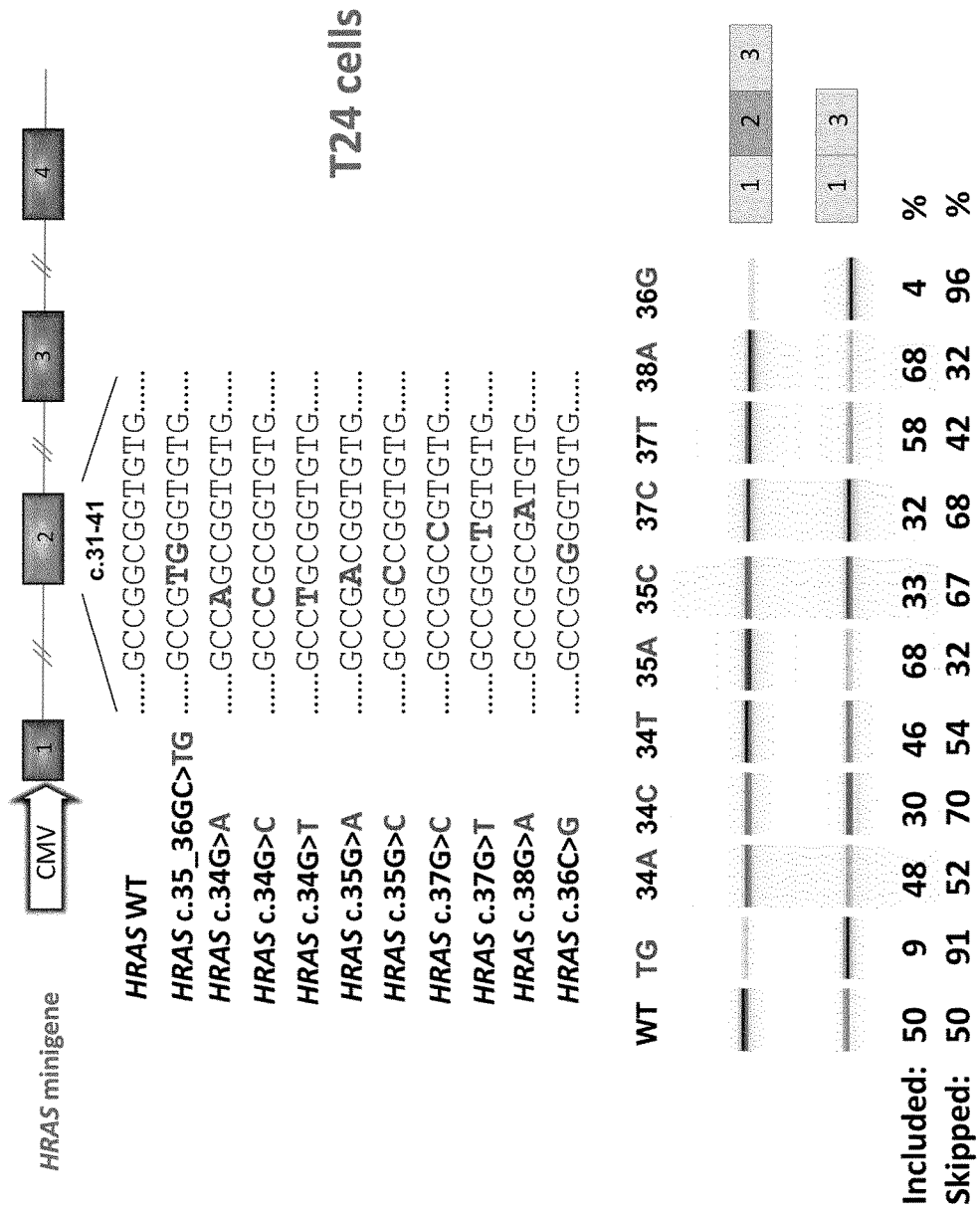
FIG. 3 shows transfection of T24 cancer cells. This figure shows that also in T24 bladder cancer cells mutations in codons 12 and 13 cause variable degrees of exon 2 missplicing by skipping of exon 2. Because exon 2 skipping leads to no functional HRAS, this indicates that the exon 2 inclusion efficiency of the different HRAS mutations may be an important determinant for their tumorigenic potential. The listed HRAS mutations affecting codons 12 and 13 and shown to be associated with cancers and or Costello syndrome were introduced by site directed mutagenesis. The minigene was transfected into T24 cells. 48 hours post transfection RNA was extracted, cDNA prepared and HRAS exon 2 skipping was analyzed by PCR as described in materials methods. PCR products were analyzed by electrophoresis in a bioanalyzer 2100. Band intensities from three experiments were used to calculate the molar ratio between bands resulting from exon 2 inclusion and exon 2 skipping. The transfections were performed in triplicate and the experiments repeated twice using Lipofectamine® RNAiMax.
Figure 4:
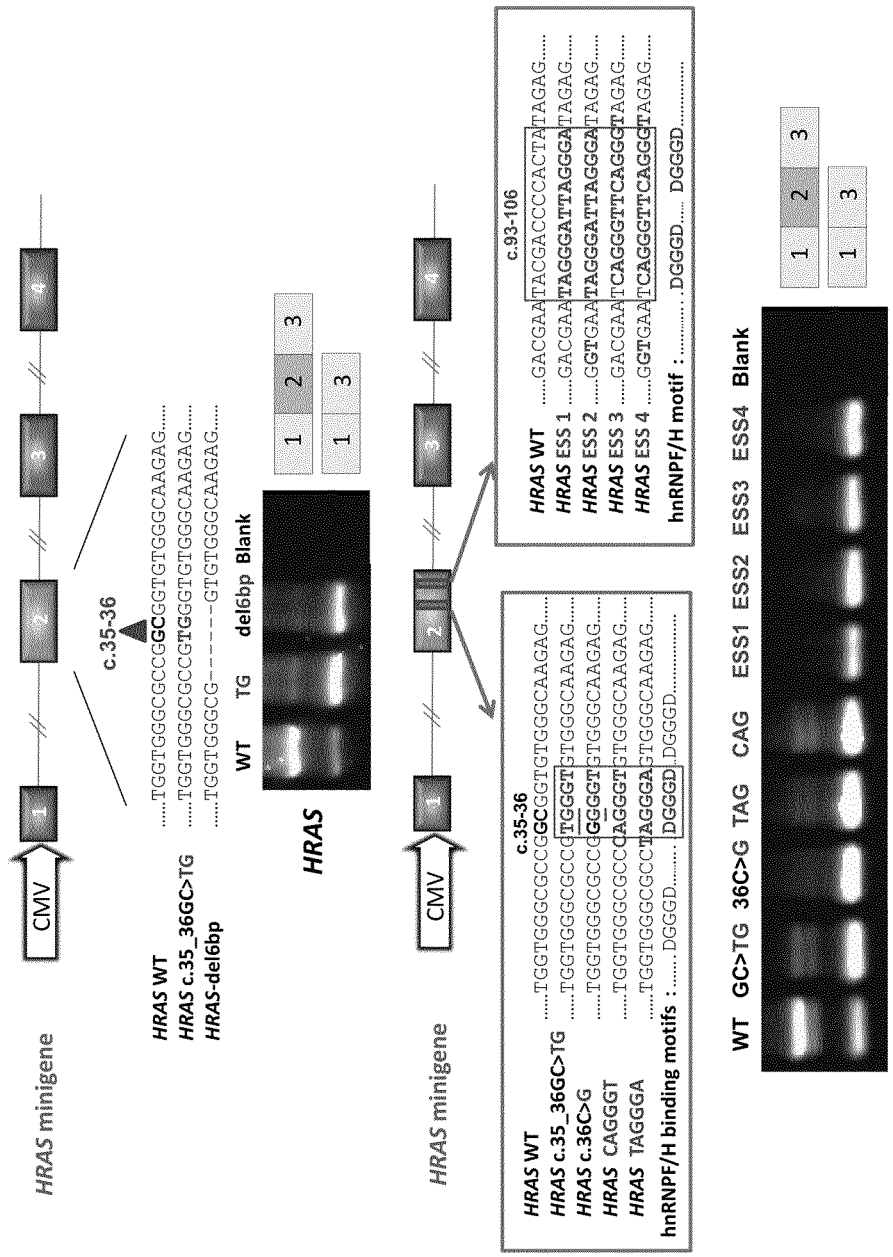
FIG. 4 shows that mutations c.35_36GC>TG (p.Gly12Val) and c.36C>G (p.Gly12Gly) results in nearly complete HRAS exon 2 skipping, demonstrating that recognition of exon 2 by the spliceosome, and thus exon 2 inclusion in HRAS mRNA, is critically dependent on the exon 2 nucleotide sequence. Deletion of the nucleotides c.32-37 causes exon 2 skipping, indicating presence of an exonic splicing enhancer (ESE-A) in this region. Replacement in the HRAS minigene of the wild-type sequence from c.34-c.39 with ESS motifs previously shown to bind hnRNPF/H family splicing inhibitory proteins (Dobrowolski et al. 2010; Olsen et al. 2013) (CAGGGT and TAGGGA) or replacement in the HRAS minigene of the wild-type sequence from c.94-c.106 with sequences consisting of repeats of these motifs (ESS1 and ESS3) confirmed that binding of hnRNPF/H results in exon 2 skipping and that these sequences (SEQ ID NO 32, SEQ ID NO 33, SEQ ID NO 34, SEQ ID NO 35 SEQ ID NO 36, SEQ ID NO 37, SEQ ID NO 38, SEQ ID NO 39, SEQ ID NO 40 and SEQ ID NO 41) can mediate exon 2 skipping. The listed mutations were introduced by site directed mutagenesis into the minigene, which was transfected into HepG2 cells. 48 hours post transfection RNA was extracted, cDNA prepared and an HRAS exon 2 skipping was analyzed by PCR. PCR products were analyzed by electrophoresis in an agarose gel. The transfections were performed in triplicate and the experiments repeated twice using Lipofectamine® RNAiMax. Blank: Represents a control PCR without added cDNA.

The minigenes were used to transfect HepG2 and T24 cells. This showed that mutations in these codons may cause variable degrees of exon 2 misslicing by skipping of exon 2 (FIG. 2 and FIG. 3). Skipping of exon 2 would lead to a non-functional protein, since both the start codon and amino acids critical for the function of HRAS are located in exon 2. Interestingly, some mutations, for instance p.Gly12Ala (c.35G>C) and p.Gly12Arg (c.34G>C), which encode mutant HRAS proteins with potent transformation potential are infrequent in tumors. The inventors found that in particular, p.Gly12Ala (c.35G>C) and p.Gly12Arg (c.34G>C) showed extensive skipping of exon 2 (FIG. 2 and FIG. 3). Moreover, the most frequently observed mutation in cancer, p.Gly12Val (c.35G>T), which also has the most robust transformation potential, shows enhanced exon 2 inclusion (FIG. 3), and also the p.Gly12Asp (c.35G>A) mutation, which is frequent in cancers showed increased exon inclusion compared to wild type HRAS (FIG. 2 and FIG. 3). This indicates that the exon 2 inclusion efficiency of the different HRAS mutations may be an important determinant for their tumorigenic potential and Costello syndrome phenotype. Mutations c.35_36GC>TG (p.Gly12Val) and c.36C>G (p.Gly12Gly) results in nearly complete exon skipping (FIG. 4), demonstrating that recognition of exon 2 by the spliceosome, and thus exon 2 inclusion in HRAS mRNA, is critically dependent on the exon 2 nucleotide sequence. Deletion of the nucleotides c.32-37 causes exon 2 skipping, indicating presence of an exonic splicing enhancer (ESE) in this region (FIG. 4). Testing of nucleotides c.13-c.47 in a RHC-glo splicing reporter minigene [Singh and Cooper 2006] confirmed the presence of at least one ESE (ESE-A—c.32-c.37—See FIG. 13) in the tested part of HRAS exon 2, since splicing of the reporter test exon is dependent on the presence of ESE sequences in the inserted sequence. The function of ESE-A in the inserted sequence is disrupted by the c.35_36GC>TG mutation and by the c.35G>C (p.Gly12Ala), but strengthened by the c.35G>T (p.Gly12Val) mutation (FIG. 5).

Analysis of the 5'- and 3'-splice sites flanking HRAS exon 2, showed that both are weak and therefore likely to be dependent on ESE's in order to be recognized efficiently.

This is in particular due to the presence of a GGG triplet in the polypyrimidine tract of the weak 3' splice site (FIG. 6), since this represents a potential binding site for splicing inhibitory proteins from the hnRNPF/H family (Schaub et al. 2007; Masuda et al. 2008; Dobrowolski et al. 2010; Olsen et al. 2014), which could compete with U2AF65 binding to the 3'-splice site of HRAS exon 2 and thereby decrease splicing efficiency. Since hnRNPF/H binding to GGG triplets in a pre-mRNA is cooperative and synergistic (Schaub et al. 2007; Masuda et al. 2008; Dobrowolski et al. 2010; Olsen et al. 2014), mutations creating new GGG triplets in exon 2 are likely to inhibit splicing by acting in synergy with pre-existing GGG triplets, such as the GGG triplet in the weak HRAS exon 2 3'-splice site.

This is consistent with our observation that both c.36C>G and c.3536GC>TG mutations, which create a new GGG triplet in exon 2, result in complete exon 2 skipping (FIG. 4). Optimization of the weak HRAS exon 2 3' splice site, by replacement of the GGG triplet with consensus T nucleotides in the HRAS WT minigene corrected splicing (FIG. 6). This confirmed that HRAS exon 2 is only vulnerable due to the weak splice sites and that inactivation of an ESE, like for instance ESE-A, lead to exon 2 skipping because the weak splice sites require functional ESEs in order to be recognized and mediate exon 2 inclusion into the HRAS mRNA.

RNA affinity purification of HeLa nuclear extract using biotinylated oligonucleotides corresponding to nucleotides c.24-c.45 followed by MS/MS analysis showed that the c.35_36GC>TG mutation increases binding of hnRNPF/H splicing inhibitory proteins and decreases binding of the splicing stimulatory protein SRSF2, whereas c.35G>T increases binding of several splicing stimulatory SR proteins (SRSF1 and SRSF5). This is consistent with the observed effect on splicing from these nucleotide variations, namely that binding of hnRNPF/H splicing inhibitory proteins is inhibitory to exon 2 inclusion and that binding of SRSF2 is crucial for exon 2 inclusion. In line with this, overexpression of hnRNPF or hnRNPH leads to exon 2 skipping and down regulation of SRSF2 by siRNA treatment leads to exon 2 skipping (FIG. 7).

Replacement in the HRAS minigene of the wild type sequence from c.34-c.39 with ESS motifs previously shown to bind hnRNPF/H family splicing inhibitory proteins (Dobrowolski et al. 2010; Olsen et al. 2013) (CAGGGT and TAGGGA) or replacement in the HRAS minigene of the wild-type sequence from c.94-c.106 with sequences consisting of repeats of these motifs (ESS1 and ESS 3) confirmed that binding of hnRNPF/H results in exon 2 skipping and that these sequences (SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40 and SEQ ID NO 41) can mediate exon 2 skipping (FIG. 4).

RAS exon 2 is vulnerable and dependent on ESE sequences, like ESE-A, in order to be included in the final mRNA. Vulnerable exons typically harbor more than one ESE sequence necessary for exon inclusion. Therefore the present inventors investigated the region from c.45 to c.92 of HRAS for other splicing regulatory elements, such as ESE and ESS sequences by introducing nested deletions by site directed mutagenesis in the HRAS minigene (Described in materials and methods section). The minigenes were used to transfect HepG2 cells. This showed that important ESE elements are present at c.DNA positions c.45-50 (ESE-B), c.69-74+c.75-80 (ESE-C) and c.87-92 (ESE-D) (FIG. 5B and FIG. 13).

Exon 2 is Weak in all Three RAS Genes:

The present inventors have found that the HRAS exon 2 3' splice site is weak, and has the lowest score (5.14 using MAXENT) of all 3' splice sites in the human HRAS gene (MEAN score is 8.69) when analyzed by programs that can predict splice site strength (Yeo G, Burge C B. 2004). The KRAS exon 2 3' splice site is also weak, and it has the lowest score (4.99 using MAXENT) of all 3' splice sites in the human KRAS gene (MEAN score is 8.12) when analyzed by programs that can predict splice site strength. Similarly, the NRAS exon 2 3' splice site is weak, and has the second lowest score (9.02 using MAXENT) of all 3' splice sites in the human NRAS gene (MEAN score is 10.12) when analyzed by programs that can predict splice site strength.

In addition, the scores of HRAS, NRAS and KRAS exon 2 5' splice sites also have either the lowest or the second lowest of all the 5' splice site scores in the respective genes. Finally, there is a conserved exonic splicing silencer (ESS) sequence, ATAGAGgt, which overlaps the exon 2 5' splice sites of all three genes, contributing to their weak definition. The TAGAGg silencer motif, which is present in the exon 2 5' splice sites of all three RAS genes is also a high score binding motif for the splicing inhibitory protein hnRNPA1 (with a score of 85.71 on a scale 0-100) according to HSF (Desmet et al. 2009).

Moreover, the ATAGAGgt motif is nearly identical to the splicing silencer consensus sequence motif 1 (CTAGAGGT) described by Sironi et al. (2004) and it is assigned a score of 93.17 (Scale 0-100) by the HSF program.

The importance of this silencer motif overlapping the 5' splice site is also reflected in the relative frequencies of the splice sites harboring this core silencer motif in a database of functional human spice sites (Splicerack—Sheth et al. 2006). Whereas the core motif, ATAGAGgt, is only present in 196 human splice sites, the corresponding sequences, where the silencer motif is disrupted by a single substitution to ACAGAGgt, AAAGAGgt or AGAGAGgt are present in 519, 835 and 547 human splice sites, respectively. Of note here is the fact that splice sites with these sequences have the same score as the original motif when analyzed by splice site prediction programs based on U1snRNA complementarity (Yeo and Burge 2004). The present inventors therefore concluded that, similar to the 3'-splice sites of exon 2, also the 5'-splice sites in all three RAS genes are weak, and, consequently HRAS exon 2, KRAS exon 2 and NRAS exon 2 are suitable targets for SSO-mediated exon skipping.

Splice Shifting Oligonucleotides

In 1978 the field of antisense oligonucleotides was born as Zamecnik and Stephenson discovered that a 13-nucleotide-long oligodeoxynucleotide complementary to a target RNA sequence in Rocus sarcoma virus was able to inhibit replication and translation in vitro [Zamecnik and Stephenson 1978; Stephenson and Zamecnik 1978].

The ability of exon-skipping SSOs to induce expression of an alternatively spliced isoform offers an advantage over traditional antisense oligonucleotide techniques, which merely focus to knockdown of gene expression by degradation or steric blocking of translation into protein by the ribosomes [Disterer and Khoo 2012]. Unlike traditional antisense oligonucleotide techniques, SSOs do not induce RNase-H-mediated cleavage of the mRNA, but instead act by blocking access of splicesosomal components or splicing regulatory factors to the targeted pre-mRNA. SSOs which change the splicing pattern of a targeted pre-mRNAs are able to regulate the presence of disease-related variant proteins by forcing the splicing of the pre-mRNA towards a final mRNA encoding a non-functional protein, due to lack of a vital part of the coding seq, like an exon harboring the normal ATG start codon. In order for SSOs to modulate pre-mRNA splicing, they must block essential RNA splicing regulatory sequences and/or prevent interaction of splicing factors with the pre-mRNA [reviewed by Kole et al. 2012]. Additionally, not all exons are equally responsive to SSO-mediated exon skipping and it has been reported that exons, like Dystrophin exon 9, which show low levels of skipping in normal cells, are particularly well suited as targets for SSO-mediated exon skipping (Fletcher et al. 2012). Analysis of Dystrophin exon 9 shows that similar to RAS exon 2 it has a weak 5' splice site (with several mismatching nucleotides at position +3 and +4 and a 5' splice site MaxEnt score (Yeo and Burge 2004) of only 6.81). Exon-skipping SSO-induced gene silencing has emerged as a unique technique with therapeutic applications. Appropriately designed SSOs target essential pre-mRNA motifs involved in exon recognition, disrupting RNA processing as effectively as splice site mutations. Nevertheless, it took almost one decade after the discovery before chemical modifications, which efficiently protect the SSOs and the targeted pre-mRNA from degradation by nucleases, were introduced. Introduction of phosphorothioate (PTO) internucleotide linkages and 2'-O-methyl-modified nucleotides at the 3' and 5' ends radically increased the stability of the oligonucleotides [reviewed by Kole et al. 2012]. Chemical modifications commonly used in SSOs also include nucleotides with ribose modifications such as 2'OMe, 2'-MOE and locked nucleic acids (LNA), since these modifications inhibit degradation of the targeted pre-mRNA by Rnase-H and other nucleases. PS backbones as well as 2'-MOE or 2'OMe substituents increase resistance to degradation and promote protein binding to target RNA. More radical changes in SSOs chemistry are represented by peptide-nucleic acids (PNA) and phosphorodiamidate morpholino oligomers (PMO), in which the compounds have uncharged backbones [Pramono et al. 2012]. In PMO, RNA or DNA is replaced with morpholino rings, and the phosphorothioate or phosphodiester groups are replaced with uncharged phosphorodiamidate groups, resulting in a compound that is neutral and very resistant to degradation [reviewed by Kole et al. 2012]. In addition, these molecules can be modified with additional moieties, including positively charged peptides or other residues [Pramono et al. 2012].

Identifying exon-internal SSOs, which lead to efficient exon skipping is not a straightforward process due to the vast number of possible target sites. Due to lack of such knowledge a prospective study to validate a minimal set of consistent design variables that are sufficient to design efficient SSOs was conducted by Pramono and colleagues [2012]. They proposed a set of three design variables: 1) co-transcriptional binding accessibility of target site, 2) presence of ESE motifs and 3) target length. Generally, SSOs target length between 20 to 30 nucleotides induce efficient exon skipping using either 2-OMe or PMO oligomer [Pramono et al. 2012]. Aartsma-Rus et al. stated an optimal length of 20 nucleotides for 2-OMePS SSOs, while the optimal range for SSOs with PMO chemistry was reported between 25 to 30 nucleotides by Harding et al. and 30 nucleotides of length by Popplewell et al. [Aartsma-Rus et al. 2009; Harding et al. 2007; Popplewell et al. 2009; Popplewell et al. 2010]. Designing functional SSOs thus relies on identifying ESEs, which are necessary for inclusion of a vulnerable exon and that these ESEs can be blocked by SSO binding. This means that designing SSOs capable of changing splicing of an exon is not always possible and it requires extensive functional investigation of the splicing mechanism in potential target genes in order to identify regulatory ESEs to be targeted and to experimentally test the functionality of designed SSOs targeting the important ESEs.

Splice Shifting Oligonucleotide Design

A series of fourteen HRAS RNA SSOs were designed and synthesized with 2'OMe modification and PTO backbones. SEQ ID NO 1 and SEQ ID NO 11 targets the acceptor site of HRAS exon 2. SEQ ID NO 2 targets position c.30-54, blocking access to ESE-A and ESE-B. SEQ ID NO 3 targets the splice donor site. SEQ ID NO 4 and SEQ ID NO 5 block access to ESE-A and ESE-B (FIG. 5B and FIG. 13). SEQ ID NO 6 blocks access to ESE-D, whereas SEQ ID NO 7 blocks access to ESE-C. SEQ ID NO 56, SEQ ID NO 57, SEQ ID NO 58 and SEQ ID NO 59 each simultaneously blocks access to ESE-C and ESE-D. SEQ ID NO 8, SEQ ID NO 9 and SEQ ID NO 10 targets other segments of HRAS exon 2.

A series of twenty-seven KRAS RNA SSOs were designed and synthesized with 2'OMe modification and PTO backbones. SEQ ID NO 12 targets the acceptor site of KRAS exon 2 and SEQ ID NO 13 targets the donor site. SEQ ID NO 14, SEQ ID NO 15 and SEQ ID NO 16 targets KRAS intron 2. SEQ ID NO 17 and SEQ ID NO 18 targets KRAS intron 1. SEQ ID NO 20, SEQ ID 67 and SEQ ID NO 68 all blocks access to the region of KRAS, which is homologous to ESE-A in HRAS (FIG. 13). SEQ ID NO 60, SEQ ID NO 61, SEQ ID 62, SEQ ID NO 63, SEQ ID NO 64, SEQ ID NO 65, SEQ ID NO 66, SEQ ID NO 69, SEQ ID NO 70, SEQ ID NO 71, SEQ ID NO 72, SEQ ID NO 73 and SEQ ID 74 all block access to ESE-B (FIG. 13). SEQ ID NO 60, SEQ ID NO 61, SEQ ID 62, SEQ ID NO 63, SEQ ID NO 64, SEQ ID NO 67, SEQ ID NO 68, SEQ ID NO 69, SEQ ID NO 72 and SEQ ID 74 all also block access to the region of KRAS, which is homologous to ESE-A in HRAS (FIG. 13). SEQ ID NO 21 blocks access to ESE-B (FIG. 13). SEQ ID NO 22 and SEQ ID NO 75 each simultaneously blocks access to ESE-C and ESE-D. SEQ ID NO 19 targets a different segment of KRAS exon 2.

A series of nine NRAS RNA SSOs were designed and synthesized with 2'OMe modification and PTO backbones. SEQ ID NO 23 targets the acceptor site of NRAS exon 2 and SEQ ID NO 24 targets the donor site.

SEQ ID NO 26 and SEQ ID NO 27 blocks access to the region of NRAS, which is homologous to ESE-A in HRAS (FIG. 13).

SEQ ID NO 28 blocks access to ESE-B (FIG. 13). SEQ ID NO 29 blocks access to the region of NRAS, which is homologous to ESE-C in HRAS, although ESE-C is not conserved in NRAS (FIG. 13).

SEQ ID NO 25 targets different segments of NRAS exon 2.

SEQ ID NO 30 targets NRAS intron 1 and SEQ ID NO 32 targets NRAS intron 2.

A scrambled SSO, which is not complementary to any human mRNA transcripts in the NCBI database by Blast search (http://blast.ncbi.nlm.nih.gov/) SSO-Control (5'-GCUCAAUAUGCUACUGCCAUGCUUG-3' or SEQ ID NO 42) was utilized as control.

SSO-Mediated Skipping of HRAS Exon 2

In contrast to traditional antisense methods, which either aim to down regulate or eliminate RNA by degradation or inhibit translation, SSOs redirect pre-mRNA splicing by blocking recognition of regulatory RNA sequences by the spliceosome and other RNA-binding proteins, preventing these splicing factors from interacting with appropriate sites in the pre-mRNA. This result in redirecting of the spliceosome to alternative sites that leads to an alternative splicing pathway. As exon 2 of HRAS was demonstrated to be weakly defined and thus dependent on splicing stimulatory motifs like ESEs, it was expected to be an optimal target for SSO-mediated exon skipping. Based on our minigene and in vitro RNA purification studies the present inventors could show that at least one critical ESE is localized in the region c.24-c.45 of HRAS exon 2, harboring codons 12-13. Specifically one ESE, ESE-A, was identified at positions c.32-37 (FIGS. 1-7). Blocking this ESE motif with SSOs, exon 2 is no longer recognized as an exon, and spliced out with neighboring introns. Moreover, masking of other critical ESEs within exon 2 also leads to exon skipping.

The splice sites usually offer obvious initial targets, and acceptor splice sites have been suggested as good targets for exon skipping in many exons. In an acceptor site the last 5-10 bases of the intron and first 15-20 bases of exon sequences are typically selected, while SSO targeting the donor site may contain up to 20 bases of intronic sequence [Adkin et al. 2012].

As PTO linkages have shown high stability of the oligonucleotides in vivo, and 2'Ome-PTOs do not mediate degradation of the targeted pre-mRNA, a series of eleven different 2'OMe-PTO SSOs were synthesized to target either the 3' or 5' splice sites, or the wild-type exon sequence, harboring the codon 12 position for wild-type glycine. Twenty-five nucleotides of intron was selected to target the 3'ss, while 5 bases of intron and 20 bases of the exon was chosen as target for the 5'ss. An SSO spanning position c.30-54 targeted the ESE.

Testing of SSOs using the HRAS minigene: When the wild type HRAS minigene was transfected into HepG2 cells the present inventors observed nearly complete skipping of exon 2 when treating with 100 nmol/l of SEQ ID NO 1, SEQ ID NO 2, SEQ ID NO 3, SEQ ID NO 4 or SEQ ID NO 5 for 48 hours (FIG. 8). On the other hand, treating cells transfected with a HRAS WT minigene, where one of the splice sites is optimized according to the splice site consensus sequence, showed no exon 2 skipping.

This clearly demonstrates that vulnerability of exon 2, due to the weakly defined splice sites, is necessary if SSO's should mediate exon skipping.

The level of skipping produced by each SSO at 100 nmol/l 48 hours after treatment was determined by employing a HRAS minigene specific primer (SEQ ID NO 47 or Name: T7-EXT: 5'-ATTAATACGACTCACTATAGGG-3') and a primer complementary to HRAS cDNA position 305-286 (5'-CGTTTGATCTGCTCCCTGTAC-3' as SEQ ID NO 46) of endogenous HRAS by PCR. This produces a 414 bp long product with exon 2 included and a 250 bp long product when exon 2 is skipped. The transfections were performed in duplicate and the experiment repeated twice using Lipofectamine® RNAiMax.

Next SSO treatment of T24 and HepG2 cancer cells was performed with SSOs to induce endogenous HRAS exon 2 skipping. A dose of 40 nmol/l was found to be efficient as illustrated for HepG2 cells treated with SEQ ID NO 2 and SEQ ID NO 3 (FIG. 9). Exon 2 skipping was demonstrated to persist at least 72 hours after treatment (FIG. 9).

Treatment of T24 and HepG2 cancer cells with a dosis of 30 nmol/l SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10 and SEQ ID NO 11 for 48 hours (FIG. 10) shows that several of the SSOs mediate exon 2 skipping at a low SSO dose of 30 nmol/l and that this occurs in both T24 bladder cancer cells and in HepG2 liver cancer cells. This also shows that similar to other reported exons, which have been found to be particularly well suited for SSO mediated exon skipping (Fletcher et al. 2012), skipping of HRAS exon 2 can be mediated by SSOs targeting ESEs located to several different sequences domains. This reflects that due to its weak splice sites HRAS exon 2 is particularly vulnerable and dependent on the simultaneous activity of several ESEs located to the different fragments bound by our SSOs.

Our data indicate that masking of ESEs by SEQ ID NO 6 or SEQ ID NO 7 is particularly efficient in inducing exon 2 skipping. This is consistent with our data showing that ESE-D is particularly important for exon 2 inclusion in the HRAS and KRAS genes (FIG. 5B and FIG. 13), since SEQ ID NO 6 blocks ESE-D. SEQ ID NO 7 blocks access to ESE-C, which is important for exon 2 inclusion in the HRAS, KRAS and NRAS genes (FIG. 5B and FIG. 13), explaining why its effective in mediating exon 2 skipping. Because ESE-C and ESE-D are important, we designed SSOs (SEQ ID NO 56 and SEQ ID 57) that could simultaneously block access to both ESEs and used these SSOs to treat T24 cells (FIG. 20). Both SEQ ID NO 56 and SEQ ID 57 are effective in causing exon 2 skipping although SEQ ID 57 is significantly shorter (only 20 nucleotides long). This further supported that ESE-C and ESE-D are fundamental for RAS exon 2 inclusion.

Masking of the splice sites by SEQ ID NO 3 or SEQ ID NO 11 also induces significant exon 2 skipping. Although a significant exon 2 skipping effect was observed for SEQ ID 1, SEQ ID 4 and SEQ ID 5, when applied to the HRAS minigene, the exon 2 skipping effect of these SSOs were limited when applied to the endogenous HRAS gene in T24 and HepG2 cells, despite the fact that SEQ ID 4 and SEQ ID 5, similar to SEQ ID 2, target ESE-A and ESE-B (FIG. 10). The level of skipping produced by each SSO at 20 nmol/l, 30 nmol/l, 40 nmol/l or 100 nmol/l was determined by employing a HRAS endogenous specific primer, which corresponds to the untranslated region of exon 1 in HRAS cDNA position −82 to −56 and introduces a NheI restriction site (SEQ ID NO 45 5'-HRAS1sNheI: 5'-GGC-CCCGCTAGCAGTCGCGCCTGTGAA-3') and a primer complementary to HRAS cDNA position 305-286 (SEQ ID NO 48 namely 5'-CGTTTGATCTGCTCCCTGTAC-3') of endogenous HRAS by PCR. This produces a 387 bp long product with exon 2 included and a 223 bp long product when exon 2 is skipped.

The transfections were performed in duplicate and the experiments repeated twice using Lipofectamine® RNAiMax.

In order to confirm that HRAS exon 2 skipping resulting from SSO treatment leads to decreased amounts of HRAS protein in treated cells the present inventors treated T24 with the SSOs at 30 nmol/l, and measured the amount of HRAS protein by Western blotting (FIG. 9B). This documented that exon 2 skipping induced by SSOs result in low amounts of HRAS protein.

In order to assess if HRAS exon 2 skipping resulting from SSO treatment affects proliferation and cell viability, the present inventors treated T24 and HepG2 cells with the SSOs at 30 nmol/l, and measured cell viability/proliferation by a colorimetric WST-1 assay and cell death by SYTOX-green/FACS analysis. Additionally, the present inventors employed phase-contrast microscopy of cells to observe morphological changes and reduced density indicating cell death. As illustrated for T24 bladder cancer cells in (FIG. 10), (FIG. 11) and (FIG. 12) this showed that SSO treatment and concomitant exon 2 skipping leads to decreased proliferation and causes cell death in cancer cells. Treatment with SEQ ID NO 6 or with SEQ ID NO 7 results in the highest degree of HRAS exon 2 skipping, the lowest values in WST-1 assay (indicating reduced growth and proliferation) and the highest number of death cancer cells, showing that the degree of HRAS exon 2 skipping resulting from SSO treatment correlates with inhibition of cancer cell growth, proliferation and the degree of cell death. The transfections were performed in duplicate and the experiments repeated at least twice using Lipofectamine® RNAiMax.

SSO-Mediated Skipping of KRAS Exon 2

Because exon 2 of KRAS was demonstrated to be weakly defined with suboptimal splice sites and thus dependent on splicing stimulatory motifs like ESEs, it was expected to be an optimal target for SSO-mediated exon 2 skipping.

Moreover, exon 2 and the flanking splice sites from the three RAS genes, HRAS, KRAS and NRAS are highly conserved and show extensive sequence homology. A 113 nucleotides long proportion of exon 2 starting at the translation initiation codon (Position c.1-c.111 in NM_001130442.1, NM_005343.2, NM_176795.3, NM_004985.3, NM_033360.2 and NM_002524.4) exhibits more than 80% identical nucleotides. Therefore many splicing regulatory elements, like ESEs, located in this region are conserved between the three RAS genes.

It is therefore likely that conserved sequence elements, such as ESEs, that the present inventors have identified (FIG. 13) to be responsive to SSO mediated exon 2 skipping in HRAS exon 2 are also responsive to SSO-mediated skipping in KRAS exon 2.

Finally, because the biological function of the part of the three RAS proteins, which is encoded by exon 2 belongs to the highly conserved amino terminal proportion, skipping of KRAS exon 2 is expected to abolish KRAS function, as the present inventors observed for HRAS exon 2 skipping, which abolishes HRAS function. Skipping of KRAS exon 2 would also lead to a non-functional protein, since both the start codon and amino acids critical for the function of KRAS are located in exon 2.

Blocking ESE motifs located in the conserved region (KRAS nucleotides no. c.1-c.112) of KRAS exon 2 that is conserved between KRAS and HRAS and which has in HRAS been demonstrated to respond to SSOs treatment with SEQ ID NO 2, SEQ ID NO 6, SEQ ID NO 7, SEQ ID NO 56 or SEQ ID NO 57 by HRAS exon 2 skipping, would result in that KRAS exon 2 is no longer recognized as an exon, and spliced out with neighboring introns. Such KRAS exon 2 skipping is therefore mediated by SEQ ID NO 20, SEQ ID 67 and SEQ ID 68, which all blocks access to the region of KRAS, which is homologous to ESE-A in HRAS (FIG. 13, 16). SEQ ID NO 60, SEQ ID NO 61, SEQ ID 62, SEQ ID NO 63, SEQ ID NO 64, SEQ ID NO 65, SEQ ID NO 66, SEQ ID NO 69, SEQ ID NO 70, SEQ ID NO 71, SEQ ID NO 72, SEQ ID NO 73 and SEQ ID 74 all block access to ESE-B (FIG. 13) and are therefore also expected to mediate KRAS exon 2 skipping. Likewise, because SEQ ID NO 60, SEQ ID NO 61, SEQ ID 62, SEQ ID NO 63, SEQ ID NO 64, SEQ ID NO 67, SEQ ID NO 68, SEQ ID NO 69, SEQ ID NO 72 and SEQ ID NO 74 all block access to the region of KRAS, which is homologous to ESE-A in HRAS (FIG. 13) they are therefore also likely to mediate KRAS exon 2 skipping.

In particular, because SEQ ID NO 21 blocks access to ESE-B and SEQ ID NO 22 and SEQ ID NO 75 each simultaneously blocks access to ESE-C and ESE-D these SSOs are likely to mediated KRAS exon 2 skipping. SEQ ID NO 19 targets a different segment of KRAS exon 2 overlapping with a homologous sequence element (c.5-c.10 in all three RAS genes) in HRAS exon 2 and NRAS exon 2, which when targeted by SSO SEQ ID NO 10 causes HRAS exon 2 skipping (FIG. 10) and when targeted by SSO SEQ ID NO 25 causes NRAS exon 2 skipping (FIG. 19).

Therefore SEQ ID NO 19 mediates KRAS exon 2 skipping by blocking a conserved ESE element critical for HRAS, KRAS and NRAS exon 2 inclusion (FIG. 16).

The splice sites usually offer obvious initial targets, and acceptor splice sites have been suggested as good targets for exon skipping in many exons. In an acceptor site the last 5-10 bases of the intron and first 15-20 bases of exon sequences are typically selected, while SSO targeting the donor site may contain up to 20 bases of intronic sequence [Adkin et al. 2012]. Intronic sequences may also be used as targets for SSO-mediated altered exon inclusion [Hua et al 2008].

As PTO linkages have shown high stability of the oligonucleotides in vivo, and 2'Ome-PTOs do not mediate degradation of the targeted pre-mRNA, a series of twentyseven different 2'OMe-PTO SSOs were synthesized to target either the 3' or 5' splice sites, the conserved parts of KRAS exon 2, as well as other parts of KRAS exon 2, or sequences in KRAS intron 1 and intron 2.

SSO treatment of T24 bladder cancer cells and HepG2 liver cancer cells was performed with SSOs to induce endogenous KRAS exon 2 skipping. A dose of 40 nmol/l was found to be efficient as illustrated for HepG2 and T24 cells treated with SEQ ID NO 12 and SEQ ID NO 13 which target the KRAS exon 2 splice sites (FIG. 14). The level of exon 2 skipping produced by each SSO at 40 nmol/l or 100 nmol/l was determined by employing a KRAS endogenous specific primer, which corresponds to the untranslated region of exon 1 in KRAS cDNA position −42 to −22 (5'-AGGCTCAGCGGCTCCCAGGTG-3' as SEQ ID NO 43) and a primer complementary to KRAS cDNA position c.316-c.282 (5'-GAGTCCTTAACTCTTTTAATTTGT-TCTCTATAATGG-3' as SEQ ID NO 44) of endogenous KRAS by PCR. This produces a 359 bp long product with exon 2 included and a 237 bp long product when exon 2 is skipped.

The transfections were performed in duplicate and the experiments repeated twice using Lipofectamine® RNAiMax. Decreased cell proliferation resulting from treatment with SEQ ID NO 12 and SEQ ID NO 13 was demonstrated by WST-1 assay, (FIG. 14) in both T24 and HepG2 cancer cells. Pronounced cell death resulting from treatment with SEQ ID NO 12 or SEQ ID NO 13 or a combination of both SEQ ID NO 12 and SEQ ID NO 13 was demonstrated by phase contrast light microscopy (FIG. 15). This shows that SSO mediated KRAS exon 2 skipping leads to decreased proliferation and cell death of T24 and HepG2 cancer cells.

Treatment of T24 cancer cells with a dose of 30 nmol/l of nmol/l SEQ ID NO 19, SEQ ID NO 20, SEQ ID NO 21 or SEQ ID NO 22 for 48 hours (FIG. 16) shows that the SSOs mediate exon 2 skipping at a low SSO dose of 30 nmol/l. This also shows that similar to other reported exons, which have been found to be particularly well suited for SSO mediated exon skipping (Fletcher et al. 2012), skipping of KRAS exon 2 can be mediated by SSOs targeting ESEs located to different sequences domains. This reflects that due to its weak splice sites KRAS exon 2 is particularly vulnerable and dependent on the simultaneous activity of several ESEs located to the different fragments bound by our SSOs.

Our data indicate that blocking of ESE-C and ESE-D (FIG. 13) by SEQ ID NO 21 or SEQ ID NO 22 is particularly efficient in inducing KRAS exon 2 skipping. This is consistent with fact that the present inventors have demonstrated that SSOs that block access to these ESEs in HRAS are particularly responsive to SSO mediated exon 2 skipping also in HRAS when treating with SEQ ID NO 6, SEQ ID NO 7, SEQ ID NO 56 or SEQ ID NO 57.

The inventors treated MiaPaCa-2 and Panc-1 pancreatic cancer cells with SSOs targeting ESE-C and ESE-D, namely SEQ ID NO 21, SEQ ID NO 22, SEQ ID 63, SEQ 65 or SEQ ID 72 (FIG. 21, FIG. 22 and FIG. 23) along with other SSOs targeting ESE-A or ESE-A and ESE-B to investigate the effect of SSO treatment in other cancer types and investigate the effect of alternative SSO designs for targeting these important ESEs. The results confirmed that targeting ESE-C and ESE-D by SEQ ID NO 21 and SEQ ID NO 22 mediated efficient KRAS exon 2 skipping, reduced growth and proliferation and cell death in two other cancer cell types (FIG. 21 and FIG. 22). Treatment of Panc-1 cells with SEQ ID NO 20, SEQ ID NO 21 and SEQ ID NO 22 showed that the mediated exon 2 skipping effect is dose dependent (FIG. 22).

Treatment of MiaPaCa-2 cells showed that simultaneous blocking of ESE-A and ESE-B with SEQ ID NO 63 or SEQ ID NO 72 or blocking of only ESE-A by SEQ ID NO 65 is particularly effective in mediating skipping of KRAS exon 2.

This further supports that blocking access to ESE-A, ESE-B, ESE-C or ESE-D is particularly well suited for SSO-mediated skipping in KRAS and HRAS exon 2.

The inventors also treated MiaPaCa-2 pancreatic cancer cells with an SSO, SEQ ID NO 74, with a short (20 nt) hybridizing region and a version of this SSO (SEQ ID NO 74), which has a tail (SEQ ID NO 34) added to the 3' end (FIG. 23). Despite masking ESE-A and ESE-B the short (20 nt) SEQ ID NO 74 without an added tail only has a modest effect on KRAS exon 2 skipping, but when the tail (SEQ ID NO 34) is added the elongated SSO consisting of both SEQ ID NO 74 and SEQ ID NO 34 is very efficient in in mediating KRAS exon 2 skipping. This shows, that adding a tail with a sequence, which can bind and thereby recruit negative splicing regulatory proteins from the hnRNPF/H family to an SSO increases skipping of KRAS exon 2. This is consistent with our findings that binding of hnRNPF/H causes skipping of HRAS exon 2 and underscores that these negative splicing regulators mediates exon 2 skipping, when when recruited to exon 2 of the RAS genes.

Blocking of the splice sites by treatment with a low dose of 30 nmol/l of SEQ ID NO 12 or SEQ ID NO 13 also induces significant exon 2 skipping and shows that SEQ ID NO 12 is more efficient in inducing KRAS exon 2 skipping than SEQ ID NO 13 (FIG. 16).

Treatment with 30 nmol/l of SSOs targeting KRAS intron 1 (SEQ ID NO 17 and SEQ ID NO 18) had only modest effect on KRAS exon 2 skipping and treatment with 30 nmol/l of SSOs targeting KRAS intron 2 (SEQ ID NO 14, SEQ ID NO 15 and SEQ ID NO 16) had no effect on KRAS exon 2 skipping (FIG. 16).

The level of skipping produced by SSO treatment was determined by employing a KRAS endogenous specific primer, which corresponds to the untranslated region of exon 1 in KRAS cDNA position −42 to −22 (5'-AGGCTCAGCG-GCTCCCAGGTG-3' or SEQ ID NO 43) and a primer complementary to KRAS cDNA position c.316-c.282 (5'-GAGTCCTTAACTCTTTTAATTTGTTCTCTATAATGG-3' or SEQ ID NO 44) of endogenous KRAS by PCR. This produces a 359 bp long product with exon 2 included and a 237 bp long product when exon 2 is skipped.

The transfections were performed in duplicate and the experiments repeated twice using Lipofectamine® RNAiMax. In order to further assess the effect on cancer cell proliferation and viability resulting from treatment with two of the most efficient SSOs targeting KRAS exon 2, the present inventors treated T24 cells with 30 nmol/l, SEQ ID NO 21 or SEQ ID NO 22 and measured cell viability/proliferation by a colorimetric WST-1 assay and cell death by SYTOX-green/FACS analysis. Additionally, the present inventors employed phase-contrast microscopy of T24 cells to observe morphological changes and reduced density indicating cell death. As illustrated in FIG. 11, FIG. 15, FIG. 16 and FIG. 21 this showed that SSO treatment with SEQ ID NO 21 or SEQ ID NO 22 induces dramatic KRAS exon 2 skipping and concomitantly leads to decreased proliferation and causes cell death of cancer cells. The transfections were performed in duplicate and the experiments repeated twice using Lipofectamine® RNAiMax.

SSO-Mediated Skipping of NRAS Exon 2

Because exon 2 of NRAS was demonstrated to be weakly defined with suboptimal splice sites and thus dependent on splicing stimulatory motifs like ESEs, it was expected to be an optimal target for SSO-mediated exon 2 skipping.

Moreover, exon 2 and the flanking splice sites from the three RAS genes, HRAS, KRAS and NRAS are highly conserved and show extensive sequence homology. A 113 nucleotides long proportion of exon 2 starting at the translation initiation codon (FIG. 13) (Position c.1-c.111 in NM_001130442.1, NM_005343.2, NM_176795.3, NM_004985.3, NM_033360.2 and NM_002524.4) exhibits more than 80% identical nucleotides. Therefore many splicing regulatory elements, like ESEs, located in this region are conserved between the three RAS genes. It is therefore likely that conserved sequence elements, such as ESEs that the present inventors have identified (FIG. 13) to be responsive to SSO-mediated exon 2 skipping in HRAS exon 2 and KRAS exon 2 are also responsive to SSO-mediated skipping in NRAS exon 2.

Finally, because the biological function of the part of the three RAS proteins, which is encoded by exon 2 belongs to the highly conserved amino terminal proportion, skipping of NRAS exon 2 is expected to abolish NRAS function, as observed for HRAS exon 2 skipping, which abolish HRAS function and for KRAS exon 2 skipping, which abolish KRAS function. Skipping of NRAS exon 2 would lead to a non-functional protein, since both the start codon and amino acids critical for the function of NRAS are located in exon 2.

Blocking ESE motifs located in the conserved region (NRAS nucleotides no. c.1-c.112) of NRAS exon 2 which are conserved between NRAS and HRAS and KRAS, and which has in HRAS been demonstrated to respond to SSOs treatment with SEQ ID NO 2, SEQ ID NO 6 or SEQ ID NO 7 or SEQ ID NO 56, or SEQ ID NO 57, by HRAS exon 2 skipping, would result in that NRAS exon 2 is no longer recognized as an exon, and spliced out with neighboring introns. Blocking of ESE-A, ESE-B and ESE-C (FIG. 13) by SSOs like SEQ ID NO 27 and SEQ ID NO 28, targeting NRAS therefore cause such NRAS exon 2 skipping.

Moreover, blocking of other critical ESEs, like a conserved ESE element (c.5-c.10 in all three RAS genes) critical for HRAS and KRAS exon 2 inclusion (FIG. 10 and FIG. 16) within NRAS exon 2 by SEQ ID NO 25 also lead to NRAS exon 2 skipping.

The splice sites usually offer obvious initial targets, and acceptor splice sites have been suggested as good targets for exon skipping in many exons. In an acceptor site the last 5-10 bases of the intron and first 15-20 bases of exon sequences are typically selected, while SSO targeting the donor site may contain up to 20 bases of intronic sequence [Adkin et al. 2012]. Intronic sequences may also be used as targets for SSO-mediated altered exon inclusion [Hua et al 2008].

As PTO linkages have shown high stability of the oligonucleotides in vivo, and 2'Ome-PTOs do not mediate degradation of the targeted pre-mRNA, a series of nine different 2'OMe-PTO SSOs were synthesized to target either the 3' or 5' splice sites, the conserved part of NRAS exon 2, as well as other parts of NRAS exon 2, or sequences in NRAS intron 1 and intron 2.

SSO treatment of T24 and HepG2 cancer cells was performed with SSOs, which target the NRAS exon 2 splice sites to induce endogenous NRAS exon 2 skipping. A dose of 40 nmol/l of SEQ ID NO 23 was found to be efficient as illustrated for HepG2 and T24 cells treated, whereas SEQ ID NO 24 requires a dose of 100 nmol/l to be efficient (FIG. 17). The level of exon 2 skipping produced by each SSO at 40 nmol/l or 100 nmol/l was determined by employing a NRAS endogenous specific primer, which corresponds to the untranslated region of exon 1 in NRAS cDNA position −53 to −23 (SEQ ID NO 49 as 5'-CTAAATCTGTCCAAAGCA-GAGGCAGTGGAGC-3') and a primer complementary to NRAS cDNA position c.315-c.280 (5'-TCTTTTACTCGCT- TAATCTGCTCCCTGTAGAGGTT-3' or SEQ ID NO 50) of endogenous NRAS by PCR. This produces a 367 bp long product with exon 2 included and a 239 bp long product when exon 2 is skipped. The transfections were performed in duplicate and the experiments repeated twice using Lipofectamine® RNAiMax.

Decreased cell proliferation resulting from treatment with SEQ ID NO 23 or SEQ ID NO 24 was demonstrated by WST-1 assay (FIG. 17) in both T24 and HepG2 cancer cells, with SEQ ID NO 23 being significantly more efficient than SEQ ID NO 24, consistent with the observed difference in NRAS exon 2 skipping induced by these SSOs. Pronounced cell death resulting from treatment with SEQ ID NO 23, or a combination of both SEQ ID NO 23 and SEQ ID NO 24 was demonstrated by phase contrast light microscopy (FIG. 18). This shows that SSO-mediated NRAS exon 2 skipping leads to decreased proliferation and cell death of T24 and HepG2 cancer cells.

Treatment of T24 cancer cells with a dose of 30 nmol/l of nmol/l SEQ ID NO 25, SEQ ID NO 27, SEQ ID NO 28 for 48 hours (FIG. 19) shows that the SSOs mediate exon 2 skipping at a low SSO dose of 30 nmol/l. This also shows that similar to other reported exons, which have been found to be particularly well suited for SSO-mediated exon skipping (Fletcher et al. 2012), skipping of NRAS exon 2 can be mediated by SSOs targeting ESEs located to different sequences domains. This reflects that due to its weak splice sites NRAS exon 2 is particularly vulnerable and dependent on the simultaneous activity of several ESEs located to the different fragments bound by our SSOs. In particular, blocking ESE-A, ESE-B, ESE-C (FIG. 13) and a conserved ESE located at position c.5-10 mediate efficient skipping of NRAS exon 2 (FIG. 19).

Our data show that blocking of ESEs located in the conserved region (FIG. 13) by SEQ ID NO 27 or SEQ ID NO 28 is particularly efficient in inducing NRAS exon 2 skipping. SEQ ID NO 27 and SEQ ID NO 28 both target the region of NRAS exon 2 that exhibits more than 80% identical nucleotides between the RAS genes, and which the present inventors have demonstrated to be particularly responsive to SSO mediated exon 2 skipping also in HRAS when treating with SEQ ID NO 6 or SEQ ID NO 7 or SEQ ID NO 56 or SEQ ID NO 57 and in KRAS when treating with SEQ ID NO 21 or SEQ ID NO 22 or other SSOs blocking access to important ESEs like ESE-A, ESE-B or ESE-C. This shows that this part of the conserved region is particularly responsive to SSO-mediated skipping in NRAS exon 2. SEQ ID NO 25 targets a different segment of NRAS exon 2 overlapping with a homologous sequence element (c.5-c.10 in all three RAS genes) in HRAS exon 2 and KRAS exon 2, which when targeted by SSO SEQ ID NO 10 causes HRAS exon 2 skipping (FIG. 10) and when targeted by SSO SEQ ID NO 19 causes KRAS exon 2 skipping (FIG. 16).

Therefore SEQ ID NO 25 mediates NRAS exon 2 skipping by blocking a conserved ESE element (c.5-c.10 in all three RAS genes) critical for HRAS, KRAS and NRAS exon 2 inclusion (FIG. 19).

Masking of the splice sites by treatment with a low dose of 30 nmol/l of SEQ ID NO 23 or SEQ ID NO 24 also induces significant exon 2 skipping and shows that SEQ ID NO 23 is more efficient in inducing exon 2 skipping than SEQ ID NO 24 (FIG. 19). Treatment with 30 nmol/l of SSOs targeting NRAS intron 1 (SEQ ID NO 30) had only a modest effect on NRAS exon 2 skipping. Treatment with 30 nmol/l of SSOs targeting NRAS intron 2 (SEQ ID NO 31) had no effect on NRAS exon 2 skipping (FIG. 19).

The level of exon 2 skipping produced by each SSO at 30 nmol/l, 40 nmol/l or 100 nmol/l was determined by employing a NRAS endogenous specific primer, which corresponds to the untranslated region of exon 1 in NRAS cDNA position −53 to −23 (5'-CTAAATCTGTCCAAAGCAGAGGCA-GTGGAGC-3' or SEQ ID NO 49) and a primer complementary to NRAS cDNA position c.315-c.280 (5'-TCTTT-TACTCGCTTAATCTGCTCCCTGTAGAGGTT-3' or SEQ ID NO 50) of endogenous NRAS by PCR. This produces a 367 bp long product with exon 2 included and a 239 bp long product when exon 2 is skipped. The transfections were performed in duplicate and the experiments repeated twice using Lipofectamine® RNAiMax.

In order to assess the effect on cancer cell proliferation and viability resulting from treatment with the most efficient SSOs targeting NRAS exon 2, the present inventors treated T24 cells with 30 nmol/l, SEQ ID NO 27 or SEQ ID NO 28 and measured cell viability/proliferation by a colorimetric WST-1 assay and cell death by SYTOX-green/FACS analysis. Additionally, the present inventors employed phase-contrast microscopy of T24 cells to observe morphological changes and reduced cell density indicating cell death. As illustrated in FIG. 11, FIG. 18 and FIG. 19 this showed that SSO treatment with SEQ ID NO 27 or SEQ ID NO 28 induces significant NRAS exon 2 skipping and concomitantly leads to decreased proliferation and causes cell death of cancer cells.

Methods:

HRAS Minigene

Genomic DNA was used for PCR amplification of a fragment of the human HRAS gene encompassing exons 1-4 using Platinum® Pfx DNA Polymerase supplemented with enhancer solution (Invitrogen) and primers HRAS1sNheI: SEQ ID 45 and SEQ ID NO 54. The amplified fragment was digested with NheI and XhoI and cloned into the polylinker of pcDNA.3.1+ (Invitrogen). Mutations were introduced by site-directed mutagenesis using standard methods. All plasmids were sequenced by GATC Biotech AG (Germany) in order to exclude any PCR derived errors. DNA sequences were analyzed using CLC Main Workbench (version 6.6.1).

Cells and Minigene Transfection

T24 human urinary bladder cancer cells, HepG2 human hepatocellular carcinoma cells, HEK293 human embryonic kidney cells, HeLa human cervix adenocarcinoma cells and Cos-7 African green monkey kidney fibroblast-like cells were obtained from American Type Culture Collection (ATCC).

Cells (HEK293, HeLa, HepG2, T24 or Cos-7) were grown under standard conditions using 10% RPMI+++ (Lonza RPMI 1640 added 10% FCS, glutamine (100×) and pen/strep (1000 U/ml)) or 5% RPMI+++ (Lonza RPMI 1640 added 5% FCS, glutamine (100×) and pen/strep (1000 U/ml)) for Cos-7 cells. 24 hours before transfection the cells were seeded 9.6 cm2 six-well plates at a density of $2 \times 10^5$ (HEK293), $1.7 \times 10^5$ (HepG2), $1.9 \times 10^5$ (Cos-7), $1.2 \times 10^5$ (Hela) or $1.2 \times 10^5$ (T24) in 2 ml 5% or 10% RPMI+++ (25% confluence) and grown O.N. to a density of 50% confluence on the day of transfection. Cells were transfected with a total DNA ratio of 800 ng plasmids per well using FuGENE HD® 6 Transfection Reagent (Roche). For each transfection 2.4 µl FuGENE HD® 6 Transfection Reagent added to 97.6 µl RPMI+++ (RPMI without FCS, glutamine and pen/strep) was used. Cells were transfected with 600 ng of plasmid DNA of interest and co-transfected with 200 ng MCAD 362T plasmid [Nielsen et al. 2007] as a positive control. As negative control, either pcDNA3.1+ or RHC-Glo plasmids were used. The plasmids were incubated with the transfection reagent for 15 min at RT before added to the cells. Cells were incubated at 37° C., 5% CO2 and harvested for RNA 48 hours after transfection. All experiments were performed in triplicate.

RHC-Glo Splicing Reporter Minigene Analyses

HRAS exon 2 and variant double stranded DNA oligonucleotides corresponding to c.13-c.47 of HRAS exon 2 were inserted into the alternatively spliced second exon in the RHC-Glo splicing reporter minigene [Singh and Cooper, 2006]. The second exon in the RHC-Glo splicing reporter is immediately flanked upstream and downstream by the last and first 91 and 73 nucleotides of human β-globin intron 1, respectively. The distal upstream segment of intron 1 contains introns 1 and 3 of chicken skeletal troponin I (sTNI), and the distal downstream region of intron 2 contains the last 364 nucleotides of sTNI intron 3. Inclusion of the alternatively spliced second exon is critically dependent on the balance between ESE's and ESS's in the inserted sequence. The integrity of all constructs was confirmed by sequencing. Transfection studies and reverse transcription-polymerase chain reaction (RT-PCR) were performed as previously described [Heintz et al., 2012].

RNA Affinity Purification of Nuclear Proteins

The affinity purification of RNA binding proteins was performed with 3'-biotin coupled RNA oligonucleotides (DNA Technology, Denmark) as previously described [Nielsen et al., 2007]. The sequences of the RNA oligonucleotides were: HRASWt (SEQ ID 51 or 5'-GGUGGGCGCCGGCGGUGUGGGC-3', HRAS35T (SEQ ID 52 or 5'-GGUGGGCGCCGUCGGUGUGGGC-3'), and HRAS35-36TG (SEQ ID 53 or 5'-GGUGGGCGC-CGUGGGUGUGGGC-3') corresponding to position c.24_45 of HRAS mRNA. For each purification, 100 μmol of RNA oligonucleotide was coupled to 100 μl of streptavidin-coupled magnetic beads (Invitrogen) and incubated with HeLa nuclear extract (Cilbiotech S.A., Belgium). After washing, bound proteins were investigated by labelling with Isobaric tags for relative and absolute quantification (iTRAQ) and multi-dimensional liquid chromatography (LC) and tandem mass spectrometry (MS/MS) [Qin et al. 2013]. Briefly, eluted proteins were added 50 μl TEAB (20 mM) and DTT (10 mM) and incubated at 37° C. for 1 h. When cooled to RT samples were incubated with iodoacetamide (20 mM). Proteins were digested by 2 pg trypsin (12-16 h) and lyophilized. Two groups, each containing a different set of four peptides, were prepared. The peptides within each group were individually labeled with iTRAQ114, iTRAQ115, iTRAQ116 or iTRAQ117. iTRAQ labels were thawed and vortexed in 70 μl ethanol. Peptides were labeled at RT for 1½ h. Labeled peptides were pooled and lyophilized.

Peptides were each reconstituted in 0.1% TFA/H2O and individually injected into a Poros R3 micro-column. Peptides were eluted with 60% linear gradient of ACN/0.1% TFA and analyzed by liquid chromatography (LC) and tandem mass spectrometry (MS/MS). Eluted proteins were also analyzed by western blotting using a monoclonal mouse antibody towards SRSF1 (SF2/ASF) AK96 from Zymed Laboratories (Invitrogen) or a monoclonal antibody towards SRSF2 (sc-53518 from Santa Cruz Biotechnology, Santa Cruz, Calif.) or a monoclonal antibody towards hnRNPA1 (Monoclonal Anti-hnRNPA1, Clone 4610 cat. No. R9778 from Sigma) or polyclonal antibodies towards hnRNPA1, hnRNPA2/B1, hnRNPH, hnRNPF or SRSF5 (SRp40) (sc-10029, sc-10035, sc-10043, sc-15387 or sc-33418 from Santa Cruz Biotechnology, Santa Cruz, Calif.).

Reverse Transfection of HepG2, T24, MiaPaCa2 or Panc-1 Cells with SSOs

Approximately 300,000 HepG2, T24, MiaPaCa2 or Panc-1 cells were seeded in each well in a 6-well plate (Nunc) with 50 pmol (20 nM), 75 pmol (30 nM), 100 pmol (40 nM) or 250 pmol (100 nM) of the relevant 2'OMe-PTO SSO was reverse transfected into the cells using Lipofectamine® RNAiMAX transfection reagent (Invitrogen). Forty-eight hours after transfection cells were harvested for total RNA isolation by Isol (Invitrogen) or analyzed by either flow cytometry or the WST-1 viability assay. cDNA synthesis was performed using Superscript VILO cDNA Synthesis Kit (Invitrogen). Splicing analysis was carried out by PCR amplification and agarose gel electrophoresis. Splicing analysis of endogenous HRAS transcripts were performed by PCR with primers located in exon 1 (HRAS1sNheI: 5'-GGCCCCGCTAGCAGTCGCGCCTGT-GAA-3' or SEQ ID NO 45) and a primer spanning the exon 3-exon 4 junction of the HRAS gene (RasEx4Ex3: 5'-CGTTTGATCTGCTCCTGTAC-3' or SEQ ID NO 55). All experiments were performed at least in triplicate.

Flow Cytometry

For determination of cell death, cells were incubated 15 min at 37° C. with 0.5 μmol/l SYTOX green nucleic acid stain (Molecular probes, Invitrogen), which detects dead cells with disrupted plasma membrane. Cells were harvested by trypsinization and SYTOX green-positive cells were analyzed using a FACSCalibur (Becton Dickinson) flow cytometer. For each measurement, 10,000 cells were analyzed, and the acquired data were analyzed by the Cell Quest Pro Analysis software. All experiments were performed at least in duplicate.

Determination of Cell Viability and Proliferation

Cell viability was determined by the WST-1 viability assay (Roche) in 96 well plates following the manufacturer's instructions. $1.2 \times 10^5$ T24 cells/well were reverse transfected with 30 nM of Splice Shifting Oligonucleotides and incubated for 72 h. Absorbance was measured on a VERSAmax tunable microplate reader (Molecular devices) at 3, 4 and 5 hours after the addition of WST-1. Non-treated cells, cells treated only with Lipofectamine® RNAiMAX transfection reagent (Invitrogen) and a non-targeting scrambled ASO served as control. All experiments were performed at least in triplicate.

REFERENCES

Estep A L, Tidyman W E, Teitell M A, Cotter P D, Rauen K A. HRAS Mutations in Costello Syndrome: Detection of Constitutional Activating Mutations in Codon 12 and 13 and Loss of Wild-Type Allele in Maglignancy. *Am J Med Genet*, 140A:8-16 (2006)

Fasano O, Aldrich T, Tamanoi F, Taparowsky E, Furth M, Wigler M. Analysis of the transforming potential of the human H-ras gene by random mutagenesis. *Proc Natl Acad Sci*, 81:4008-4012 (1984)

Faustino N A, Cooper T A. Pre-mRNA splicing and human disease. *Genes Dev*, 17:419-437 (2003).

Fletcher S, Adkin C F, Meloni P, Wong B, Muntoni F, Kole R, Fragall C, Greer K, Johnsen R, Wilton S D. Targeted exon skipping to address "leaky" mutations in the dystrophin gene. Mol Ther Nucleic Acids. 1:e48. doi: 10.1038/mtna.2012.40 (2012).

Frischmeyer P A, Dietz H C. Nonsense-mediated decay in health and disease. *Hum Mol Genet*, 8:1893-1900 (1999)

Futreal P A, Coin L, Marshall M, Down T, Hubbard T, Wooster R, Rahman N, Stratton M. A census of human cancer genes. *Nat Rev Cancer,* 4:117-183 (2004)

Gal-Mark N, Schwartz S, Ram O, Eyras E, Ast G. The pivotal roles of TIA proteins in 5' splice-site selection of alu exons and across evolution. *PLoS Genet,* 5:e1000717 (2009)

Garg K, Green P. Differing patterns of selection in alternative and constitutive splice sites. *Genome Res,* 17:1015-1022 (2007)

Gravely B R. Sorting out the complexity of SR protein functions. *RNA,* 6:1197-1211 (2000).

Graveley B R, Hertel K J, Maniatis T. The role of U2AF35 and U2AF65 in enhancer-dependent splicing. *RNA,* 7:805-818 (2001)

Grewal T, Koese M, Tebar F, Enrich C. Differential Regulation of RasGAPs in Cancer. *Genes Cancer,* 2:288-297 (2011)

Gripp K W, Lin A E, Stabley D L, Nicholson L, Scott Jr. C I, Doyle D, Aoki Y, Matsubara Y, Zackai E H, Lapunzina P, Gonzalez-Meneses A, Holbrook J, Agresta C A, Gonzalez I L, Sol-Church K. HRAS Mutation Analysis in Costello Syndrome: Genotype and Phenotype Correlation. *Am J Med Genet,* 140A:1-7 (2006)

Gripp K W, Innes M A, Axelrad M E, Gillan T L, Parboosingh J S, Davies C, Leonard N J, Lapointe M, Doyle D, Catalano S, Nicholson L, Stabley D L, Sol-Church K. Costello syndrome associated with novel germline HRAS mutations: An attenuated phenotype? *Am J Med Genet,* 146A:683-690 (2008)

Gripp K W, Hopkins E, Sol-Church K, Stabley D L, Axelrad M E, Doyle D, Dobyns W B, Hudson C, Johnson J, Tenconi R, Graham G E, Sousa A B, Heller R, Piccione M, Corsello G, Herman G E, Tartaglia M, Lin A E. Phenotypic analysis of individuals with Costello syndrome due to HRAS p.G13C. *Am J Med Genet,* 155:706-716 (2011).

Desmet F O, Hamroun D, Lalande M, Collod-Béroud G, Claustres M, Béroud C (2009) Human Splicing Finder: an online bioinformatics tool to predict splicing signals. *Nucleic Acids Res.* 37(9)

Dobrowolski S F, Andersen H S, Doktor T K, Andresen B S (2010) The PAH c.30C>G synonymous variation (p.G10G) creates a common exonic splicing silencer. *Molecular Genetics and Metabolism* 100:316-323.

Fernández-Medarde A, Santos E (2011). Ras in cancer and developmental diseases. *Genes Cancer.* 2(3):344-58.

Gripp K W, Hopkins E, Serrano A, Leonard N J, Stabley D L, Sol-Church K. Transmission of the rare HRAS mutation (c.173C>T; p.T58I) further illustrates its attenuated phenotype. *Am J Med Genet,* 158A:1095-1101 (2012)

Gschwind A, Fisher O M, Ullrich A. The discovery of receptor tyrosine kinases: targets for cancer therapy. *Nature rev,* 4:361-370 (2004)

Hancock J F. Ras proteins: Different signals from different locations, *Nature Rev,* 4:373-384 (2003)

Harding P L, Fall A M, Honeyman K, Fletcher S, Wilton S D. The influence of antisense oligonucleotide length dystrophin exon skipping. *Mol Ther,* 15:157-166 (2007)

Helderman-van den Enden A T J M, Straathof C S M, Aartsma-Rus A, den Dunnen J T, Verbist B M, Bakker E, Verschuuren J J, Ginjaar H B. Becker muscular dystrophy patiens with deletions around exon 51: a promising outlook for exon skipping therapy in Duchenne patients. *Neuromuscu. Disord,* 20:251-254 (2010)

Heintz C, Dobrowolski S F, Andersen H S, Demirkol M, Blau N, Andresen B S (2012). Splicing of phenylalanine hydroxylase (PAH) exon 11 is vulnerable—Molecular pathology of mutations in PAH exon 11. *Mol Genet Metab* 106:403-411.

Heldin C H. Dimerization of cell surface receptors in signal transduction. *Cell,* 80:213-223 (1995)

Hennekam R C. M. Costello syndrome. *Am J Med Genet,* 117C:42-48 (2003)

Hou S, Jones S, Choe L H, Papoutsakis E T, Lee K H. Workflow for quantitative proteomic analysis of *Clostridia acetobutylicum* ATCC 824 using iTRAQ tags. *Methods* (2013)

Hua Y, Krainer A R. Antisense-mediated exon inclusion. *Methods Mol Biol,* 867:307-323 (2012)

Hua Y, Sahashi K, Rigo F, Hung G, Horev G, Bennett C F, Krainer A R. Peripheral SMN restoration is essential for long-term rescue of severe spinal muscular atrophy mouse model. *Nature,* 478:123-126 (2011)

Hua Y, Vickers T A, Baker B F, Bennett F, Krainer A R. Enhancement of SMN2 Exon 7 Inclusion by Antisense Oligonucleotides Targeting the Exon. *PLoS Biol,* 5:e73 (2007)

Hua Y, Vickers T A, Okunola H L, Bennett C F, Krainer A R. Antisense masking of an hnRNP A1/A2 intronic splicing silencer corrects SMN2 splicing in transgenic mice. *Am J Hum Genet.* 82:834-48 (2008).

Huang Y, Steitz J A. SRprises along a Messenger's Journey. *Mol Cell* 17:613-615 (2005)

Iwasaki T, Chin W W, Ko Lan. Identification and Characterization of RRM-containing Coactivator Activator (CoAA) as TRBP-interacting Protein, and Its Splice Variant as a Coactivator Modulator (CoAM). *J Biol Chem,* 276:33375-33383 (2001)

Jacquenet S, Méreau A, Bilodeau P S, Damier L, Stoltzfus C M, Branlant C. A second Exon Splicing Silencer within Human Immunodeficiency Virus Type 1 tat Exon 2 Represses Splicing of Tat mRNA and Binds Protein hnRNP H. *J Biol Chem,* 276:40464-40475 (2001)

Kang J K, Malerba A, Popplewell L, Foster K, Dickson G. Antisense-induced Myostatin Exon Skipping Leads to Muscle Hypertrophy in Mice Following Octa-guanidine Morpholino Oligomer Treatment. *Mol Ther,* 19:159-164 (2011)

Kerr B, Delrue M-A, Sigaudy S, Perveen R, Marche M, Burgelin I, Stef M, Tang B, Eden O B, O'Sullivan J, De Sandre-Giovannoli A, Reardon W, Brewer C, Bennett C, Quarell O, M'Cann E, Donnai D, Stewart F, Hennekam R, Cavé H, Verloes A, Phillip N, Lacombe D, Levy N, Arveiler B, Black G. Genotype-pheotype correlation in Costello syndrome: HRAS mutation analysis in 43 cases. *J Med Genet,* 43:401-405 (2006)

Kerr B, Eden O B, Dandamudi R, Shannon N, Quarrell O, Emmerson A, Ladusans E, Gerrad M, Donnai D. Costello syndrome: two cases with embryonal rhabdomyosarcoma. *J Med Genet,* 35:1036-1039 (1998)

Kim H, Laor T, Horn P S, Wong B. Quantitative Assessment of the T2 Relaxation Time of the Gluteus Muscles in Children with Duchenne Muscular Dystrophy: a Comparative Study Before and After Steroid Treatment. *Korean J. Radiol.,* 11: 304-311 (2010)

Knobbe C B, Reifenberger J, Reifenberger G. Mutation analysis of the Ras pathway genes NRAS, HRAS, KRAS and BRAF in glioblastomas. *Acta Neuropathol,* 108:467-470 (2004)

Kobayashi H, Azuma R, Yasunaga T. Expression of excess receptors and negative feedback control of signal pathways are required for rapid activation and prompt cessation of signal transduction. *Cell Commun Signal,* 7:3 (2009)

Kole R, Krainer A R, Altman S. RNA therapeutics: beyond RNA interference and antisense oligonucleotides. *Nature Rev Drug Discov,* 11:125-140 (2012)

Kozak M. An analysis of 5'-noncoding sequence from 699 vertebrate messenger RNAs. *Nucleic Acids Res,* 20:8125-8148 (1987)

Krecic A M, Swanson M S. hnRNP complexes: composition, structure and function. *Curr Opin Cell Biol,* 11:363-371 (1999)

Ladd A N, Cooper T A. Finding signal that regulate alternative splicing in the post-genomic era. *Genome Biol,* 3:reviews0008 (2002)

Lamichhane R, Daubner G M, Thomas-Crusells J, Auweter S D, Manatschal C, Austin K S, Valniuk O, Allain F H, Rueda D. RNA looping by PTB: Evidence using FRET and NMR spectroscopy for a role in splicing repression. *Proc Natl Acad Sci,* 107:4105-4110 (2010)

LeFave C V, Squatrito M, Vorlova S, Rocco G L, Brennan C W, Holland E C, Pan Y X, Cartegni L. Splicing factor hnRNPH drives an oncogenic splicing switch in gliomas. *EMBO J,* 30:4084-4097 (2011)

Li X, Hoeppner L H, Jensen E D, Gopalakrishnan R, Westendorf J J. Co-activator Activator (CoAA) Prevents the Transcriptional Activity of Runt Domain Transcription Factors. *J Cell Biochem,* 108:378-387 (2009)

Lo I F M, Brewer C, Shannon N, Shorto J, Tang B, Black G, Soo M T, Ng D K K, Lam S T S, Kerr B. Severe neonatal manifestations of Costello syndrome. *J Med Genet,* 45:167-171 (2008)

Lodish H, Berk A, Zipursky S L, Matsudaira P, Baltimore D, Darnell J E. Molecular Cell Biology. 6th ed. W H. Freeman & Co (2008)

Lorenz S, Petersen C, KordaR U, Seidel H, Zenker M, Kutsche K. *J Med Genet,* 55:615-619 (2012)

López-Bigas N, Audit B, Ouzounis C, Parra G, Guigo R. Are splicing mutations the most frequent cause of hereditary disease. *FEBS Lett,* 579:1900-1993 (2005)

Losson R, Lacroute F. Interference of nonsense mutations with eukaryotic messenger RNA stability. *Proc Natl Acad Sci,* 76:5134-5137 (1979)

Malumbres M, Barbacid M. Ras oncogenes: the first 30 years. *Nature Rev Cancer,* 3:459-465 (2003)

Manley J L, Krainer A R. A rational nomenclature for serine/arginine-rich protein splicing factors (SR proteins). *Genes Dev,* 24:1073-1074 (2010)

Mann C J, Honeyman K, Cheng A J, Ly T, Lloyd F, Fletcher S, Morgan J E, Partridge T A, Wilton S D. Antisense-induced exon skipping and synthesis of dystrophin in the mdx mouse. *Proc Natl Acad Sci,* 98:42-47

Masuda A, Andersen H S, Doktor T K, Okamoto T, Ito M, Andresen B S, Ohno K. CUGBP1 and MBNL1 preferentially bind to 3' UTRs and facilitate mRNA decay. *Sci Rep,* 2:209 (2012)

McAlinden A, Havlioglu N, Liang L, Davies S R, Sandell L J. Alternative Splicing of Type II Procollagen Exon 2 Is Regulated by the Combination of a Weak 5' Splice site and an Adjacent Intronic Stem-loop Cis Element. *J Biol Chem,* 23:3700-32711 (2005)

Meister M, Tomasovic A, Banning A, Tikkanen R. Mitogen-Activated Protein (MAP) Kinase Scaffolding Proteins: A Recount. *Int J Mol Sci,* 14:4854-4884 (2013)

Muir L A and Chanberlain J S. Emerging strategies for cell and gene therapy of the muscular dystrophies. *Mol. Med.,* 11: e18 (2009)

Nielsen K B, Sorensen S, Cartegni L, corydon T J, Doktor T K, Schroeder L D, Reinert L S, Elpeleg O, Krainer A R, Gregersen N, Kiems J, Andresen B S. Seemingly Neutral Polymorphic Variations May Confer Immunity to Splicing-Inactivating Mutations: A synonymous SNP in Exon 5 of MCAD Protects from Deleterious Mutations in a flaking Exonic Splicing Enhancer. *Am J Hum Genet,* 80, 416-432 (2007)

Oliva J L, Zarich N, Martinez N, Jorge R, Castrillo A, Azañedo M, Garcia-Vargas S, Gutiérrez-Eisman, Juarranz A, Boscá L, Gutkind J S, Rojas J M. The P34 Mutation Reduces the Transforming Activity of K-Ras and N-Ras in NIH 3T3 Cells but Not of H-Ras. *J Biol Chem,* 279:33480-33491 (2004)

Oliveira J B, Bidere N, Niemela J E, Zheng L, Sakai K, Nix C P, Danner R L, Barb J, Munson P J, Puck J M, Dale J, Straus S E, Fleisher T A, Lenardo M J. NRAS mutation causes a human autoimmune lymphoproliferative syndrome. PNAS, 104:8953-8958 (2007) Palacios I M. Nonsense-mediated mRNA decay: from mechanistic insights to impacts on human health. *Brief Funct Genomics,* 12:25-36 (2012)

Pan Q, Shail O, Lee L J, Frey B J, Blencowel B. Deep surveying of alternative splicing complexity in the human transcriptome by high-throughput sequencing. *Nat Genet,* 40:1413-1415 (2008)

Parikh C, Subrahmanyam R, Ren R. Oncogenic NRAS, KRAS and HRAS exhibit Different Leukemogenic Potentials in Mice, *Cancer Res,* 67:7139-7146 (2007)

Passini M A, Bu J, Richards A M, Kinnecom C, Sardi S P, Stanek L M, Hua Y, Rigo F, Matson J, Hung G, Kaye E, Shihabuddin L, Krainer A R, Bennett F, Cheng S H. Antisense Oligonucleoides Delivered to the Mouse CNS Ameliorate Symtoms of Severe Spinal Muscular Atrophy. *Sci Transl Med,* 3:72ra18 (2011)

Pertea M, Mount S M, Salzberg S L. A computational survey of candidate exonic splicing enhancer motif in the model plant *Arabidopsis thaliana.* BMC Bioinformatics, 8:159 (2007)

Pheifer G P. p53 mutational spectra and the role of methylated CpG sequences. *Mutat Res,* 450:155-166 (2000)

Popplewell L J, Trollet C, Dickson G, Graham I R. Design of phosphorodiamidate morpholino oligomers (PMOs) for the induction of exon skipping of the human DMD gene. *Mol Ther,* 17:554-561 (2009)

Popplewell L J, Adkin C, Arechavala-Gomeza V, Aartsma-Rus A, de Winter C L, Wilton S D, Morgan J E, Muntoni F, Graham I R, Dickson G. Comparative analysis of antisense oligonucleotide sequences targeting exon 53 of the human DMD gene: implications for future clinical trials. *Neuromuscull Disord,* 20:102-110 (2010)

Pozzoli U, Sironi M. Silencers regulate both constitutive and alternative splicing events in mammals. *Cell Mol Life Sci,* 62:1579-1604 (2005)

Pramono Z A D, Wee K B, Wang J L, Chen Y J, Xiong Q B, Lai P S, Yee W C. A prospective Study in the Rational Design of Efficient Antisense Oligonucleotides for Exon Skipping in the DMD Gene. *Hum Gene Ther,* 23:781-790 (2012)

Punta M, Coggill P C, Eberhardt R Y, Mistry J, Tate J, Boursnell C, Pang N, Forslund K, Ceric G, Clements J, Heger A, Holm L, Sonnhammer E L L, Eddy S R, Bateman A, Finn R D. The Pfam protein families database. *Nucl Acids Res,* 40:D290-D301 (2012)

Qin J, Gu F, Liu D, Yin C, Zhao S, Chen H, Zhang J, Yang C, Zhan X, Zhang M. Proteomic analysis of elite soybean jidou17 and its parents using iTRAQ-based quantitative approaches. *Proteome Sci,* 11:12 (2013)

Quinlan M P, Quatela S E, Philips M R, Settleman J. Activated Kras, but not Nras or Nras, May Initiate Tumors of Endodermal Origin via Stem Cell Expansion. *Mol Cell Biol,* 28:2659-2674 (2008)

Raponi M, Kralovicova J, Copson E, Divina P, Eccles D, Johnson P, Baralle D, Vorechovsky I. Prediction of single-nucleotide substitutions that result in exon skipping identification of a splicing silencer in BRCA1 exon 6. *Hum Mutat,* 32:436-444 (2011)

Rauen K A; HRAS and the Costello syndrome. *Clin Genet,* 71:101-108 (2007)

Reumers J, Conde L, Medina I, Stroh-Maurer S, van Durme Joost, Dopazo J, Rousseau F, Schymkowitz J. Joint annotation of coding and non-coding single nucleotide polymorphisms and mutations in the SNPeffect and PupaSuite databses. *Nucleic Acids Res,* 36:825-829 (2008)

Roukos D H. Genome-wide association studies: how predictable is a person's cancer risk. *Expert Rev Anticancer Ther,* 9:389-392 (2009)

Sanaker P S, Toompuu M, McClorey G, Bindoff L A. Antisense oligonucleotide corrects splice abnormality in hereditary myopathy with lactic acidosis. Gene, 494:231-236 (2012)

Schaechter M, Ingraham J L, Neidhardt F C. Symbiosis, predation, and antibiosis. *ASM Press,* chapter 19:377-400 in Microbe (2006)

Schubbert S, Shannon K, Bollag G. Hyperactive Ras in developmental disorders and cancer. *Nat Rev Cancer,* 7:295-308 (2007)

Seeburg P H, Colby W W, Capon D J, Goeddel D V, Levinson A D. Biological properties of human c-Ha-ras1 genes mutated at codon 12. *Nature,* 312:71-75 (1984)

Sigaudy S, Vittu G, David A, Vigeron J, Lacombe D, Moncla A, Fiori E, Phillip N. Costello syndrome: Report of six patients including one with an embryonal rhabdomyosarcoma. *Eur J Pediatr,* 159:139-142 (2000)

Singh G, Cooper T A. Minigene reporter for identification and analysis of cis elements and trans factors affecting pre-mRNA splicing. *Biotechniques,* 41:177-181 (2006)

Singh N N, Seo J, Ottesen E W, Shishimorova M, Bhattacharya D, Singh R N. TIA1 Prevents Skipping of a Critical Exon Associated with Spinal Muscular Atrophy. *Mol Cell Biol,* 31:935-954 (2011)

Sironi M, Menozzi G, Riva L, Cagliani R, Comi G P. Bresolin N, Giorda R, Pozzoli U. Silencer elements as possible inhibitors of pseudoexon splicing. *Nucleic Acids Res,* 32:1783-1791 (2004)

Smith P J, Zhang C, Wang J, Chew S L, Zhang M Q and Krainer A R. An increase specificity score matrix for the prediction of SF2/AFS-specific exonic splicing enhancers. *Hum Mol Genet,* 15:2490-2508 (2006)

Sot B, Behrmann E, Raunser S, Wittinghofer A. Ras GTPase activating (RasGTP) activity of the dual specificity GAP protein Rasal requires colocalization and C2 domain binding to lipid membranes. *Proc Natl Acad Sci,* 110:111-116 (2013)

M L, Zamecnik P C. Inhibition of Rocus sarcoma viral RNA translation by specific oligodexyribonucleotide. *Proc Natl Acad Sci,* 75:285-288 (1978)

Swenson J, Carey J C, Calhoun A, Yi P, Vaughn C, Dobrowolski S, Stevenson D A. Viability of Germline HRAS G12V Mutation in Costello Syndrome Results from Reduced mRNA Expression Associated with Dinucleotide Substitutions. Poster made by Authers, University of Utah, SLC (2011) (unpublished)

To M D, Rosario R D, Westcott P M K, Banta K L, Balmain A. Interactions between wild-type and mutant Ras genes in lung and skin carcinogenesis. *Oncogene,* 1-6 (2012)

Trcek T, Sato H, Singer R H. Temporal and spatial characterization of nonsense-mediated mRNA decay. *Genes Dev,* 27:541-551 (2013)

Yeo G, Burge C B. Miximum Entropy Modeling of short Sequence Motifs with Applications to RNA Splicing Signals. *J Comput Biol,* 11:377-394 (2004)

Zamecnik P C, Stephenson M L. Inhibition of Rous sarcoma virus replication and cell transformation by a specific oligodeoxynucleotide. *Proc Natl Acad Sci,* 75:280-284 (1978)

Zampino G, Pantaleoni F, Carta C, Cobellis G, Vasta I, Neri C, Pogna E A, DeFeo E, Delogu A, Sarlozy A, Atzeri F, Selicorni A, Rauen K A, Cytrynbaum C S, Weksberg R, Dallapiccola B, Ballabio A, Gelb B D, Neri G, Tartaglia M. Diversity, parental germline origin and phenotypic spectrum of de novo HRAS missense changes in Costello syndrome. *Hum Mutat,* 28:265-272 (2007)

Zatkova A, Messiaen L, Vandenbroucke I, Weiser R, Fonatsch C, Krainer A R, Wimmer K. Disruption of Exonic Splicing Enhancer Elements Is the Principal Cause of Exonic Skipping Associated With Seven Nonsense or Missense Alleles of NF1. *Hum Mutat,* 24:492-501 (2004)

Zenker M. Clinical manifestations of mutations in RAS and related intracellular signal transduction factors. *Hum Genet,* 23:443-451 (2011)

Zheng Z-M, Quintero J, Reid E, Gocke C, Baker C. Optimization of a Weak 3' Splice site Counteracts the Function of a Bovine Papillomavirus Type 1 Exonic Splicing Suppressor In Vitro and In Vivo. *J Virol,* 74:5902-5910 (2000)

Van der Burgt I. Noonan syndrome. *Orphanet J Rare Dis,* 2:4 (2007)

Wang Z, Rolish M E, Yeo G, Tung V, Mawson M, Burge C B. Systematic identification and analysis of exonic splicing silencers. *Cell,* 119:831-845 (2004)

Wang Z, Burge C B. Splicing regulation: From a parts list of regulatory elements to an integrated splicing code. *RNA,* 14:802-813 (2008)

Nielsen K B, Sorensen S, Cartegni L, Corydon T J, Doktor T K, Schroeder L D, Reinert L S, Elpeleg O, Krainer A R, Gregersen N, Kjems J, Andresen B S. (2007). Seemingly neutral polymorphic variants may confer immunity to splicing-inactivating mutations: a synonymous SNP in exon 5 of MCAD protects from deleterious mutations in a flanking exonic splicing enhancer. Am J Hum Genet 80:416-432.

Olsen R K J, Brøner S, Sabaratnam R, Doktor T K, Andersen H S, Bruun G H, Gahrn B, Stenbroen V, Olpin S E, Dobbie A, Gregersen N, Andresen B S (2014) The ETFDH c.158A>G variant disrupts the balanced interplay of ESE- and ESS-binding proteins thereby causing missplicing and multiple acyl-CoA dehydrogenation deficiency. Human Mutation 35(1):86-95.

Masuda A, Shen X M, Ito M, Matsuura T, Engel A G, Ohno K. 2008. hnRNP H enhances skipping of a nonfunctional exon P3A in CHRNA1 and a mutation disrupting its binding causes congenital myasthenic syndrome. Hum Mol Genet 17:4022-4035.

Schaub M C, Lopez S R, Caputi M. 2007. Members of the heterogeneous nuclear ribonucleoprotein H family activate splicing of an HIV-1 splicing substrate by promoting formation of ATP-dependent spliceosomal complexes. J Biol Chem 282:13617-13626.

Sheth N, Roca X, Hastings M L, Roeder T, Krainer A R, Sachidanandam R. (2006) Comprehensive splice-site analysis using comparative genomics. Nucleic Acids Res. 34(14):3955-67.

Singh G, Cooper T A. 2006. Minigene reporter for identification and analysis of cis elements and trans factors affecting pre-mRNA splicing. BioTechniques 41:177-181

Sironi M, Menozzi G, Riva L, Cagliani R, Comi G P, Bresolin N, Giorda R, Pozzoli U. Silencer elements as possible inhibitors of pseudoexon splicing. Nucleic Acids Res. 2004 Mar. 19; 32(5):1783-91

Yeo G, Burge C B. 2004. Maximum entropy modeling of short sequence motifs with applications to RNA splicing signals. J Comput Biol 11:377-394.

The invention claimed is:

1. A method of modulating RAS splicing in a transcript in a cell, comprising contacting the cell with a splice shifting oligonucleotide (SSO) consisting of linked nucleosides comprising:
(i) 10 to 25 linked nucleosides having a nucleobase sequence comprising from 1 to 12 contiguous nucleobases complementary to a target region of equal length of a nucleic acid sequence harbouring a splicing regulatory sequence of 6-12 nucleotides comprised in the sequences selected from the list consisting of
SEQ ID NO: 76 (HRAS Exon 2+flanking sequences),
a nucleic acid sequence having at least 80% sequence identity to SEQ ID NO: 76,
a nucleic acid sequence having 1 or 2 substitutions when compared to SEQ ID NO 76,
SEQ ID NO: 77 (KRAS Exon 2+flanking sequences), and
a nucleic acid sequence having at least 80% sequence identity to SEQ ID NO: 77,
a nucleic acid sequence having 1 or 2 substitutions when compared to SEQ ID NO 77,
SEQ ID NO: 78 (NRAS Exon 2+flanking sequences),
a nucleic acid sequence having at least 80% sequence identity to SEQ ID NO: 78,
a nucleic acid sequence having 1 or 2 substitutions when compared to SEQ ID NO 78,
and wherein the oligonucleotide does not comprise a stretch of more than 5 consecutive unmodified RNA nucleosides;
and wherein said modulating comprises RAS Exon 2 skipping.

2. A method for treating a cancer characterized at least in part by constitutively active RAS or mutant RAS, comprising administering a therapeutically effective amount of a splice shifting oligonucleotide (SSO) consisting of linked nucleosides comprising:
(i) 10 to 25 linked nucleosides having a nucleobase sequence comprising from 1 to 12 contiguous nucleobases complementary to a target region of equal length of a nucleic acid sequence harbouring a splicing regulatory sequence of 6-12 nucleotides comprised in the sequences selected from the list consisting of
SEQ ID NO: 76 (HRAS Exon 2+flanking sequences),
a nucleic acid sequence having at least 80% sequence identity to SEQ ID NO: 76,
a nucleic acid sequence having 1 or 2 substitutions when compared to SEQ ID NO 76,
SEQ ID NO: 77 (KRAS Exon 2+flanking sequences), and
a nucleic acid sequence having at least 80% sequence identity to SEQ ID NO: 77,
a nucleic acid sequence having 1 or 2 substitutions when compared to SEQ ID NO 77,
SEQ ID NO: 78 (NRAS Exon 2+flanking sequences),
a nucleic acid sequence having at least 80% sequence identity to SEQ ID NO: 78,
a nucleic acid sequence having 1 or 2 substitutions when compared to SEQ ID NO 78,
and wherein the oligonucleotide does not comprise a stretch of more than 5 consecutive unmodified RNA nucleosides to a subject in need thereof, wherein said treating comprises inducing RAS Exon 2 skipping.

3. The method according to claim 2, wherein the cancer is selected from the group consisting of lung cancer, colorectal cancer, pancreas cancer, skin cancer, bladder cancer, multiple myeloma cancer, liver cancer, breast cancer, haematological cancer and prostate cancer.

4. A method for reducing proliferation of a cancer cell comprising the acts of:
administering a therapeutically effective amount of a splice shifting oligonucleotide (SSO) consisting of linked nucleosides comprising:
(i) 10 to 25 linked nucleosides having a nucleobase sequence comprising from 1 to 12 contiguous nucleobases complementary to a target region of equal length of a nucleic acid sequence harbouring a splicing regulatory sequence of 6-12 nucleotides comprised in the sequences selected from the list consisting of
SEQ ID NO: 76 (HRAS Exon 2+flanking sequences),
a nucleic acid sequence having at least 80% sequence identity to SEQ ID NO: 76,
a nucleic acid sequence having 1 or 2 substitutions when compared to SEQ ID NO 76,
SEQ ID NO: 77 (KRAS Exon 2+flanking sequences), and
a nucleic acid sequence having at least 80% sequence identity to SEQ ID NO: 77,
a nucleic acid sequence having 1 or 2 substitutions when compared to SEQ ID NO 77,
SEQ ID NO: 78 (NRAS Exon 2+flanking sequences),
a nucleic acid sequence having at least 80% sequence identity to SEQ ID NO: 78,
a nucleic acid sequence having 1 or 2 substitutions when compared to SEQ ID NO 78,
and wherein the oligonucleotide does not comprise a stretch of more than 5 consecutive unmodified RNA nucleosides, wherein the SSO induces RAS Exon 2 skipping in the cell.

5. The method of claim 4, wherein said cell is a lung cancer cell, colorectal cancer cell, pancreas cancer cell, skin cancer cell, bladder cancer cell, multiple myeloma cancer cell, liver cancer cell, breast cancer cell, haematological cancer or prostate cancer cell.

6. The method of claim 5, wherein said cell is a lung cancer cell.

7. The method of claim 1 wherein the SSO further comprises:
(ii) a fragment consisting of 10 to 30 linked nucleosides having a nucleobase sequence which is not complementary to a region of equal length of a nucleic acid sequence selected from the list consisting of
SEQ ID NO: 76 (HRAS Exon 2+flanking sequences),
SEQ ID NO: 78 (NRAS Exon 2+flanking sequences), and
SEQ ID NO: 77 (KRAS Exon 2+flanking sequences).

8. The method of claim 7 wherein said fragment (ii) contains at least one CAGGG(T/U) or (U/T)AGGGA motif.

9. The method of claim 7 wherein said fragment (ii) is capable of binding a splicing inhibitory protein from the hnRNPF/H family of splicing inhibitory proteins.

10. The method of claim 2 wherein the SSO further comprises:
(ii) a fragment consisting of 10 to 30 linked nucleosides having a nucleobase sequence which is not complementary to a region of equal length of a nucleic acid sequence selected from the list consisting of
SEQ ID NO: 76 (HRAS Exon 2+flanking sequences),
SEQ ID NO: 78 (NRAS Exon 2+flanking sequences), and
SEQ ID NO: 77 (KRAS Exon 2+flanking sequences).

11. The method of claim 4 wherein the SSO further comprises:
(ii) a fragment consisting of 10 to 30 linked nucleosides having a nucleobase sequence which is not complementary to a region of equal length of a nucleic acid sequence selected from the list consisting of
SEQ ID NO: 76 (HRAS Exon 2+flanking sequences),
SEQ ID NO: 78 (NRAS Exon 2+flanking sequences), and
SEQ ID NO: 77 (KRAS Exon 2+flanking sequences).

* * * * *